(12) United States Patent
Nandabalan et al.

(10) Patent No.: US 11,786,508 B2
(45) Date of Patent: *Oct. 17, 2023

(54) USE OF SUBLINGUAL DEXMEDETOMIDINE FOR THE TREATMENT OF AGITATION

(71) Applicant: BioXcel Therapeutics, Inc., New Haven, CT (US)

(72) Inventors: Krishnan Nandabalan, New Haven, CT (US); Frank Yocca, New Haven, CT (US); Sameer Sharma, New Haven, CT (US); Harsh Negi, New Delhi (IN); Deepa Saini, Ghaziabad (IN)

(73) Assignee: BioXcel Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,312

(22) Filed: Nov. 18, 2022

(65) Prior Publication Data

US 2023/0081503 A1 Mar. 16, 2023

Related U.S. Application Data

(63) Continuation of application No. 16/474,882, filed as application No. PCT/US2017/069030 on Dec. 29, 2017.

(60) Provisional application No. 62/542,323, filed on Aug. 8, 2017, provisional application No. 62/471,393, filed on Mar. 15, 2017, provisional application No. 62/441,164, filed on Dec. 31, 2016.

(51) Int. Cl.
| | |
|---|---|
| *A61K 31/4174* | (2006.01) |
| *A61K 9/00* | (2006.01) |
| *A61K 9/20* | (2006.01) |
| *A61K 45/06* | (2006.01) |
| *A61K 47/10* | (2017.01) |

(52) U.S. Cl.
CPC .......... *A61K 31/4174* (2013.01); *A61K 9/006* (2013.01); *A61K 9/2027* (2013.01); *A61K 45/06* (2013.01); *A61K 47/10* (2013.01)

(58) Field of Classification Search
CPC .. A61K 31/4174; A61K 9/006; A61K 9/2027; A61K 45/06; A61K 47/10
See application file for complete search history.

(56) References Cited

U.S. PATENT DOCUMENTS

| | | |
|---|---|---|
| 4,407,957 A | 10/1983 | Lim |
| 4,670,455 A | 6/1987 | Virtanen et al. |
| 4,760,093 A | 7/1988 | Blank et al. |
| 4,760,094 A | 7/1988 | Blank et al. |
| 4,767,789 A | 8/1988 | Blank et al. |
| 4,839,170 A | 6/1989 | Sarnoff et al. |
| 5,039,540 A | 8/1991 | Ecanow |
| 5,178,878 A | 1/1993 | Wehling et al. |
| 5,188,825 A | 2/1993 | Iles et al. |
| 5,217,718 A | 6/1993 | Colley et al. |
| 5,330,763 A | 7/1994 | Gole et al. |
| 5,395,907 A | 3/1995 | Zajaczkowski |
| 5,508,367 A | 4/1996 | Zajaczkowski |
| 5,520,639 A | 5/1996 | Peterson et al. |
| 5,565,268 A | 10/1996 | Zajaczkowski |
| 5,605,911 A | 2/1997 | Olney et al. |
| 5,631,023 A | 5/1997 | Kearney et al. |
| 5,654,007 A | 8/1997 | Johnson et al. |
| 5,700,873 A | 12/1997 | Zajaczkowski et al. |
| 5,704,911 A | 1/1998 | Parsons |
| 5,712,301 A | 1/1998 | Jaatinen et al. |
| 5,726,250 A | 3/1998 | Zajaczkowski |
| 5,729,958 A | 3/1998 | Kearney et al. |
| 5,731,387 A | 3/1998 | Zajaczkowski |
| 5,780,014 A | 7/1998 | Eljamal et al. |
| 5,798,113 A | 8/1998 | Dionne et al. |
| 5,814,607 A | 9/1998 | Patton |
| 5,817,332 A | 10/1998 | Urtti et al. |
| 5,820,875 A | 10/1998 | Fallon et al. |
| 5,827,541 A | 10/1998 | Yarwood et al. |
| 5,837,287 A | 11/1998 | Yarwood et al. |
| 5,846,233 A | 12/1998 | Lilley et al. |
| 5,879,327 A | 3/1999 | Moreau DeFarges et al. |
| 5,951,999 A | 9/1999 | Therriault et al. |
| 5,976,577 A | 11/1999 | Green et al. |
| 6,149,938 A | 11/2000 | Bonadeo et al. |
| 6,156,339 A | 12/2000 | Grother et al. |
| 6,174,546 B1 | 1/2001 | Therriault et al. |
| 6,200,604 B1 | 3/2001 | Pather et al. |
| 6,212,791 B1 | 4/2001 | Thompson et al. |
| 6,221,392 B1 | 4/2001 | Khankari et al. |
| 6,239,228 B1 | 5/2001 | Zajaczkowski et al. |

(Continued)

FOREIGN PATENT DOCUMENTS

| | | |
|---|---|---|
| AU | 2007201370 B2 | 9/2009 |
| AU | 2009238370 B2 | 7/2011 |

(Continued)

OTHER PUBLICATIONS

Aantaa, et al., "Intramuscular dexmedetomidine, a novel alpha2-adrenoceptor agonist, as premedication for minor gynaecological surgery." Acta Anaesthesiol Scand. (1991); 35(4): 283-288.

(Continued)

*Primary Examiner* — Adam C Milligan
(74) *Attorney, Agent, or Firm* — COOLEY LLP

(57) ABSTRACT

The present invention discloses a method of treating agitation or the signs of agitation in a subject comprising the sublingual administration of an effective amount of an alpha-2 adrenergic agonist, more particularly Dexmedetomidine, or a pharmaceutically acceptable salt thereof. The method is particularly suitable for the treatment of agitation associated with neurodegenerative and/or neuropsychiatric diseases. The present invention also discloses the sublingual administration of an alpha-2 adrenergic agonist, more particularly Dexmedetomidine or a pharmaceutically acceptable salt thereof at a dose that is effective to treat agitation or the signs of agitation in a subject, but does not cause significant sedation.

6 Claims, 14 Drawing Sheets

(56) References Cited

U.S. PATENT DOCUMENTS

| | | |
|---|---|---|
| 6,269,615 B1 | 8/2001 | Amborn et al. |
| 6,284,270 B1 | 9/2001 | Lagoviyer et al. |
| 6,297,240 B1 | 10/2001 | Embleton |
| 6,316,029 B1 | 11/2001 | Jain et al. |
| 6,413,549 B2 | 7/2002 | Green et al. |
| 6,465,010 B1 | 10/2002 | Lagoviyer et al. |
| 6,471,992 B1 | 10/2002 | Yoo et al. |
| 6,509,040 B1 | 1/2003 | Murray et al. |
| 6,709,669 B1 | 3/2004 | Murray et al. |
| 6,716,867 B1 | 4/2004 | Aantaa et al. |
| 6,726,928 B2 | 4/2004 | Yarwood et al. |
| 6,753,782 B2 | 6/2004 | Power |
| 6,814,978 B2 | 11/2004 | Bunick et al. |
| 6,908,626 B2 | 6/2005 | Cooper et al. |
| 6,982,251 B2 | 1/2006 | Ghosal et al. |
| 7,001,609 B1 | 2/2006 | Matson et al. |
| 7,282,217 B1 | 10/2007 | Grimshaw et al. |
| 7,357,891 B2 | 4/2008 | Yang et al. |
| 7,425,292 B2 | 9/2008 | Yang et al. |
| 7,425,341 B1 | 9/2008 | Grimshaw et al. |
| 7,470,397 B2 | 12/2008 | Meathrel et al. |
| 7,579,019 B2 | 8/2009 | Tapolsky et al. |
| 7,580,798 B2 | 8/2009 | Brunner et al. |
| 7,630,758 B2 | 12/2009 | Lapinlampi et al. |
| 7,666,337 B2 | 2/2010 | Yang et al. |
| 7,727,466 B2 | 6/2010 | Meathrel et al. |
| 7,897,080 B2 | 3/2011 | Yang et al. |
| 7,939,105 B2 | 5/2011 | Parikh et al. |
| 7,972,618 B2 | 7/2011 | Fuisz et al. |
| 7,972,621 B2 | 7/2011 | Wong et al. |
| 7,993,674 B2 | 8/2011 | Weibel |
| 8,048,449 B2 | 11/2011 | Kashid et al. |
| 8,127,516 B2 | 3/2012 | Lee et al. |
| 8,158,152 B2 | 4/2012 | Palepu |
| 8,221,480 B2 | 7/2012 | Boyden et al. |
| 8,241,661 B2 | 8/2012 | Fuisz et al. |
| 8,242,158 B1 | 8/2012 | Roychowdhury et al. |
| 8,256,233 B2 | 9/2012 | Boyden et al. |
| 8,282,954 B2 | 10/2012 | Bogue et al. |
| 8,313,768 B2 | 11/2012 | Kriksunov et al. |
| 8,324,260 B2 | 12/2012 | Garcia Da Rocha et al. |
| 8,338,470 B1 | 12/2012 | Roychowdhury et al. |
| 8,364,221 B2 | 1/2013 | Mannheimer et al. |
| 8,414,922 B2 | 4/2013 | Bryson et al. |
| 8,436,033 B1 | 5/2013 | Roychowdhury et al. |
| 8,455,527 B1 | 6/2013 | Roychowdhury et al. |
| 8,568,777 B2 | 10/2013 | Fuisz |
| 8,617,589 B2 | 12/2013 | Fuisz et al. |
| 8,648,106 B2 | 2/2014 | Roychowdhury et al. |
| 8,663,687 B2 | 3/2014 | Myers et al. |
| 8,663,696 B2 | 3/2014 | Myers et al. |
| 8,685,437 B2 | 4/2014 | Yang et al. |
| 8,846,074 B2 | 9/2014 | Bryson et al. |
| 8,882,684 B2 | 11/2014 | Halperin et al. |
| 8,882,703 B2 | 11/2014 | Hickle |
| 8,900,498 B2 | 12/2014 | Yang et al. |
| 8,936,825 B2 | 1/2015 | Myers et al. |
| 9,073,294 B2 | 7/2015 | Kumar et al. |
| 9,192,580 B2 | 11/2015 | Green et al. |
| 9,248,146 B2 | 2/2016 | Barnhart et al. |
| 9,283,219 B2 | 3/2016 | Bryson et al. |
| 9,303,918 B2 | 4/2016 | Li |
| 9,320,712 B2 | 4/2016 | Roychowdhury et al. |
| 9,346,601 B2 | 5/2016 | Bogue et al. |
| 9,427,412 B2 | 8/2016 | Bryson et al. |
| 9,441,142 B2 | 9/2016 | Malik et al. |
| 9,545,376 B2 | 1/2017 | Musho et al. |
| 9,561,191 B2 | 2/2017 | Myers et al. |
| 9,572,773 B2 | 2/2017 | Dormady et al. |
| 9,585,961 B2 | 3/2017 | Barnhart et al. |
| 9,616,049 B2 | 4/2017 | Roychowdhury et al. |
| 9,649,296 B1 | 5/2017 | Pizza |
| 9,662,297 B2 | 5/2017 | Musho et al. |
| 9,662,301 B2 | 5/2017 | Musho et al. |
| 9,717,796 B1 | 8/2017 | Pizza |
| 9,775,819 B2 | 10/2017 | Bahl et al. |
| 9,795,559 B2 | 10/2017 | Henwood et al. |
| 9,814,674 B2 | 11/2017 | Musho et al. |
| 9,855,221 B2 | 1/2018 | Myers et al. |
| 9,901,650 B2 | 2/2018 | Nedergaard et al. |
| 9,931,305 B2 | 4/2018 | Yang et al. |
| 9,937,122 B2 | 4/2018 | Zhu et al. |
| 9,937,123 B2 | 4/2018 | Barnhart et al. |
| 9,974,754 B2 | 5/2018 | Yamazaki et al. |
| 9,993,428 B2 | 6/2018 | Gerard et al. |
| 10,130,684 B2 | 11/2018 | Rubin et al. |
| 10,130,766 B1 | 11/2018 | Bibian et al. |
| 10,137,245 B2 | 11/2018 | Melker et al. |
| 10,285,953 B2 | 5/2019 | Bryson et al. |
| 10,314,503 B2 | 6/2019 | Prerau et al. |
| 10,383,574 B2 | 8/2019 | Purdon et al. |
| 10,548,839 B2 | 2/2020 | Tian |
| 10,602,978 B2 | 3/2020 | Purdon et al. |
| 10,792,246 B2 | 10/2020 | Kakumanu et al. |
| 11,116,723 B2 | 9/2021 | Temtsin-Krayz |
| 11,478,422 B2 | 10/2022 | Kakumanu et al. |
| 11,497,711 B2 | 11/2022 | Kakumanu et al. |
| 11,517,524 B2 | 12/2022 | Kakumanu et al. |
| 11,554,106 B2 | 1/2023 | Petitjean et al. |
| 11,559,484 B2 | 1/2023 | Kakumanu et al. |
| 2002/0037977 A1 | 3/2002 | Feldstein et al. |
| 2003/0096012 A1 | 5/2003 | Besse et al. |
| 2003/0124191 A1 | 7/2003 | Besse et al. |
| 2003/0145854 A1 | 8/2003 | Hickle |
| 2003/0158242 A1 | 8/2003 | Kugelmann |
| 2004/0138312 A1 | 7/2004 | Wheeler et al. |
| 2004/0156894 A1 | 8/2004 | Grother et al. |
| 2005/0037055 A1 | 2/2005 | Yang et al. |
| 2005/0118217 A1 | 6/2005 | Barnhart et al. |
| 2005/0222270 A1 | 10/2005 | Olney et al. |
| 2006/0058590 A1 | 3/2006 | Shaw et al. |
| 2006/0058700 A1 | 3/2006 | Marro et al. |
| 2006/0069086 A1 | 3/2006 | Michalow |
| 2006/0199805 A1 | 9/2006 | Pyke et al. |
| 2007/0117835 A1 | 5/2007 | Hung |
| 2007/0281003 A1 | 12/2007 | Fuisz et al. |
| 2008/0026040 A1 | 1/2008 | Farr et al. |
| 2008/0124381 A1 | 5/2008 | Barnhart et al. |
| 2008/0280947 A1 | 11/2008 | Blondino et al. |
| 2008/0299005 A1 | 12/2008 | Meathrel et al. |
| 2008/0306980 A1 | 12/2008 | Brunner et al. |
| 2009/0076156 A1 | 3/2009 | Husain et al. |
| 2009/0099480 A1 | 4/2009 | Salgo et al. |
| 2009/0142850 A1 | 6/2009 | Meathrel et al. |
| 2009/0226522 A1 | 9/2009 | Howes et al. |
| 2009/0275853 A1 | 11/2009 | Sarkela |
| 2010/0029706 A1 | 2/2010 | Miller et al. |
| 2010/0130566 A1 | 5/2010 | Purpura et al. |
| 2010/0196286 A1 | 8/2010 | Armer et al. |
| 2011/0021588 A1 | 1/2011 | Henwood et al. |
| 2011/0066004 A1 | 3/2011 | Sullivan et al. |
| 2011/0172262 A1 | 7/2011 | Deftereos et al. |
| 2011/0245633 A1 | 10/2011 | Goldberg et al. |
| 2011/0269777 A1 | 11/2011 | Bachurin et al. |
| 2011/0290694 A1 | 12/2011 | Fuisz et al. |
| 2012/0076921 A1 | 3/2012 | Myers et al. |
| 2012/0100278 A1 | 4/2012 | Nowak et al. |
| 2012/0195955 A1 | 8/2012 | Bryson et al. |
| 2012/0309804 A1 | 12/2012 | Horn |
| 2012/0325209 A1 | 12/2012 | Quintin |
| 2012/0328688 A1 | 12/2012 | Fuisz et al. |
| 2013/0072532 A1 | 3/2013 | Henwood et al. |
| 2013/0095156 A1 | 4/2013 | Barnhart et al. |
| 2013/0096172 A1 | 4/2013 | Garcia Da Rocha et al. |
| 2013/0116215 A1 | 5/2013 | Coma et al. |
| 2013/0178465 A1 | 7/2013 | Henwood et al. |
| 2013/0225626 A1 | 8/2013 | Bryson et al. |
| 2014/0010873 A1 | 1/2014 | Tygesen et al. |
| 2014/0163080 A1 | 6/2014 | Horn |
| 2014/0203480 A1 | 7/2014 | Musho et al. |
| 2014/0261990 A1 | 9/2014 | Dadey et al. |
| 2014/0287181 A1 | 9/2014 | Malik et al. |
| 2014/0316217 A1 | 10/2014 | Purdon et al. |
| 2014/0323898 A1 | 10/2014 | Purdon et al. |

(56) References Cited

U.S. PATENT DOCUMENTS

| | | |
|---|---|---|
| 2014/0328898 A1 | 11/2014 | Hood et al. |
| 2014/0377329 A1 | 12/2014 | Bryson et al. |
| 2015/0098980 A1 | 4/2015 | Pongpeerapat et al. |
| 2015/0098981 A1 | 4/2015 | Pongpeerapat et al. |
| 2015/0098982 A1 | 4/2015 | Pongpeerapat et al. |
| 2015/0098983 A1 | 4/2015 | Pongpeerapat et al. |
| 2015/0098997 A1 | 4/2015 | Pongpeerapat et al. |
| 2015/0141772 A1 | 5/2015 | LeBoeuf et al. |
| 2015/0250957 A1 | 9/2015 | Albalat |
| 2015/0258067 A1 | 9/2015 | Kokkonen et al. |
| 2016/0000945 A1 | 1/2016 | Nedergaard et al. |
| 2016/0113885 A1 | 4/2016 | Myers et al. |
| 2016/0151299 A1 | 6/2016 | Bryson et al. |
| 2016/0310441 A1 | 10/2016 | Yamazaki et al. |
| 2016/0324446 A1 | 11/2016 | Prerau et al. |
| 2016/0338972 A1 | 11/2016 | Bryson et al. |
| 2016/0374588 A1 | 12/2016 | Shariff et al. |
| 2017/0087084 A1 | 3/2017 | Musho et al. |
| 2017/0087097 A1 | 3/2017 | Musho et al. |
| 2017/0128358 A1 | 5/2017 | Barnhart et al. |
| 2017/0128421 A1 | 5/2017 | Sura et al. |
| 2017/0165235 A1 | 6/2017 | Roychowdhury et al. |
| 2017/0231556 A1 | 8/2017 | Purdon et al. |
| 2017/0239221 A1 | 8/2017 | Negi et al. |
| 2017/0246108 A1 | 8/2017 | Musho et al. |
| 2017/0252294 A1 | 9/2017 | Musho et al. |
| 2017/0273611 A1 | 9/2017 | Purdon et al. |
| 2017/0274174 A1 | 9/2017 | Purdon et al. |
| 2017/0296482 A1 | 10/2017 | Myers et al. |
| 2018/0055764 A1 | 3/2018 | Henwood et al. |
| 2018/0065767 A1 | 3/2018 | Bogue et al. |
| 2018/0098937 A1 | 4/2018 | Horn |
| 2018/0110897 A1 | 4/2018 | Bush et al. |
| 2018/0117012 A1 | 5/2018 | Shudo et al. |
| 2018/0147201 A1 | 5/2018 | Toledano |
| 2018/0177797 A1 | 6/2018 | Berdahl et al. |
| 2018/0360736 A1 | 12/2018 | Obeid et al. |
| 2019/0183729 A1 | 6/2019 | Sura et al. |
| 2019/0209022 A1 | 7/2019 | Sobol et al. |
| 2019/0216345 A1 | 7/2019 | Scheib |
| 2019/0216389 A1 | 7/2019 | Scheib |
| 2019/0276707 A1 | 9/2019 | Wong et al. |
| 2019/0314274 A1 | 10/2019 | Masto et al. |
| 2019/0365715 A1 | 12/2019 | Nandabalan et al. |
| 2019/0374158 A1 | 12/2019 | Brown et al. |
| 2020/0000708 A1 | 1/2020 | Barnhart et al. |
| 2020/0000717 A1 | 1/2020 | Kakumanu et al. |
| 2020/0069650 A1 | 3/2020 | Korpivaara et al. |
| 2020/0093800 A1 | 3/2020 | Pongpeerapat et al. |
| 2020/0138721 A1 | 5/2020 | Grother et al. |
| 2020/0168340 A1 | 5/2020 | Park et al. |
| 2020/0345635 A1 | 11/2020 | Kakumanu et al. |
| 2021/0077388 A1 | 3/2021 | Kakumanu et al. |
| 2021/0267944 A1 | 9/2021 | Yocca et al. |
| 2022/0031663 A1 | 2/2022 | Nandabalan et al. |
| 2022/0110864 A1 | 4/2022 | Kakumanu et al. |
| 2022/0142918 A1 | 5/2022 | Kakumanu et al. |
| 2022/0160629 A1 | 5/2022 | Kakumanu et al. |
| 2022/0202373 A1 | 6/2022 | Yocca et al. |
| 2022/0226288 A1 | 7/2022 | Adedoyin et al. |
| 2022/0276034 A1 | 9/2022 | Kinney et al. |
| 2022/0395222 A1 | 12/2022 | Yocca et al. |
| 2023/0093109 A1 | 3/2023 | Nandabalan et al. |
| 2023/0118091 A1 | 4/2023 | Kakumanu et al. |
| 2023/0140624 A1 | 5/2023 | Kakumanu et al. |

FOREIGN PATENT DOCUMENTS

| | | |
|---|---|---|
| AU | 2014227693 B2 | 6/2018 |
| CA | 2324967 A1 | 5/2002 |
| CA | 3026783 A1 | 12/2017 |
| CN | 101496801 A | 8/2009 |
| CN | 102657635 A | 9/2012 |
| CN | 103284945 A | 9/2013 |
| CN | 104161760 A | 11/2014 |
| CN | 104784174 A | 7/2015 |
| CN | 105168122 A | 12/2015 |
| CN | 105287519 A | 2/2016 |
| CN | 105534891 A | 5/2016 |
| CN | 106038538 A | 10/2016 |
| CN | 106539778 A | 3/2017 |
| CN | 106727443 A | 5/2017 |
| CN | 106727524 A | 5/2017 |
| CN | 107028880 A | 8/2017 |
| CN | 107137399 A | 9/2017 |
| CN | 107412152 A | 12/2017 |
| CN | 107412204 A | 12/2017 |
| CN | 107693485 A | 2/2018 |
| CN | 108498469 A | 9/2018 |
| CN | 109620802 A | 4/2019 |
| CN | 110893186 A | 3/2020 |
| CN | 111481506 A | 8/2020 |
| CN | 112138250 A | 12/2020 |
| EP | 0681601 B1 | 2/1999 |
| EP | 1549305 B1 | 4/2009 |
| EP | 2243468 A1 | 10/2010 |
| EP | 2252290 A1 | 11/2010 |
| EP | 1695094 B1 | 6/2013 |
| EP | 3326612 A1 | 5/2018 |
| JP | 2009526829 A | 7/2009 |
| JP | 5921928 B2 | 5/2016 |
| JP | 2016154598 A | 9/2016 |
| JP | 2019048091 A | 3/2019 |
| KR | 101859486 B1 | 6/2018 |
| KR | 20190109310 A | 9/2019 |
| RU | 2635532 C1 | 11/2017 |
| SU | 1138164 A1 | 2/1985 |
| WO | WO-9514746 A2 | 6/1995 |
| WO | WO-9830207 A1 | 7/1998 |
| WO | WO-9837111 A1 | 8/1998 |
| WO | WO-9938496 A1 | 8/1999 |
| WO | WO-0044351 A1 | 8/2000 |
| WO | WO-02089794 A1 | 11/2002 |
| WO | WO-2004032913 A1 | 4/2004 |
| WO | WO-2005032519 A1 | 4/2005 |
| WO | WO-2005039499 A2 | 5/2005 |
| WO | WO-2006031209 A1 | 3/2006 |
| WO | WO-2006090371 A2 | 8/2006 |
| WO | WO-2008079721 A1 | 7/2008 |
| WO | WO-2008091588 A1 | 7/2008 |
| WO | WO-2009005771 A1 | 1/2009 |
| WO | WO-2009048606 A1 | 4/2009 |
| WO | WO-2009076165 A1 | 6/2009 |
| WO | WO-2010132882 A2 | 11/2010 |
| WO | WO-2011039686 A1 | 4/2011 |
| WO | WO-2011127586 A1 | 10/2011 |
| WO | WO-2012009144 A2 | 1/2012 |
| WO | WO-2012075373 A2 | 6/2012 |
| WO | WO-2012083269 A1 | 6/2012 |
| WO | WO-2012177326 A1 | 12/2012 |
| WO | WO-2013090278 A2 | 6/2013 |
| WO | WO-2013103378 A1 | 7/2013 |
| WO | WO-2013130577 A2 | 9/2013 |
| WO | WO-2013173317 A1 | 11/2013 |
| WO | WO-2014130777 A1 | 8/2014 |
| WO | WO-2014153489 A1 | 9/2014 |
| WO | WO-2014176444 A1 | 10/2014 |
| WO | WO-2013090278 A3 | 12/2014 |
| WO | WO-2015054058 A1 | 4/2015 |
| WO | WO-2015054059 A2 | 4/2015 |
| WO | WO-2015054061 A1 | 4/2015 |
| WO | WO-2015054063 A1 | 4/2015 |
| WO | WO-2016061413 A1 | 4/2016 |
| WO | WO-2016061554 A1 | 4/2016 |
| WO | WO-2016075365 A1 | 5/2016 |
| WO | WO-2016089997 A1 | 6/2016 |
| WO | WO-2017117627 A1 | 7/2017 |
| WO | WO-2018072015 A1 | 4/2018 |
| WO | WO-2018086498 A1 | 5/2018 |
| WO | WO-2018109272 A1 | 6/2018 |
| WO | WO-2018116202 A1 | 6/2018 |
| WO | WO-2018126182 A1 | 7/2018 |
| WO | WO-2018162845 A1 | 9/2018 |
| WO | WO-2019036253 A1 | 2/2019 |

(56) References Cited

FOREIGN PATENT DOCUMENTS

| | | |
|---|---|---|
| WO | WO-2019070929 A1 | 4/2019 |
| WO | WO-2019158810 A1 | 8/2019 |
| WO | WO-2020006073 A1 | 1/2020 |
| WO | WO-2020006092 A1 | 1/2020 |
| WO | WO-2020006119 A1 | 1/2020 |
| WO | WO-2020259440 A1 | 12/2020 |
| WO | WO-2021016112 A2 | 1/2021 |
| WO | WO-2021055595 A1 | 3/2021 |
| WO | WO-2021163482 A1 | 8/2021 |
| WO | WO-2022076818 A1 | 4/2022 |
| WO | WO-2022147537 A1 | 7/2022 |
| WO | WO-2022183029 A1 | 9/2022 |

OTHER PUBLICATIONS

Abdelaziz, et al., "Effect of intranasal dexmedetomidine or intranasal midazolam on prevention of emergence agitation in pediatric strabismus surgery: A randomized controlled study." Egyptian Journal of Anaesthesia (2016) 32: 285-291.
Abdel-Ghaffar, et al., Dexmedetomidina transmucosa oral para controle da agitaç ão ao despertar em crianç as submetidas a amigdalectomia: ensaio clínico randomizado, Rev Bras Anestesiol., 2019, pp. 469-476.
Abdel-Ghaffar et al., "Oral trans-mucosal dexmedetomidine for controlling of emergence agitation in children undergoing tonsillectomy: a randomized controlled trial," Rev Bras Anestesiol. 2019;69(5):469-476 with English abstract.
Abdelmageed, et al., "Intramuscular dexmedetomidine for prevention of shivering after general anesthesia in patients undergoing arthroscopic anterior cruciate ligament reconstruction." Ain-Shams Journal of Anesthesiology (2014); 7(2): 156-162.
Adami, et al., "Combinations of dexmedetomidine and alfaxalone with butorphanol in cats: application of an innovative stepwise optimization method to identify optimal clinical doses for intramuscular anaesthesia." J Feline Med Surg. (2016); 18 (10): 846-853.
Ahmad, et al., "Effects of Midazolam or Midazolam-Fentanyl on Sedation and Analgesia Produced by Intramuscular Dexmedetomidine in Dogs." Asian Journal of Animal Sciences (2011); 5 (5): 302-316.
Aho, et al., "Intramuscularly administered dexmedetomidine attenuates hemodynamic and stress hormone responses to gynecologic laparoscopy." Anesth Analg. (1992); 75(6): 932-939.
Aich, et al., "A Comparison of Intranasal Dexmedetomidine and Intranasal Midazolam for Premedication in Children Undergoing Elective Surgeries." International Journal of Science and Research (IJSR) (2016); 5 (7): 1730-1737.
Akin, et al., "Dexmedetomidine vs midazolam for premedication of pediatric patients undergoing anesthesia." Pediatric Anesthesia (2012); 22 (9): 871-876.
Albertson et al., "Is It Prime Time for Alpha2-Adrenocepter Agonists in the Treatment of Withdrawal Syndromes?," J. Med. Toxicol. (2014) 10:369-381.
Ali and Abdellatif, "Prevention of sevoflurane related emergence agitation in children undergoing adenotonsillectomy: A comparison of dexmedetomidine and propofol." Saudi J Anaesth. (2013); 7(3): 296-300, 7 pages.
Ambi, et al., "Intranasal dexmedetomidine for paediatric sedation for diagnostic magnetic resonance imaging studies." Indian J Anaesth. (2012); 56(6): 587-588.
Ansah, et al., "Comparison of three doses of dexmedetomidine with medetomidine in cats following intramuscular administration." Veterinary Pharmacology and Therapeutics (1998); 21(5): 380-387.
Antonino and Junior, "Effectiveness of Intramuscular Dexmedetomidine and Methadone in Combination to Intratesticular Lidodaine for Orquiectomy in Dogs—Preliminary Study." Investigao (2017); vol. 16, No. 7. Abstract, 2 pages.
Anttila, et al., "Bioavailability of dexmedetomidine after extravascular doses in healthy subjects." British Journal of Clinical Pharmacology (2003); 56(6): 691-693.
Anusua, et al., "Efficacy of Dexmedetomidine in Reducing Emergence Agitation After Sevoflurane Anaesthesia in Indian Paediatric Population." International Journal of Scientific Research (2015); 4(7): ISSN No. 2277-8179, pp. 458-461.
Anzctr Clinical Trial ID: ACTRN12616001522404, Does ketamine improve the quality of sedation of intranasal dexmedetomidine premedication in children. Fujian Provincial Hospital, Date Registered Nov. 4, 2016, Date Last Updated Jan. 29, 2018, https://www.anzctr.org.au/Trial/Registration/TrialReview.aspx?id=369976, downloaded May 6, 2018, 5 pages.
Assad, et al., "Comparative study between prophylactic single dose of fentanyl and dexmedetomidine in the management of agitation after sevoflurane anesthesia in children." Egyptian Journal of Anaesthesia (2011); 27(1): 31-37.
Aungst, et al., "Comparison of nasal, rectal, buccal, sublingual and intramuscular insulin efficacy and the effects of a bile salt absorption promoter." Journal of Pharmacology and Experimental Therapeutics (1988); 244 (1): 23-27.
Ayeko and Mohamed, "Prevention and treatment of sevoflurane emergence agitation and delirium in children with dexmedetomidine." Saudi J Anaesth. (2014); 8(4): 570-571.
Baddigam et al., "Dexmedetomidine in the Treatment of Withdrawal Syndromes in Cardiothoracic Surgery Patients," J. Intensive Care Med., 2005;20(2):118-123.
Bajwa et al., "Dexmedetomidine: An Adjuvant Making Large Inroads into Clinical Practice," Annals of Medical and Health Sciences Research, Oct.-Dec. 2013, vol. 3, Issue 4, pp. 475-483.
Bakri, et al., "Comparison of dexmedetomidine or ondansetron with haloperidol for treatment of postoperative delirium in trauma patients admitted to intensive care unit: randomized controlled trial." Anaesth Pain & Intensive Care (2015); 19(2): 118-123.
Barends et al., "Intranasal dexmedetomidine in elderly subjects with or without beta blockade: a randomised double-blind single-ascending-dose cohort study," British Journal of Anaesthesia, (2020) 124 (4): 411-419.
Bartlett, et al., Understanding the Oral Mucosal Absorption and Resulting Clinical Pharmacokinetics of Asenapine, AAPS PharmSciTech, Dec. 2012, pp. 1110-1115, vol. 13, No. 4.
Behrle, et al., "Intranasal Dexmedetomidine as a Sedative for Pediatric Procedural Sedation." J Pediatr Pharmacol Ther, 2017, pp. 4-8.
Belgrade et al., "Dexmedetomidine Infusion for the Management of Opioid Induced Hyperalgesia," Pain Medicine, 2010, pp. 1819-1826.
Belkin et al., "Alpha-2 receptor agonists for the treatment of posttraumatic stress disorder," Drugs in Context 2015; 4: 212286, 5 pages.
Bergese et al., "A Phase IIIb, Randomized, Double-blind, Placebo-controlled, Multicenter Study Evaluating the Safety and Efficacy of Dexmedetomidine for Sedation During Awake Fiberoptic Intubation," American Journal of Therapeutics (2010) 17, 586-595.
Bhardwaj, et al., "Abstract PR227: Comparison of Nasal Dexmedetomidine with Oral Midazolam for Premedication in Children Effect on Psychomotor Recovery." Anesthesia & Analgesia (2016); 123 (3S_Suppl): p. 288.
Bhat, et al., "Comparison of intranasal dexmedetomidine and dexmedetomidine-ketamine for premedication in pediatrics patients: A randomized double-blind study." Anesth Essays Res. (2016); 10 (2): 349-355.
Bienvenu et al., "Treatment of four psychiatric emergencies in the intensive care unit," Critical Care Medicine (2012) 40(9):2662-2670.
Biermann, et al., "Sedative, cardiovascular, haematologic and biochemical effects of four different drug combinations administered intramuscularly in cats." Veterinary Anaesthesia and Analgesia (2012); 39 (2): 137-150.
Bioxcel Therapeutics Announces FDA approval of ILGALMI, Press Release, Apr. 6, 2022, 5 pages.
BioXcel Therapeutics, Inc., "BioXcel Therapeutics Announces BXCL501 Program Initiative for Prevention and Treatment of Acute Agitation using Wearable Digital Devices," Sep. 18, 2019, 3 pages, retrieved from: https://www.globenewswire.com/en/news-release/2019/09/18/1917334/0/en/BioXcel-Therapeutics-Announces-

(56) References Cited

OTHER PUBLICATIONS

BXCL501-Program-Initiative-for-Prevention-and-Treatment-of-Acute-Agitation-using-Wearable-Digital-Devices.html.

BioXcel Therapeutics, Inc., "BioXcel Therapeutics Announces First Patient Enrolled in Phase 1b/2 Study of BXCL501 for Acute Treatment of Agitation Associated with Dementia," Jan. 7, 2020, 3 pages, retrieved from https://www.globenewswire.com/news-release/2020/01/07/1967125/0/en/BioXcel-Therapeutics-Announces-First-Patient-Enrolled-in-Phase-1b-2-Study-of-BXCL501-for-Acute-Treatment-of-Agitation-Associated-with-Dementia.html.

BioXcel Therapeutics, Inc., "BioXcel Therapeutics, Inc. (BTAI) CEO Vimal Mehta on Q2 2018 Results—Earnings Call Transcript," Seeking Alpha, Aug. 12, 2018, 13 pages, retrieved from: https://seekingalpha.com/article/4198129-bioxcel-therapeutics-inc-btai-ceo-vimal-mehta-q2-2018-results-earnings-call-transcript?part=single.

BioXcel Therapeutics, Inc., "BioXcel Therapeutics Provides Update on the Clinical Advancement of BXCL501 for the Acute Treatment of Agitation," Globe Newswire, Oct. 30, 2018, 2 pages, retrieved from: https://www.globenewswire.com/news-release/2018/10/30/1638858/0/en/BioXcel-Therapeutics-Provides-Update-on-the-Clinical-Advancement-of-BXCL501-for-the-Acute-Treatment-of-Agitation.html.

BioXcel Therapeutics, Inc., "BioXcel Therapeutics Reports Positive Results from Study in Agitated Schizophrenia Patients Supporting BXCL501 Clinical Development," Globe Newswire, Nov. 14, 2018, 3 pages, retrieved from: https://www.globenewswire.com/news-release/2018/11/14/1651151/0/en/BioXcel-Therapeutics-Reports-Positive-Results-from-Study-in-Agitated-Schizophrenia-Patients-Supporting-BXCL501-Clinical-Development.html.

BioXcel Therapeutics, Inc., "BioXcel Therapeutics Reports Third Quarter 2018 Quarterly Results and Provides Business Update," Globe Newswire, Nov. 9, 2018, 3 pages, retrieved from: https://ir.bioxceltherapeutics.com/press-releases/detail/61/bioxcel-therapeutics-reports-third-quarter-2018-quarterly.

BioXcel Therapeutics, Inc., "BioXcel Therapeutics to Host Second Quarter 2018 Financial Results and Business Update," Globe Newswire, Aug. 2, 2018, 2 pages, retrieved from: https://ir.bioxceltherapeutics.com/press-releases/detail/47/bioxcel-therapeutics-to-host-second-quarter-2018-financial.

BioXcel Therapeutics, Inc., "Next Wave of Medicines Utilizing AI," Jun. 2020, 30 pages, retrieved from https://d1io3yog0oux5.cloudfront.net/_ec77451d0911d660fb193909a0a1ba0e/bioxceltherapeutics/db/445/3421/pdf/BioXcel+Therapeutics+Presentation_June+11.pdf.

BioXcel Therapeutics, Inc., United States Securities and Exchange Commission, Form 10-K, Annual Report Pursuant to Section 13 or 15(d) of the Securities Exchange Act of 1934, For the year ended Dec. 31, 2019, 135 pages.

Bonanno, et al., "Effectiveness of preoperative intranasal dexmedetomidine compared with oral midazolam for the prevention of emergence delirium in pediatric patients undergoing general anesthesia: a systematic review protocol." JBI Database of Systematic Reviews and Implementation Reports: 2016; 14 (8): 70-79.

Bond, et al., "Dexmedetomidine Nasal Sedation Produces More Oculocardiac Reflex During Strabismus Surgery." Journal of Pediatric Ophthalmology and Strabismus (2016); 53 (5): 318.

Boriosi et al., "Safety and Efficacy of Buccal Dexmedetomidine for MRI Sedation in School-Aged Children," Hospital Pediatrics, May 2019, vol. 9, Issue 5, pp. 348-354.

Boyer, Jeanne, "Calming patient agitation with dexmedetomidine." Nursing Critical Care (2010); 5 (1): 30-34.

Bryson E.O., et al., "Treatment-Resistant Postictal Agitation After Electroconvulsive Therapy (ECT) Controlled with Dexmedetomidine," The Journal of ECT, 2013, vol. 29(2), pp. e18.

Candiotti et al., "Monitored Anesthesia Care with Dexmedetomidine: A Prospective, Randomized, Double-Blind, Multicenter Trial," Anesth Analg 2010;110(1):47-56.

Canfrn, et al., "Comparison of sedation scores and propofol induction doses in dogs after intramuscular administration of dexmedetomidine alone or in combination with methadone, midazolam, or methadone plus midazolam." The Veterinary Journal (2016); 210: 56-60.

Carrasco et al., "Dexmedetomidine for the Treatment of Hyperactive Delirium Refractory to Haloperidol in Nonintubated ICU Patients: A Nonrandomized Controlled Trial," Critical Care Medicine, 2016, 44:1295-1306, 12 pages.

Carter, et al., "Onset and quality of sedation after intramuscular administration of dexmedetomidine and hydromorphone in various muscle groups in dogs." Journal of the American Veterinary Medical Association (2013); 243(11): 1569-1572.

Center for Drug Evaluation and Research, Application No. 21-038, Pharmacology Review(s), Drug Name: Precedex (dexmedetomidine hcl injection), Dec. 18, 1998, 184 pages.

Changlu et al., "Determination of Effective Dosage in Intranasal Dexmedetomidine Sedation for MRI Scanning with Modified Dixon's Up-and-Down Method in Children," China Pharmaceuticals, (2015), 24(22), 22-24, with English abstract.

Chao and Zhong, "Effects of preoperative intranasal Dexmedetomidine for the bispectral index and median effective concentration of Sevoflurane in children with abdominal surgery by inhalation anesthesia of Sevoflurane." China Medical Herald Magazine (2017); 14 (34): 66-69, 73 (with English Abstract).

Chen et al., "Dexmedetomidine alleviated isoflurane-induced neurotoxicity in aged rats," Int J Clin Exp Med 2018;11(4):3686-3692.

Chen, et al., "Effect of dexmedetomidine on emergence agitation after oral and maxillofacial surgery." Shanghai Journal of Stomatology (2013); 22(6): 698-701 [with English Abstract/Summary].

Chen et al., "Protective role of dexmedetomidine in unmethylated CpG-induced inflammation responses in BV2 microglia cells," Folia Neuropathol 2016; 54 (4): 382-391.

Cheon and Tkachenko, "Use of dexmedetomidine for prevention of post-operative agitation in a 14 year-old male with Angelman's Syndrome." University of Chicago, Chicago, IL (2014); 1 page.

Cheung, et al., "Analgesic and sedative effects of intranasal dexmedetomidine in third molar surgery under local anaesthesia." British Journal of Anaesthesia (2011); 107 (3): 430-437.

Cheung, et al., "Evaluation of the Analgesic Efficacy of Local Dexmedetomidine Application," Clin J Pain, Jun. 2011, vol. 27, No. 5, pp. 337-382.

Cheung, et al., "Intranasal dexmedetomidine in combination with patient controlled sedation during upper gastrointestinal endoscopy: a randomised trial." Acta Anestheologica Scandinavica, 2015, pp. 215-223.

Chokroverty, S., "Overview of sleep & sleep disorders," Indian J Med Res 131, Feb. 2010, pp. 126-140.

Chowdhury et al., "General intensive care for patients with traumatic brain injury: An update," Saudi Journal of Anaesthesia, 2014, vol. 8, Issue 2, pp. 256-263.

Christiansen, et al., "Sedation of red porgy (Pagrus pagrus) and black sea bass (Centropristis striata) using ketamine (K), dexmedetomidine (D) and midazolam (M) delivered via intramuscular injection." Journal of Zoo and Aquarium Research (2014); 2 (3): 62-68.

Cimen, et al., "Comparison of buccal and nasal dexmedetomidine premedication for pediatric patients." Paediatr Anaesth. (2013); 23(2): 134-138.

Clinical Trial Registration No. ChiCTR-IOR-17012415, "Effect of nasal dexmedetomidine on the prevention of emergence agitation in children undergoing day surgery with desoflurane anesthesia." Guangzhou Women and Children Medical Center, Date of Registration: Aug. 18, 2017, Estimated Trial End Date: Mar. 31, 2018, http://www.chictr.org.cn/showprojen.aspx?proj=21174, downloaded May 5, 2018, 3 pages.

ClinicalTrials.gov Identifier: NCT00417664, Is Dexmedetomidine Associated With a Lower Incidence of Postoperative Delirium When Compared to Propofol or Midazolam in Cardiac Surgery Patients, First Posted—Jan. 4, 2007, Last Update Posted—Jan. 4, 2007, retrieved from https://clinicaltrials.gov/ct2/show/NCT00417664, 5 pages.

ClinicalTrials.gov Identifier: NCT00095251, Mends Study: Trial in Ventilated ICU Patients Comparing an Alpha2 Agonist Versus a Gamma Aminobutyric Acid (GABA)—Agonist to Determine Delirium

(56) References Cited

OTHER PUBLICATIONS

Rates, Efficacy of Sedation, Analgesia and Discharge Cognitive Status, First Posted—Nov. 2, 2004, Last Update Posted—Sep. 11, 2018, retrieved from https://clinicaltrials.gov/ct2/show/NCT00095251, 8 pages.

ClinicalTrials.gov Identifier: NCT00351299, Randomized Controlled Trial of Dexmedetomidine for the Treatment of Intensive Care Unit (ICU) Delirium, Jul. 12, 2006, Last Update Posted—Jun. 9, 2017, retrieved from https://clinicaltrials.gov/ct2/show/NCT00351299, 15 pages.

ClinicalTrials.gov Identifier: NCT00455143, Cognitive Protection—Dexmedetomidine and Cognitive Reserve, First Posted—Apr. 3, 2007, Last Update Posted—Jul. 17, 2019, retrieved from https://clinicaltrials.gov/ct2/show/NCT00455143, 20 pages.

ClinicalTrials.gov Identifier: NCT00460473, A Research Study to Evaluate the Effectiveness of Dexmedetomidine in Preventing Delirium After Hip Fracture Repair Surgery, First Posted—Apr. 16, 2007, Last Update Posted—Jul. 24, 2015, retrieved from https://clinicaltrials.gov/ct2/show/NCT00460473, 7 pages.

ClinicalTrials.gov Identifier: NCT00464763, A Research Study to Evaluate the Effectiveness of Dexmedetomidine in Preventing Delirium After Heart Surgery, First Posted—Apr. 24, 2007, Last Update Posted—Mar. 21, 2017, retrieved from https://clinicaltrials.gov/ct2/show/NCT00460473, 7 pages.

ClinicalTrials.gov Identifier: NCT00468052, Decrease Emergence Agitation and Provide Pain Relief for Children Undergoing Tonsillectomy & Adenoidectomy, First Posted—May 1, 2007, Last Update Posted—Dec. 5, 2016, retrieved from https://clinicaltrials.gov/ct2/show/NCT00468052, 24 pages.

ClinicalTrials.gov Identifier: NCT00505804, A Comparison of Dexmedetomidine and Haloperidol in Patients With Intensive Care Unit (ICU)—Associated Agitation and Delirium (Dex), First Posted—Jul. 25, 2007, Last Update Posted—Jan. 24, 2013, retrieved from https://clinicaltrials.gov/ct2/show/NCT00505804, 6 pages.

ClinicalTrials.gov Identifier: NCT00561678, Perioperative Cognitive Function—Dexmedetomidine and Cognitive Reserve, First Posted—Nov. 21, 2007, Last Update Posted—Apr. 23, 2018, retrieved from https://clinicaltrials.gov/ct2/show/NCT00561678, 23 pages.

ClinicalTrials.gov Identifier: NCT00654329, Dexmedetomidine vs Fentanyl for BMT (DexBMT). Children's Research Institute, First Posted Apr. 8, 2018, Results First Posted Apr. 25, 2011, Last Update Posted Apr. 25, 2011, Study Start Date Aug. 2005, https://clinicaltrials.gov/ct2/show/NCT00654329, downloaded May 5, 2018, 6 pages.

ClinicalTrials.gov Identifier: NCT00778063, Study Using Dexmedetomidine to Decreases Emergence Delirium in Pediatric Patients (PED-DEX). Ochsner Health System, First Posted Oct. 23, 2008, Last Update Posted Mar. 15, 2013, Study Start Date Mar. 2009, https://clinicaltrials.gov/ct2/show/NCT00778063, downloaded May 6, 2018, 8 pages.

ClinicalTrials.gov Identifier: NCT00837187, Bioavailability of Dexmedetomidine After Intranasal Administration (INDEX). University of Turku, First Posted Feb. 5, 2009, Last Update Posted Jan. 13, 2010, Study Start Date Mar. 2009, https://clinicaltrials.gov/ct2/show/NCT00837187, downloaded May 6, 2018, 6 pages.

ClinicalTrials.gov Identifier: NCT00857727, Use of Dexmedetomidine to Reduce Emergence Delirium Incident in Children (DexPeds), First Posted—Mar. 9, 2009, Last Update Posted—Nov. 27, 2018, retrieved from https://clinicaltrials.gov/ct2/show/NCT00857727, 18 pages.

ClinicalTrials.gov Identifier: NCT01065701, Comparison of Two Doses of Intranasal Dexmedetomidine as Premedication in Children. The University of Hong Kong, First Posted Feb. 9, 2010, Last Update Posted Oct. 26, 2017, Study Start Date Jul. 2009, https://clinicaltrials.gov/ct2/show/NCT01065701, downloaded May 6, 2018, 5 pages.

ClinicalTrials.gov Identifier: NCT01132794, A Study to Assess the Analgesia and Sedation Using Intranasal Dexmedetomidine in Third Molar Surgery Under Local Anaesthesia. The University of Hong Kong, First Posted May 28, 2010, Last Update Posted Jun. 16, 2010, https://clinicaltrials.gov/ct2/show/NCT01132794, downloaded May 5, 2018, 6 pages.

ClinicalTrials.gov Identifier: NCT01140529, Dexmedetomidine for the Treatment of Delirium After Heart Surgery (DexinDelir), First Posted—Jun. 9, 2010, Last Update Posted—Nov. 1, 2016, retrieved from https://clinicaltrials.gov/ct2/show/NCT01140529, 5 pages.

ClinicalTrials.gov Identifier: NCT01151865, Dexmedetomidine to Lessen Intensive Care Unit (ICU) Agitation (DahLIA), First Posted—Jun. 29, 2010, Last Update Posted—Jan. 21, 2015, retrieved from https://clinicaltrials.gov/ct2/show/NCT01151865, 9 pages.

ClinicalTrials.gov Identifier: NCT01188551, Dexmedetomidine Versus Fentanyl Following Pressure Equalization Tube Placement. Nationwide Children's Hospital, First Posted Aug. 25, 2010, Last Update Posted Apr. 1, 2014, Study Start Date Jan. 2011, https://clinicaltrials.gov/ct2/show/NCT01188551, downloaded May 5, 2018, 6 pages.

ClinicalTrials.gov Identifier: NCT01255904, A Trial of Oral Chloral Hydrate Versus Intranasal Dexmedetomidine for Sedated Abr Exams. Baylor College of Medicine, First Posted Dec. 8, 2010, Last Update Posted May 16, 2016, Study Start Date Aug. 2011, https://clinicaltrials.gov/ct2/show/NCT01255904, downloaded May 6, 2018, 5 pages.

ClinicalTrials.gov Identifier: NCT01283412, Dexmedetomidine on Postoperative Delirium and Quality of Recovery in Geriatric Patients, First Posted—Jan. 26, 2011, Last Update Posted—Nov. 20, 2013, retrieved from https://clinicaltrials.gov/ct2/show/NCT01283412, 4 pages.

ClinicalTrials.gov Identifier: NCT01353378, Use of Dexmedetomidine in Children Undergoing Oral Maxillofacial Surgery to Decrease Emergence Delirium, First Posted—May 13, 2011, Last Update Posted—May 5, 2017, retrieved from https://clinicaltrials.gov/ct2/show/NCT01353378, 5 pages.

ClinicalTrials.gov Identifier: NCT01362205, Dexmedetomidine (Precedex) for Severe Alcohol Withdrawal Syndrome (AWS) and Alcohol Withdrawal Delirium (AWD), First Posted—May 30, 2011, Last Update Posted—Nov. 6, 2017, retrieved from https://clinicaltrials.gov/ct2/show/NCT01362205, 36 pages.

ClinicalTrials.gov Identifier: NCT01374737, ED50 of Dexmedetomidine to Prevent Emergence Agitation in Children, First Posted—Jun. 16, 2011, Last Update Posted—Jun. 16, 2011, downloaded Feb. 11, 2018 https://clinicaltrials.gov/ct2/show/NCT01374737, 5 pages.

ClinicalTrials.gov Identifier: NCT01378741, Reducing Delirium After Cardiac Surgery: A Multifaceted Approach of Perioperative Care, First Posted—Jun. 22, 2011, Last Update Posted—Apr. 21, 2015, retrieved from https://clinicaltrials.gov/ct2/show/NCT01378741, 5 pages.

ClinicalTrials.gov Identifier: NCT01512355, The Effect of Dexmedetomidine on Decreasing Emergence Agitation and Delirium in Pediatric Patients Undergoing Strabismus Surgery, First Posted—Jan. 19, 2012, Last Update Posted—Jul. 16, 2015, retrieved from https://clinicaltrials.gov/ct2/show/NCT01512355, 5 pages.

ClinicalTrials.gov Identifier: NCT01513772, The Effect of Dexmedetomidine on the Emergence Agitation in Nasal Surgery, First Posted—Jan. 20, 2012, Last Update Posted—Aug. 9, 2012, retrieved from https://clinicaltrials.gov/ct2/show/NCT01513772, 4 pages.

ClinicalTrials.gov Identifier: NCT01517438, Effects of Serotonin Inhibitors on Patient-controlled Analgesia Related Nausea and Vomiting, First Posted—Jan. 25, 2012, Last Update Posted—Jan. 25, 2012, retrieved from https://clinicaltrials.gov/ct2/show/NCT01517438, 4 pages.

ClinicalTrials.gov Identifier: NCT01517932, Effects of Dexmedetomidine on Stress Response and Postoperative Analgesia, First Posted—Jan. 25, 2012, Last Update Posted—Mar. 20, 2013, retrieved from https://clinicaltrials.gov/ct2/show/NCT01517932, 6 pages.

ClinicalTrials.gov Identifier: NCT01524367, Effect of Single-dose Dexmedetomidine on Emergence Excitement in Adults With Nasotracheal Intubation After Orthognathic Surgery, First Posted—Feb. 2, 2012, Last Update Posted—Feb. 6, 2015, retrieved from https://clinicaltrials.gov/ct2/show/NCT01524367, 6 pages.

ClinicalTrials.gov Identifier: NCT01528891, Dexmedetomidine as a Rapid Bolus in Children for Emergence Agitation, First Posted—

(56) References Cited

OTHER PUBLICATIONS

Feb. 8, 2012, Last Update Posted—Jan. 20, 2016, downloaded Feb. 11, 2018 https://clinicaltrials.gov/ct2/show/results/NCT01528891, 6 pages.
ClinicalTrials.gov Identifier: NCT01528891, Dexmedetomidine as a Rapid Bolus in Children for Emergence Agitation, First Posted—Feb. 8, 2012, Last Update Posted—Mar. 8, 2018, retrieved from https://clinicaltrials.gov/ct2/show/results/NCT01528891, 15 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Feb. 17, 2012, Study Start Date—Jun. 2010, Estimated Study Completion Date—Jan. 2013, 9 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Jul. 9, 2018, retrieved from https://clinicaltrials.gov/ct2/show/NCT01535287, 24 pages.
ClinicalTrials.gov Identifier: NCT01578161, The Effect of Dexmedetomidine on Emergence Agitation in Children Undergoing a Surgery Under Desflurane Anesthesia, First Posted—Apr. 16, 2012, Last Update Posted—Apr. 16, 2012, downloaded Feb. 11, 2018 https://clinicaltrials.gov/ct2/show/NCT01578161, 6 pages.
ClinicalTrials.gov Identifier: NCT01691001, Effect of Dexmedetomidine on Sevoflurane Requirements and Emergence Agitation in Children Undergoing Ambulatory Surgery, First Posted—Sep. 24, 2012, Last Update Posted—Sep. 24, 2012, retrieved from https://clinicaltrials.gov/ct2/show/NCT01691001, 4 pages.
ClinicalTrials.gov Identifier: NCT01739933, The MENDS2 Study, Maximizing the Efficacy of Sedation and Reducing Neurological Dysfunction and Mortality in Septic Patients With Acute Respiratory Failure (MENDS2), First Posted—Dec. 4, 2012, Last Update Posted—Apr. 5, 2019, retrieved from https://clinicaltrials.gov/ct2/show/NCT01739933, 11 pages.
ClinicalTrials.gov Identifier: NCT01791296, Does Nightly Dexmedetomidine Improve Sleep and Reduce Delirium in ICU Patients? (SKY-DEX), First Posted—Feb. 13, 2013, Last Update Posted—Mar. 17, 2017, retrieved from https://clinicaltrials.gov/ct2/show/NCT01791296, 8 pages.
ClinicalTrials.gov Identifier: NCT01887184, Sedation Using Intranasal Dexmedetomidine in Upper Gastrointestinal Endoscopy. The University of Hong Kong, First Posted Jun. 26, 2013, Last Update Posted Oct. 28, 2014, Study Start Date Jan. 2009, https://clinicaltrials.gov/ct2/show/NCT01887184, downloaded May 5, 2018, 7 pages.
ClinicalTrials.gov Identifier: NCT01895023, Effects of Dexmedetomidine Premedication on Emergence Agitation After Strabismus Surgery in Children. Yao Yusheng, First Posted Jul. 10, 2013, Last Update Posted Jan. 6, 2015, Study Start Date Sep. 2013, https://clinicaltrials.gov/ct2/show/NCT01895023, downloaded May 5, 2018, 7 pages.
ClinicalTrials.gov Identifier: NCT01900405, Intranasal Dexmedetomidine Sedation for Pediatric CT Imaging. University of Sao Paulo, First Posted Jul. 16, 2013, Last Update Posted Jul. 16, 2013, Study Start Date Apr. 2013, downloaded https://clinicaltrials.gov/ct2/show/NCT01900405, downloaded May 6, 2018, 7 pages.
ClinicalTrials.gov Identifier: NCT01901588, Efficacy of Single-Shot Dexmedetomidine Versus Placebo in Preventing Pediatric Emergence Delirium in Strabismus Surgery, First Posted—Mar. 8, 2016, Last Update Posted—Last Update Posted—Jul. 11, 2016, retrieved from https://clinicaltrials.gov/ct2/show/NCT01901588, 5 pages.
ClinicalTrials.gov Identifier: NCT01904760, Dexmedetomidine to Prevent Agitation After Free Flap Surgery, First Posted—Jul. 22, 2013, Last Update Posted—Nov. 13, 2014, retrieved from https://clinicaltrials.gov/ct2/show/NCT01904760, 6 pages.
ClinicalTrials.gov Identifier: NCT01934049, Postoperative Recovery in Elderly Patients Undergoing Hip Hemi-arthroplasty, First Posted—Sep. 4, 2013, Last Update Posted—Sep. 10, 2013, retrieved from https://clinicaltrials.gov/ct2/show/NCT01934049, 7 pages.
ClinicalTrials.gov Identifier: NCT01937611, Intramuscular Dexmedetomidine as Premedication. First Posted—Sep. 9, 2013, Last Update Posted—Sep. 9, 2013, Study Start Date—Mar. 2013, Estimated Study Completion Date—Oct. 2013, 8 pages.
ClinicalTrials.gov Identifier: NCT01966315, The Comparison of Dexmedetomidine and Midazolam for the Sleep in Intensive Care Unit, First Posted—Oct. 21, 2013, Last Update Posted—Apr. 23, 2019, retrieved from https://clinicaltrials.gov/ct2/show/NCT01966315, 5 pages.
ClinicalTrials.gov Identifier: NCT02007798, Small-dose Dexmedetomidine Effects on Recovery Profiles of Supratentorial Tumors Patients From General Anesthesia, First Posted—Dec. 11, 2013, Last Update Posted—Jan. 14, 2014, retrieved from https://clinicaltrials.gov/ct2/show/NCT02007798, 8 pages.
ClinicalTrials.gov Identifier: NCT02072083, Intranasal Dexmedetomidine vs Midazolam-ketamine Combination for Premedication of Pediatric Patients. TC Erciyes University, First Posted Feb. 26, 2014, Last Update Posted Apr. 14, 2015, Study Start Date Feb. 2014, https://clinicaltrials.gov/ct2/show/NCT02072083, downloaded May 5, 2018, 6 pages.
ClinicalTrials.gov Identifier: NCT02077712, Intranasal Dexmedetomidine Sedation for Ophthalmic Examinations in Children (DEX-EYE). Sun Yat-sen University, First Posted Mar. 4, 2014, Last Update Posted May 3, 2016, Study Start Date Feb. 2014, https://clinicaltrials.gov/ct2/show/NCT02077712, downloaded May 5, 2018, 7 pages.
ClinicalTrials.gov Identifier: NCT02080169, Safety and Efficacy of Combined Sedation With Midazolam and Dexmedetomidine in ICU Patients, First Posted—Mar. 6, 2014, Last Update Posted—Mar. 6, 2014, retrieved from https://clinicaltrials.gov/ct2/show/NCT02080169, 8 pages.
ClinicalTrials.gov Identifier: NCT02096068, Neuroprotection With Dexmedetomidine in Patients Undergoing Elective Cardiac or Abdominal Surgery (Neuprodex), First Posted—Mar. 26, 2014, Last Update Posted—Aug. 22, 2018, retrieved from https://clinicaltrials.gov/ct2/show/NCT02096068, 9 pages.
ClinicalTrials.gov Identifier: NCT02104297, Effect of Deksmedetomidine and Remifentanil in Extubation Agitation (EA), First Posted—Apr. 4, 2014, Last Update Posted—Apr. 4, 2014, retrieved from https://clinicaltrials.gov/ct2/show/NCT02104297, 5 pages.
ClinicalTrials.gov Identifier: NCT02108171, Intranasal Dexmedetomidine Premedication. Guangzhou First People's Hospital, First Posted Apr. 9, 2014, Last Update Posted Mar. 14, 2016, Study Start Date Mar. 2014, https://clinicaltrials.gov/ct2/show/NCT02108171, downloaded May 5, 2018, 24 pages.
ClinicalTrials.gov Identifier: NCT02117726, Impact of Various Sedation Regimens on the Incidence of Delirium, First Posted—Apr. 21, 2014, Last Update Posted—Jul. 16, 2014, retrieved from https://clinicaltrials.gov/ct2/show/NCT02117726, 7 pages.
ClinicalTrials.gov Identifier: NCT02168439, Intranasal Dexmedetomidine vs Intranasal Midazolam as Anxiolysis Prior to Pediatric Laceration Repair. University of Pittsburgh, Results First Posted Mar. 10, 2017, Last Update Posted Mar. 10, 2017, Study Start Date Jun. 2014, https://clinicaltrials.gov/ct2/show/NCT02168439, downloaded May 6, 2018, 6 pages.
ClinicalTrials.gov Identifier: NCT02169336, Placebo-Controlled Evaluation of Intranasal Dexmedetomidine for Postoperative Analgesia Following Bunionectomy. Recro Pharma, Inc., First Posted Jun. 23, 2014, Last Update Posted Dec. 10, 2015, Study Start Date Jun. 2014, https://clinicaltrials.gov/ct2/show/NCT02169336, downloaded May 6, 2018, 7 pages.
ClinicalTrials.gov Identifier: NCT02169843, Minimizing ICU Neurological Dysfunction With Dexmedetomidine-induced Sleep (MINDDS), First Posted—Jun. 23, 2014, Last Update Posted—Jun. 23, 2014, retrieved from https://clinicaltrials.gov/ct2/show/NCT02169843, 6 pages.
ClinicalTrials.gov Identifier: NCT02211118, Sedation and Physiological Effects of Intranasal Dexmedetomidine in Severe COPD. Dayton VA Medical Center, First Posted Aug. 7, 2014, Last Update

(56) References Cited

OTHER PUBLICATIONS

Posted Feb. 8, 2017, Study Start Date Oct. 2014, https://clinicaltrials.gov/ct2/show/NCT02211118, 6 pages.
ClinicalTrials.gov Identifier: NCT02222636, The Clinical Research of Intranasal Dexmedetomidine Used in Plastic Surgery of Children. Xijing Hospital, First Posted Aug. 21, 2014, Last Update Posted Aug. 21, 2014, Study Start Date Sep. 2014, https://clinicaltrials.gov/ct2/show/NCT02222636, downloaded May 6, 2018, 6 pages.
ClinicalTrials.gov Identifier: NCT02225210, Effects of Dexmedetomidine Sedation on Delirium and Haemodynamic in Mechanical Ventilated Elderly Patients, First Posted—Aug. 26, 2014, Last Update Posted—Aug. 26, 2014, retrieved from https://clinicaltrials.gov/ct2/show/NCT02225210, 6 pages.
ClinicalTrials.gov Identifier: NCT02239445, Intranasal Dexmedetomidine VS Oral Chloral Hydrate for Rescue Sedation During Magnetic Resonance Imaging. Guangzhou Women and Children's Medical Center, First Posted Sep. 12, 2014, Last Update Posted May 12, 2015, Study Start Date Sep. 2014, https://clinicaltrials.gov/ct2/show/NCT02239445, downloaded May 6, 2018, 7 pages.
ClinicalTrials.gov Identifier: NCT02245256, Efficacy of Low-dose Dexmedetomidine to Prevent Delirium in Liver Transplant Patients, First Posted—Sep. 19, 2014, Last Update Posted—Jan. 25, 2018, retrieved from https://clinicaltrials.gov/ct2/show/NCT02245256, 5 pages.
ClinicalTrials.gov Identifier: NCT02250703, Intranasal Dexmedetomidine Premedication in Children. Results First Posted Jul. 7, 2017, Last Update Posted Jul. 7, 2017, Study Start Date Sep. 2014, downloaded https://clinicaltrials.gov/ct2/show/NCT02250703, downloaded May 6, 2018, 8 pages.
ClinicalTrials.gov Identifier: NCT02253199, The Effect of Age on the Median Effective Dose (ED50) of Intranasal Dexmedetomidine for Rescue Sedation Following Failed Sedation With Oral Chloral Hydrate During Magnetic Resonance Imaging. Guangzhou Women and Children's Medical Center, First Posted Oct. 1, 2014, Last Update Posted Mar. 29, 2016, Study Start Date Oct. 2014, https://clinicaltrials.gov/ct2/show/NCT02253199, downloaded May 5, 2018, 7 pages.
ClinicalTrials.gov Identifier: NCT02267538, Dexmedetomidine and Delirium in Patients After Cardiac Surgery, First Posted—Feb. 2, 2018, Last Update Posted—Mar. 5, 2018, retrieved from https://clinicaltrials.gov/ct2/show/NCT02267538, 12 pages.
ClinicalTrials.gov Identifier: NCT02275182, Impact of Dexmedetomidine on the Post-Operative Cognition Dysfunction(POCD) in Geriatric Patients, First Posted—Oct. 27, 2014, Last Update Posted—Apr. 25, 2018, retrieved from https://clinicaltrials.gov/ct2/show/NCT02275182, 8 pages.
ClinicalTrials.gov Identifier: NCT02284243, Placebo-Controlled Evaluation of Intranasal Dexmedetomidine for Postoperative Analgesia Following Bunionectomy Surgery. Recro Pharma, Inc., First Posted Nov. 5, 2014, Last Update Posted May 2, 2017, Study Start Date Oct. 2014, https://clinicaltrials.gov/ct2/show/NCT02284243, downloaded May 6, 2018, 8 pages.
ClinicalTrials.gov Identifier: NCT02299232, Dexmedetomidine in Children for Magnetic Resonance Imaging (MRI) Sedation (DEX). Sisli Hamidiye Etfal Training and Research Hospital, First Posted Nov. 24, 2014, Last Update Posted Oct. 25, 2017, Study Start Date Feb. 2014, https://clinicaltrials.gov/ct2/show/NCT02299232, downloaded May 6, 2018, 6 pages.
ClinicalTrials.gov Identifier: NCT02366299, Comparison of Dexmedetomidine and Propofol on the Delirium and Neuroinflammation in Patients With SIRS, First Posted—Feb. 19, 2015, Last Update Posted—Feb. 19, 2015, retrieved from https://clinicaltrials.gov/ct2/show/NCT02366299, 4 pages.
ClinicalTrials.gov Identifier: NCT02394418, Effect of Sevoflurane, Propofol and Dexmedetomidine on Delirium & Neuroinflammation in Mechanically Ventilated Patients, First Posted—Mar. 20, 2015, Last Update Posted—Jul. 5, 2017, retrieved from https://clinicaltrials.gov/ct2/show/NCT02394418, 5 pages.
ClinicalTrials.gov Identifier: NCT02412150, Effect of Dexmedetomidine After Thyroidectomy, First Posted—Apr. 9, 2015, Last Update Posted—Mar. 6, 2019, retrieved from https://clinicaltrials.gov/ct2/show/NCT02412150, 4 pages.
ClinicalTrials.gov Identifier: NCT02459509, A Comparison of Two Doses of Intranasal Dexmedetomidine for Premedication in Children. The University of Hong Kong, First Posted Jun. 2, 2015, Last Update Posted Apr. 18, 2016, Study Start Date Jun. 2015, https://clinicaltrials.gov/ct2/show/NCT02459509, downloaded May 6, 2018, 8 pages.
ClinicalTrials.gov Identifier: NCT02509949, Effects of Dexmedetomidine on Delirium After Living Donor Renal Transplantation in Adult Patients, First Posted—Jul. 28, 2015, Last Update Posted—Jun. 12, 2018, retrieved from https://clinicaltrials.gov/ct2/show/NCT02509949, 4 pages.
ClinicalTrials.gov Identifier: NCT02528513, Midazolam Used Alone or Sequential Use of Midazolam and Propofol/Dexmedetomidine in Mechanically Ventilated Patients, First Posted—Aug. 19, 2015, Last Update Posted—Apr. 28, 2016, retrieved from https://clinicaltrials.gov/ct2/show/NCT02528513, 9 pages.
ClinicalTrials.gov Identifier: NCT02544906, Propofol Versus Dexmedetomidine for Prevention of Sevoflurane Agitation in Recipients of Living Donor Liver Transplantation (Agitation), First Posted—Sep. 9, 2015, Last Update Posted—Sep. 9, 2015, retrieved from https://clinicaltrials.gov/ct2/show/NCT02544906, 4 pages.
ClinicalTrials.gov Identifier: NCT02546765, Dexmedetomidine and IV Acetaminophen for the Prevention of Postoperative Delirium Following Cardiac Surgery (DEXACET), First Posted—Sep. 11, 2015, Last Update Posted—Aug. 1, 2018, retrieved from https://clinicaltrials.gov/ct2/show/NCT02546765, 9 pages.
ClinicalTrials.gov Identifier: NCT02546765, Dexmedetomidine Versus Propofol for Prolonged Sedation in Critically III Trauma and Surgical Patients, First Posted—Sep. 14, 2015, Last Update Posted—Sep. 14, 2015, retrieved from https://clinicaltrials.gov/ct2/show/NCT02548923, 5 pages.
ClinicalTrials.gov Identifier: NCT02573558, Intraoperative Sedation and Postoperative Delirium, First Posted—Oct. 12, 2015, Last Update Posted—Apr. 6, 2016, retrieved from https://clinicaltrials.gov/ct2/show/NCT02573558, 5 pages.
ClinicalTrials.gov Identifier: NCT02675049, Efficacy and Optimal Dose Selection of Intranasal Dexmedetomidine During Breast Lumpectomy Under Local Anaesthesia. Tianjin Medical University Cancer Institute and Hospital, First Posted Feb. 5, 2016, Last Update Posted Mar. 1, 2016, Study Start Date Jan. 2016, https://clinicaltrials.gov/ct2/show/NCT02675049, downloaded May 5, 2018, 6 pages.
ClinicalTrials.gov Identifier: NCT02699801, Dexmedetomidine Use in ICU Sedation and Postoperative Recovery in Elderly Patients and Post-cardiac Surgery (DIRECT), First Posted—Mar. 4, 2016, Last Update Posted—Nov. 3, 2016, retrieved from https://clinicaltrials.gov/ct2/show/NCT02699801, 8 pages.
ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Dec. 27, 2017, downloaded Feb. 11, 2018 https://clinicaltrials.gov/ct2/show/NCT02720705, 7 pages.
ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Nov. 1, 2018, retrieved from https://clinicaltrials.gov/ct2/show/NCT02720705, 6 pages.
ClinicalTrials.gov Identifier: NCT02757495, Can Caudal Dexmedetomidine Prevents Sevoflurane Induced Emergence Agitation in Children, First Posted—May 2, 2016, Last Update Posted—Feb. 27, 2019, retrieved from https://clinicaltrials.gov/ct2/show/NCT02757495, 6 pages.
ClinicalTrials.gov Identifier: NCT02773797, Placebo Controlled Evaluation of Sedation and Physiological Response to Intranasal Dexmedetomidine in Severe COPD. Dayton VA Medical Center, First Posted May 16, 2016, 7 pages, Last Update Posted May 16, 2016, Study Start Date Aug. 2016, https://clinicaltrials.gov/ct2/show/NCT02773797.

(56) References Cited

OTHER PUBLICATIONS

ClinicalTrials.gov Identifier: NCT02780427, ED50 and ED95 of Intranasal Dexmedetomidine in Pediatric Patients Undergoing Transthoracic Echocardiography Study. Guangzhou Women and Children's Medical Center, First Posted May 23, 2016, Last Update Posted Nov. 21, 2017, Study Start Date Jun. 2016, https://clinicaltrials.gov/ct2/show/NCT02780427, downloaded May 6, 2018, 8 pages.
ClinicalTrials.gov Identifier: NCT02793986, Dexmedetomidine vs Propofol Sedation Reduces Postoperative Delirium in Patients Receiving Hip Arthroplasty, First Posted—Jun. 8, 2016, Last Update Posted—Jun. 29, 2017, retrieved from https://clinicaltrials.gov/ct2/show/NCT02793986, 6 pages.
ClinicalTrials.gov Identifier: NCT02809937, Dexmedetomidine and Long-term Outcome in Elderly Patients After Surgery, First Posted—Jun. 22, 2016, Last Update Posted—Jun. 16, 2017, retrieved from https://clinicaltrials.gov/ct2/show/NCT02809937, 10 pages.
ClinicalTrials.gov Identifier: NCT02818569, Repurposing Dexmedetomidine as an Orally Administered Sleep Therapeutic, First Posted—Jun. 29, 2016, Last Update Posted—Aug. 17, 2018, retrieved from https://clinicaltrials.gov/ct2/show/NCT02818569, 5 pages.
ClinicalTrials.gov Identifier: NCT02836431, Pharmacokinetic Study of Dexmedetomidine After Intra-nasal Dosing in Children. Children's Hospital Medical Center, First Posted Jul. 19, 2016, Last Update Posted Aug. 1, 2017, Study Start Date Jan. 2016, https://clinicaltrials.gov/ct2/show/NCT02836431, downloaded May 6, 2018, 8 pages.
ClinicalTrials.gov Identifier: NCT02856594, Minimizing ICU Neurological Dysfunction With Dexmedetomidine-induced Sleep (MINDDS), First Posted—Aug. 5, 2016, Last Update Posted—Jan. 8, 2019, retrieved from https://clinicaltrials.gov/ct2/show/NCT02856594, 6 pages.
ClinicalTrials.gov Identifier: NCT02903407, Pain, Agitation and Delirium (PAD) Protocol in the Duke CICU, First Posted—Sep. 16, 2016, Last Update Posted—Oct. 18, 2018, retrieved from https://clinicaltrials.gov/ct2/show/NCT02903407, 9 pages.
ClinicalTrials.gov Identifier: NCT02917018, Effect of Dexmedetomidine on Stress Response and Emergence Agitation During Laparoscopic Surgery, First Posted—Sep. 28, 2016, Last Update Posted—Jan. 4, 2017, downloaded Feb. 11, 2018 https://clinicaltrials.gov/ct2/show/NCT02917018, 6 pages.
ClinicalTrials.gov Identifier: NCT02923128, Whether Dexmedetomidine Can Improve the Prognosis of Elderly Patients With Postoperative Cognitive Dysfunction, First Posted—Oct. 4, 2016, Last Update Posted—Oct. 11, 2016, retrieved from https://clinicaltrials.gov/ct2/show/NCT02923128, 7 pages.
ClinicalTrials.gov Identifier: NCT02951793, Abuse and Addiction in ICU, First Posted—Nov. 1, 2016, Last Update Posted—May 19, 2017, retrieved from https://clinicaltrials.gov/ct2/show/NCT02951793, 7 pages.
ClinicalTrials.gov Identifier: NCT02955732, Pharmacological Characteristics of Intranasally Given Dexmedetomidine in Paediatric Patients (PINDEX). Turku University Hospital, First Posted Nov. 4, 2016, Last Update Posted Dec. 14, 2017, Study Start Date Jan. 1, 2017, https://clinicaltrials.gov/ct2/show/NCT02955732, downloaded May 6, 2018, 6 pages.
ClinicalTrials.gov Identifier: NCT02985697, Safety and Efficacy of Intranasal Dexmedetomidine. Bon Secours Pediatric Dental Associates, First Posted Dec. 7, 2016, Last Update Posted Dec. 7, 2016, Study Start Date Jan. 2017, https://clinicaltrials.gov/ct2/show/NCT02985697, downloaded May 6, 2018, 8 pages.
ClinicalTrials.gov Identifier: NCT03012984, Dexmedetomidine Supplemented Analgesia and Incidence of Postoperative Delirium, First Posted—Jan. 6, 2017, Last Update Posted—Jul. 31, 2018, retrieved from https://clinicaltrials.gov/ct2/show/NCT03012984, 13 pages.
ClinicalTrials.gov Identifier: NCT03069638, Intranasal Dexmedetomidine Sedation During Intraarticular Joint Injections in Pediatric Population, First Posted—Mar. 3, 2017, Last Update Posted—May 12, 2021, retrieved from https://clinicaltrials.gov/ct2/show/NCT03069638, 8 pages.

ClinicalTrials.gov Identifier: NCT03069638, Intranasal Dexmedetomidine Sedation During Intra-articular Joint Injections in Pediatric Population. University of Oulu, First Posted Mar. 3, 2017, Last Update Posted Mar. 15, 2018, Actual Study Start Date Feb. 1, 2017, https://clinicaltrials.gov/ct2/show/NCT03069638, downloaded May 6, 2018, 7 pages.
ClinicalTrials.gov Identifier: NCT03078946, Dexmedetomidine Versus Morphine and Midazolam in Prevention and Treatment of Delirium After Adult Cardiac Surgery, First Posted—Mar. 14, 2017, Last Update Posted—Mar. 14, 2017, retrieved from https://clinicaltrials.gov/ct2/show/NCT03078946, 6 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Apr. 19, 2017, downloaded Feb. 11, 2018 https://clinicaltrials.gov/ct2/show/NCT03120247, 7 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Oct. 2, 2018, retrieved from https://clinicaltrials.gov/ct2/show/NCT03120247, 6 pages.
ClinicalTrials.gov Identifier: NCT03120442, Postoperative Delirium After Total Knee Arthroplasty Under Regional Anesthesia, First Posted—Apr. 19, 2017, Last Update Posted—Mar. 26, 2019, retrieved from https://clinicaltrials.gov/ct2/show/NCT03120442, 12 pages.
ClinicalTrials.gov Identifier: NCT03131375, Dexmedetomidine Reduces Emergence Delirium in Children Undergoing Tonsillectomy With Propofol Anesthesia, First Posted—Apr. 27, 2017, Last Update Posted—Jul. 9, 2018, retrieved from https://clinicaltrials.gov/ct2/show/NCT03131375, 7 pages.
ClinicalTrials.gov Identifier: NCT03151863, Intranasal Dexmedetomidine for Procedural Pain Management in Elderly Adults in Palliative Care (INDEX). Walid Habre, First Posted May 12, 2017, Last Update Posted May 16, 2017, Estimated Study Start Date Jul. 1, 2017, https://clinicaltrials.gov/ct2/show/NCT03151863, downloaded May 5, 2018, 9 pages.
ClinicalTrials.gov Identifier: NCT03171740, Premedication With Intranasal Dexmedetomidine or Midazolam for Prevention of Emergence Agitation in Children. Brasilia University Hospital, First Posted May 31, 2017, Last Update Posted Sep. 13, 2017, Study Start Date Jun. 1, 2017, https://clinicaltrials.gov/ct2/show/NCT03171740, downloaded May 5, 2018, 8 pages.
ClinicalTrials.gov Identifier: NCT03171740, Premedication With Intranasal Dexmedetomidine or Midazolam for Prevention of Emergence Agitation in Children, First Posted—May 31, 2017, Last Update Posted—Jul. 13, 2018, retrieved from https://clinicaltrials.gov/ct2/show/NCT03171740, 7 pages.
ClinicalTrials.gov Identifier: NCT03172897, Low-dose Dexmedetomidine in Mechanically Ventilated ICU Patients, First Posted—Jun. 1, 2017, Last Update Posted—Jun. 21, 2019, retrieved from https://clinicaltrials.gov/ct2/show/NCT03172897, 10 pages.
ClinicalTrials.gov Identifier: NCT03174678, Dexmedetomidine Premedication in Children, First Posted—Jun. 2, 2017, Last Update Posted—Jun. 2, 2017, retrieved from https://clinicaltrials.gov/ct2/show/NCT03174678, 6 pages.
ClinicalTrials.gov Identifier: NCT03220880, Intranasal Dexmedetomidine Sedation in Children for Non-painful Procedures. Columbia University, First Posted Jul. 18, 2017, Last Update Posted Apr. 10, 2018, Study Start Date Nov. 1, 2018, https://clinicaltrials.gov/ct2/show/NCT03220880, downloaded May 5, 2018, 9 pages.
ClinicalTrials.gov Identifier: NCT03251222, Intranasal Sedation With Dexmedetomidine. University Medical Centre Ljubljana, First Posted Aug. 16, 2017, Last Update Posted Aug. 16, 2017, Actual Study Start Date Jan. 1, 2017, https://clinicaltrials.gov/ct2/show/NCT03251222, downloaded May 6, 2018, 8 pages.
ClinicalTrials.gov Identifier: NCT03251651, Intraoperative Sedatives and Postoperative Delirium, First Posted—Aug. 16, 2017, Last Update Posted—Apr. 24, 2018, retrieved from https://clinicaltrials.gov/ct2/show/NCT03251651, 6 pages.
ClinicalTrials.gov Identifier: NCT03262090, Effect of Dexmedetomidine on the Prevention of Emergence Agitation in Children Undergoing

(56) References Cited

OTHER PUBLICATIONS

Day Surgery, First Posted—Aug. 25, 2017, Last Update Posted—Jun. 25, 2019, retrieved from https://clinicaltrials.gov/ct2/show/NCT03262090, 6 pages.

ClinicalTrials.gov Identifier: NCT03290625, Intranasal Sedation With Dexmedetomidine and Ketamine in Pediatric Dentistry (NASO II). Universidade Federal de Goias, First Posted Sep. 25, 2017, Last Update Posted Feb. 20, 2018, Actual Study Start Date Nov. 9, 2017, https://clinicaltrials.gov/ct2/show/NCT03290625, downloaded May 6, 2018, 10 pages.

ClinicalTrials.gov Identifier: NCT03293277, Safety, Pharmacokinetics and Pharmacodynamics of Intranasal Dexmedetomidine in Healthy Subjects. Jiangsu HengRui Medicine Co., Ltd., First Posted Sep. 26, 2017, Last Update Posted Jan. 23, 2018, Study Start Date Jul. 26, 2017, https://clinicaltrials.gov/ct2/show/NCT03293277, downloaded May 5, 2018, 7 pages.

ClinicalTrials.gov Identifier: NCT03293927, Polypharmacy-related Adverse Events in Critically Ill Children, First Posted—Sep. 26, 2017, Last Update Posted—Jul. 18, 2019, retrieved from https://clinicaltrials.gov/ct2/show/NCT03293927, 5 pages.

ClinicalTrials.gov Identifier: NCT03317067, Effects of Dexmedetomidine on Delirium Duration of Non-intubated ICU Patients (4D Trial) (4D), First Posted—Oct. 23, 2017, Last Update Posted—Feb. 4, 2019, retrieved from https://clinicaltrials.gov/ct2/show/NCT03317067, 7 pages.

ClinicalTrials.gov Identifier: NCT03323593, Pharmacokinetics of Different Mode Administration of Intranasal Dexmedetomidine. The University of Hong Kong, First Posted Oct. 27, 2017, Last Update Posted Oct. 27, 2017, Study Start Date May 2013, https://clinicaltrials.gov/ct2/show/NCT03323593, downloaded May 6, 2018, 5 pages.

ClinicalTrials.gov Identifier: NCT03337672, Comparison of Dexmedetomidine and Midazolam for Prevention of Emergence Delirium in Children, First Posted—Nov. 9, 2017, Last Update Posted—Jan. 9, 2019, retrieved from https://clinicaltrials.gov/ct2/show/NCT03337672, 6 pages.

ClinicalTrials.gov Identifier: NCT03346226, How Different Sedatives Affect Hip Fracture Patient's Postoperative Delirium, First Posted—Nov. 17, 2017, Last Update Posted—Dec. 13, 2017, retrieved from https://clinicaltrials.gov/ct2/show/NCT03346226, 9 pages.

ClinicalTrials.gov Identifier: NCT03394430, Comparison of Midazolam or Dexmedetomidine on Epileptiform EEG During Sevoflurane Mask Induction. First Posted Jan. 9, 2018, Last Update Posted Feb. 13, 2018, Estimated Study Start Date Apr. 1, 2018, https://clinicaltrials.gov/ct2/show/NCT03394430, downloaded May 5, 2018, 8 pages.

ClinicalTrials.gov Identifier: NCT03399838, Comparing in Dexmedetomidine With po/pr Midazolam for Procedural Sedation in the Pediatric Emergency Department (PedINDEX). University Hospital Inselspital, Berne, First Posted Jan. 16, 2018, Last Update Posted Jan. 16, 2018, https://clinicaltrials.gov/ct2/show/NCT03399838, downloaded May 6, 2018, 6 pages.

ClinicalTrials.gov Identifier: NCT03417999, Pharmacokinetic Study of Intranasal Dexmedetomidine in Pediatric Patients With Congenital Heart Disease. Children's Hospital of Philadelphia, First Posted Jan. 31, 2018, Last Update Posted Apr. 12, 2018, Estimated Study Start Date May 2018, https://clinicaltrials.gov/ct2/show/NCT03417999, downloaded May 6, 2018, 7 pages.

ClinicalTrials.gov Identifier: NCT03477994, Efficacy of Dexmedetomidine Versus Clonidine to Control Delirium in Patients Undergoing CABG, First Posted—Mar. 27, 2018, Last Update Posted—Jul. 11, 2019, retrieved from https://clinicaltrials.gov/ct2/show/NCT03477994, 6 pages.

ClinicalTrials.gov Identifier: NCT03596775, Effect of Dexmedetomidine on Emergence Agitation and Postoperative Behavior Changes in Children, First Posted—Jul. 24, 2018, Last Update Posted—Sep. 7, 2018, retrieved from https://clinicaltrials.gov/ct2/show/NCT03596775?cond=Dexmedetomidine&sfpd_s=07%2F14%2F2018&sfpd_e=11%2F20%2F2018&rank=29, 7 pages.

ClinicalTrials.gov Identifier: NCT03600727, Propofol and Dexmedetomidine on Inflammation, First Posted—Jul. 26, 2018, Last Update Posted—Jul. 26, 2018, retrieved from https://clinicaltrials.gov/ct2/show/NCT03600727?cond=Dexmedetomidine&sfpd_s=07%2F14%2F2018&sfpd_e=11%2F20%2F2018&rank=21, 6 pages.

ClinicalTrials.gov Identifier: NCT03624595, Low-dose Dexmedetomidine and Postoperative Delirium After Cardiac Surgery, First Posted—Aug. 10, 2018, Last Update Posted—Apr. 24, 2019, retrieved from https://clinicaltrials.gov/ct2/show/NCT03624595?cond=Dexmedetomidine&sfpd_s=07%2F14%2F2018&sfpd_e=11%2F20%2F2018&rank=2, 12 pages.

ClinicalTrials.gov Identifier: NCT03629262, Dexmedetomidine Supplemented Intravenous Analgesia in Elderly After Orthopedic Surgery, First Posted—Aug. 14, 2018, Last Update Posted—Dec. 11, 2018, retrieved from https://clinicaltrials.gov/ct2/show/NCT03629262?cond=Dexmedetomidine&sfpd_s=07%2F14%2F2018&sfpd_e=11%2F20%2F2018&rank=3, 11 pages.

ClinicalTrials.gov Identifier: NCT03629483, Dexmedetomidine Combined With Ropivacaine for Postoperative Continuous Femoral Nerve Block, First Posted—Aug. 14, 2018, Last Update Posted—Dec. 11, 2018, retrieved from https://clinicaltrials.gov/ct2/show/NCT03629483?cond=Dexmedetomidine&sfpd_s=07%2F14%2F2018&sfpd_e=11%2F20%2F2018&rank=4, 10 pages.

ClinicalTrials.gov Identifier: NCT03655847, Acceptable Hemodynamic Changes in Dexmedetomidine for Single Intravenous Bolus Injection, First Posted—Aug. 31, 2018, Last Update Posted—Feb. 15, 2019, retrieved from https://clinicaltrials.gov/ct2/show/NCT03655847?cond=Dexmedetomidine&sfpd_s=07%2F14%2F2018&sfpd_e=11%2F20%2F2018&rank=9, 7 pages.

ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—Sep. 13, 2018, retrieved from https://clinicaltrials.gov/ct2/show/NCT03668951?term=buccal&cond=dexmedetomidine &sfpd_s=07%2F01%2F2018&rank=1, 7 pages.

ClinicalTrials.gov Identifier: NCT03708315, Precedex for Schizophrenia (DEX), First Posted—Oct. 17, 2018, Last Update Posted—Oct. 17, 2018, retrieved from https://clinicaltrials.gov/ct2/show/NCT03708315?cond=Dexmedetomidine&sfpd_s=07%2F14%2F2018&sfpd_e=11%2F20%2F2018&rank=33, 6 pages.

ClinicalTrials.gov Identifier: NCT03742180, Sublingual Ketorolac Compared to Intranasal Dexmedetomidine for Postoperative Analgesia in Pediatric Patients Undergoing Bilateral Myringotomy, First Posted—Nov. 15, 2018, Last Update Posted—Nov. 15, 2018, retrieved from https://clinicaltrials.gov/ct2/show/NCT03742180?term=sublingual&cond=dexmedetomidine&sfpd_s=07%2F01%2F2018&rank=1, 6 pages.

ClinicalTrials.gov Identifier: NCT03779282, Ketodex for Emergence Delirium in Children Undergoing Outpatient Strabismus Surgery, First Posted—Dec. 18, 2018, Last Update Posted—Dec. 18, 2018, retrieved from https://clinicaltrials.gov/ct2/show/NCT03779282?term=dexmedetomidine&cond=Agitation%2C+Emergence, 5 pages.

ClinicalTrials.gov Identifier: NCT03806777, Intra-nasal Dexmedetomidine for Children Undergoing MRI Imaging (DexmedMRI), First Posted—Jan. 16, 2019, Last Update Posted—Jan. 25, 2019, retrieved from https://clinicaltrials.gov/ct2/show/NCT03806777, 7 pages.

ClinicalTrials.gov Identifier: NCT03877120, Treatment of Alcohol Withdrawal Syndrome: Dexmedetomidine Vs Diazepam in a Hospital O'horn, First Posted—Mar. 15, 2019, Last Update Posted—Mar. 15, 2019, retrieved from https://clinicaltrials.gov/ct2/show/NCT03877120, 6 pages.

ClinicalTrials.gov Identifier: NCT03926663, Intranasal Injection of Dexmedetomidine and Bupivacaine in Septoplasty Surgeries, First Posted—Apr. 24, 2019, Last Update Posted—Aug. 1, 2019, retrieved from https://clinicaltrials.gov/ct2/show/NCT03926663, 7 pages.

ClinicalTrials.gov Identifier: NCT03938831, Dexmedetomidine and Delirium in Elderly Patients, First Posted—May 6, 2019, Last Update Posted—May 6, 2019, retrieved from https://clinicaltrials.gov/ct2/show/NCT03938831, 5 pages.

ClinicalTrials.gov Identifier: NCT03957304, Intranasal Dexmedetomidine Dose-finding Study, First Posted—May 21, 2019, Last Update Posted—May 7, 2021, retrieved from https://clinicaltrials.gov/ct2/show/NCT03957304, 9 pages.

(56) References Cited

OTHER PUBLICATIONS

ClinicalTrials.gov Identifier: NCT04200235, A Trial of Dexmedetomidine Hydrochloride Nasal Spray in Preoperative Sedation of Children, First Posted—Dec. 16, 2019, Last Update Posted—Sep. 9, 2020, retrieved from https://clinicaltrials.gov/ct2/show/NCT04200235, 8 pages.
ClinicalTrials.gov Identifier: NCT04270708, Intranasal Dexmedetomidine vs Oral Triclofos Sodium for EEG in Children With Autism, First Posted—Feb. 17, 2020, Last Update Posted—Feb. 17, 2020, retrieved from https://clinicaltrials.gov/ct2/show/NCT04270708, 8 pages.
ClinicalTrials.gov Identifier: NCT04383418, A Trial of Dexmedetomidine Hydrochloride Nasal Spray in Preoperative Sedation of Adults, First Posted—May 12, 2020, Last Update Posted—Jul. 15, 2021, retrieved from https://clinicaltrials.gov/ct2/show/NCT04383418, 7 pages.
ClinicalTrials.gov Identifier: NCT04509414, Intranasal Dexmedetomidine for Deep-sedated Pediatric Dental Patients, First Posted—Aug. 12, 2020, Last Update Posted—Aug. 12, 2020, retrieved from https://clinicaltrials.gov/ct2/show/NCT04509414, 8 pages.
ClinicalTrials.gov Identifier: NCT04665453, Dexmedetomidine and Melatonin for Sleep Induction for EEG in Children (MeloDex), First Posted—Dec. 11, 2020, Last Update Posted—Dec. 16, 2020, retrieved from https://clinicaltrials.gov/ct2/show/NCT04665453, 9 pages.
ClinicalTrials.gov Identifier: NCT04669457, Pediatric Delirium, First Posted—Dec. 16, 2020, Last Update Posted—May 11, 2021, retrieved from https://clinicaltrials.gov/ct2/show/NCT04669457, 8 pages.
ClinicalTrials.gov Identifier: NCT04859283, Premedication With Intranasal Dexmedetomidine in Sedation of Patients Undergoing Total Knee Arthroplasty (TKADEX), First Posted—Apr. 26, 2021, Last Update Posted—Sep. 10, 2021, retrieved from https://clinicaltrials.gov/ct2/show/NCT04859283, 7 pages.
ClinicalTrials.gov Identifier: NCT05065775, Bioavailability of Intranasal Dexmedetomidine (INDEX), First Posted—Oct. 4, 2021, Last Update Posted—Oct. 12, 2021, retrieved from https://clinicaltrials.gov/ct2/show/NCT05065775, 7 pages.
ClinicalTrials.gov Identifier: NCT05111431, A Trial of Dexmedetomidine Hydrochloride Nasal Spray in Preoperative Sedation of Children, First Posted—Nov. 8, 2021, Last Update Posted—Dec. 16, 2021, retrieved from https://clinicaltrials.gov/ct2/show/NCT05111431, 7 pages.
Cohen, et al., "Intranasal Dexmedetomidine for Sedation for non-contrast CT Scans in Children." Anesthesiology 2008; 109, A998, 1 page.
Cohen et al., "Oral transmucosal administration of dexmedetomidine for sedation in 4 dogs," Can Vet J. Nov. 2015; 56(11): 1144-1148.
Cohen, et al., "Treatment of post-electroconvulsive therapy agitation with dexmedetomidine." The Journal of ECT (2013); 29(2): e23-e24.
Congdon, et al., "Evaluation of the sedative and cardiovascular effects of intramuscular administration of dexmedetomidine with and without concurrent atropine administration in dogs." Journal of the American Veterinary Medical Association (2011); 239(1): 81-89.
Co-pending U.S. Appl. No. 17/698,407, inventor Yocca; Frank D., filed Mar. 18, 2022.
Co-pending U.S. Appl. No. 17/993,422, inventors Kakumanu; Vasukumar et al., filed Nov. 23, 2022.
Cozzi, et al., "Intranasal Dexmedetomidine Sedation as Adjuvant Therapy in Acute Asthma Exacerbation With Marked Anxiety and Agitation." Ann Emerg Med. (2016); 69(1): 125-127.
Czinn, et al., "Effectiveness of Intramuscular Dexmedetomidine for Sedation in Young Children Undergoing Diagnostic Testing." The Anesthiology Annual Meeting, American Society of Anestheologists (2011); Abstract A578, 2 pages.
Darrouj et al. "Dexmedetomidine infusion as adjunctive therapy to benzodiazepines for acute alcohol withdrawal," Annals of Pharmacotherapy (2008), 42(11), 1703-1705.

Dewhirst, et al., "Pain management following myringotomy and tube placement:Intranasal dexmedetomidine versus intranasal fentanyl." Int J Pediatr Otorhinolaryngol. (2014); 78 (7): 1090-1094.
Diaper et al., "Pharmacological strategies for detoxification," Br J Clin Pharmacol (2013), 77(2):302-314.
Djaiani et al., "Dexmedetomidine versus Propofol Sedation Reduces Delirium after Cardiac Surgery," Anesthesiology 2016; 124:362-368.
Dogru, et al., "The Effectiveness of Intramuscular Dexmedetomidine on Hemodynamic Responses During Tracheal Intubation and Anesthesia Induction of Hypertensive Patients: A Randomized, Double-Blind, Placebo-Controlled Study." Current Therapeutic Research (2007); 68(5): 292-302.
D'Orazi, Citalopram/opiate alkaloids Serotonin syndrome, treated with dexmedetomidine: case report, Reactions Weekly, Nov. 2015, p. 117, vol. 1579, Issue 1.
Dua, et al., "Comparative evaluation of dexmedetomidine as a premedication given intranasally vs orally in children between 1 to 8 years of age undergoing minor surgical procedures." Pediatric Anesthesia and Critical Care Journal (2016); 4(1): 13-17.
Dun Dar et al., "Pharmacological treatment of acute agitation associated with psychotic and bipolar disorder: a systematic review and meta-analysis," Hum. Psychopharmacol Clin Exp 2016, 31: 268-285.
Dyck, et al., "The pharmacokinetics and hemodynamic effects of intravenous and intramuscular dexmedetomidine hydrochloride in adult human volunteers." Anesthesiology (1993); 78(5): 813-820.
Ebert et al., "The Effects of Increasing Plasma Concentrations of Dexmedetomidine in Humans," Anesthesiology 2000; 93:382-394.
Economopoulos, O., "BioXcel Therapeutics CEO Says Wearable Devices Are Another Tool to Combat Alzheimer's Agitation," Benzinga, Apr. 15, 2020, 4 pages, retrieved from: https://www.benzinga.com/general/biotech/20/04/15808398/bioxcel-therapeutics-ceo-says-wearable-devices-are-another-tool-to-combat-alzheimers-agitation.
El-Gohary and Rizk, "Dexmedetomidine for Emergence Agitation after Sevoflurane Anesthesia in Preschool Children Undergoing Day Case Surgery: Comparative Dose-Ranging Study." The Medical Journal of Cairo University (2011); 79(2): 17-23.
El-Hamid and Yassin, "Effect of intranasal dexmedetomidine on emergence agitation after sevoflurane anesthesia in children undergoing tonsillectomy and/or adenoidectomy." Saudi Journal of Anesthesia (2017); 11 (2): 137-143.
Emerick, D., "Automatic pain pathways," Dr. Darren R. Emerick, Apr. 2019, 1 page.
Emerick, D., "Sumo Pharma Version 1.4," Dr. Darren R. Emerick, Apr. 2019, 3 pages.
Emerick, D., "Sumo Pharma Version 1.4a," Dr. Darren R. Emerick, Apr. 2019, 1 page.
Emerick, D., "Sumo Pharma Version 1.5," Dr. Darren R. Emerick, Apr. 2019, 2 pages.
Emerick, D., "Sumo Pharma Version 1.6," Dr. Darren R. Emerick, Apr. 2019, 1 page.
Emery, et al., "Sedative Effects of Intranasal Midazolam and Dexmedetomidine in 2 Species of Tortoises (*Chelonoidis carbonaria* and *Geochelone platynota*)." Journal of Exotic Pet Medicine (2014); 23 (4): 380-383.
Erkola, et al., "Comparison of intramuscular dexmedetomidine and midazolam premedication for elective abdominal hysterectomy." Anesth Analg. (1994); 79(4): 646-653.
EudraCT Clinical Trial No. 2016-001567-37, Efficacy of single dose intranasal dexmedetomidine for conscious sedation in dental practice in dentophobic uncooperative patients with intellectual disability. University Medical Center Groningen, Date of record first entered Jul. 20, 2016, https://www.clinicaltrialsregister.eu/ctr-search/trial/2016-001567-37/NL, downloaded May 6, 2018, 5 pages.
Extended European Search Report for European Patent Application No. 15850725.1, dated May 24, 2018, 11 pages.
Extended European Search Report for European Patent Application No. 17885750.4, dated Jul. 16, 2020, 7 pages.
Extended European Search Report for European Patent Application No. 19824839.5, dated Feb. 28, 2022, 14 pages.

(56) References Cited

OTHER PUBLICATIONS

Extended European Search Report for European Patent Application No. 19826778.3, dated May 10, 2022, 6 pages.
Ezz, "Preoperative intranasal dexmedetomidine versus intranasal ketamine for prevention of emergence agitation after sevoflurane in myringotomy patients: A randomized clinical trial." Egyptian Journal of Anaesthesia (2017); 33 (2): 141-146.
Farag et al., "Using Dexmedetomidine to Manage Patients with Cocaine and Opioid Withdrawal, Who Are Undergoing Cerebral Angioplasty for Cerebral Vasospasm," Anesthesia & Analgesia, Dec. 2006, vol. 103, No. 6, pp. 1618-1620.
Ferguson et al., "Intranasal dexmedetomidine: Procedural sedation in palliative care: A case report," Palliat Med. 2021, 35(8):1625-1628.
Finkel et al., "The use of dexmedetomidine to facilitate acute discontinuation of opioids after cardiac transplantation in children," Critical Care Medicine, Sep. 2005, 33(9):2110-2112.
Finkel et al., "The Use of Dexmedetomidine to Facilitate Opioid and Benzodiazepine Detoxification in an Infant," Anesthesia & Analgesia, 2004, 98:1658-9.
Gagnon D.J., et al., "Transition from Dexmedetomidine to Enteral Clonidine for ICU Sedation: An Observational Pilot Study," Pharmacotherapy, Mar. 2015, vol. 35(3), pp. 251-259.
Garg et al., "Efficacy of dexmedetomidine for prevention of emergence agitation in patients posted for nasal surgery under desflurane anaesthesia: A prospective double-blinded randomised controlled trial," Indian J Anaesth 2018;62:524-30.
Garg et al., "Use of dexmedetomidine with Propofol in modified electroconvulsive therapy: stable hemodynamics, optimum seizure duration and early recovery," Anaesthesia and Anaesthetics, 2018, 2(1): 1-5.
Garrity et al., "Dexmedetomidine-Induced Sedation Does Not Mimic the Neurobehavioral Phenotypes of Sleep in Sprague Dawley Rat," Sleep 2015;38(1):73-84.
Gaudio, et al., "Alfaxalone anaesthesia in Lemur catta following dexmedetomidine-butorphanol-midazolam sedation." Veterinary Anaesthesia and Analgesia (2018); 45(3): 351-356.
Ghai, et al., "Effect of Low Dose Dexmedetomidine on Emergence Delirium and Recovery Profile following Sevoflurane Induction in Pediatric Cataract Surgeries." Journal of Anesthesiology (2015); vol. 2015, Article ID 617074, 7 pages.
Ghali, et al., "Preanesthetic medication in children: A comparison of intranasal dexmedetomidine versus oral midazolam." Saudi J Anaesth. (2011); 5 (4): 387-391.
Gilsbach et al., "Are the pharmacology and physiology of 2adrenoceptors determined by 2heteroreceptors and autoreceptors respectively?," British Journal of Pharmacology (2012) 165 90-102.
Gioeni et al., "Evaluation of an oral transmucosal administration of dexmedetomidine-butorphanol and dexmedetomidine-methadone in dogs," International Journal of Health and Animal Science Food Safety, vol. IV, No. 1s, Proceeding of Veterinary and Animal Science Days, Jun. 6-8, 2017, Milan, Italy, 2 pages.
Giovannitti et al., "Alpha-2 Adrenergic Receptor Agonists: A Review of Current Clinical Applications," Anesth Prog, 2015, 62:31-38.
Granholm, et al., "Evaluation of the clinical efficacy and safety of intramuscular and intravenous doses of dexmedetomidine and medetomidine in dogs and their reversal with atipamezole." Veterinary Anaesthesia and Analgesia (2006); 33(4): 214-223.
Grubb, et al., "Cardiovascular and respiratory effects, and quality of anesthesia produced by alfaxalone administered intramuscularly to cats sedated with dexmedetomidine and hydromorphone." Journal of Feline Medicine and Surgery (2013); 15 (10): 858-865.
Gu et al., "ED50 of Intranasal Dexmedetomidine Sedation for Transthoracic Echocardiography in Children with or without a History of Cardiac Surgery for Cyanotic Congenital Heart Disease," Hindawi BioMed Research International, 2020, vol. 2020, Article ID 1349432, 7 pages.
Guler, et al., "Single-dose dexmedetomidine reduces agitation and provides smooth extubation after pediatric adenotonsillectomy." Pediatric Anesthesia (2005); 15(9): 762-766.

Gumus et al., "Comparison of Effects of Different Dexmedetomidine and Chloral Hydrate Doses Used in Sedation on Electroencephalography in Pediatric Patients," Journal of Child Neurology 2015, vol. 30(8) 983-988.
Gupta, et al., "Comparison between intranasal dexmedetomidine and intranasal midazolam as premedication for brain magnetic resonance imaging in pediatric patients: A prospective randomized double blind trial." J Anaesthesiol Clin Pharmacol. (2017); 33 (2): 236-240.
Guthrie et. al., "Pharmacologic interventions for the treatment of opioid dependence and withdrawal," DICP (1990) Jul.-Aug.; 24(7-8): 721-734.
Gutirrez, R.E.P., "Clinical case of rapid opiate detoxification under anesthesia," Anestesia Pediatrica e Neonatale, vol. 9, No. 1, Settembre-Ottobre 2011, 10 pages.
Gyanesh, et al., "Comparison between intranasal dexmedetomidine and intranasal ketamine as premedication for procedural sedation in children undergoing MRI: a double-blind, randomized, placebo-controlled trial." J Anesth. (2014); 28 (1): 12-18.
Haenecour et al., "Prolonged Dexmedetomidine Infusion and Drug Withdrawal In Critically Ill Children," J Pediatr Pharmacol Ther 2017;22(6):453-460.
Han, et al., "A randomized study of intranasal vs. intravenous infusion of dexmedetomidine in gastroscopy." Int J Clin Pharmacol Ther. (2014); 52 (9): 756-761.
Hauber, et al., "Dexmedetomidine as a Rapid Bolus for Treatment and Prophylactic Prevention of Emergence Agitation in Anesthetized Children." Anesthesia & Analgesia (2015); 121(5): 1308-1315.
Hitt, et al., "An Evaluation of Intranasal Sufentanil and Dexmedetomidine for Pediatric Dental Sedation." Pharmaceutics (2014); 6 (1): 175-184.
Honey et al., "2-Receptor Agonists for Treatment and Prevention of Iatrogenic Opioid Abstinence Syndrome in Critically Ill Patients," Ann Pharmacother., 2009;43:1506-1511.
Hong et al., "Dexmedetomidine alleviates smoke-induced bronchial and alveolar epithelial cell injury," Gen Physiol Biophys., May 2020;39(3):293-300.
Hong et al., "Dexmedetomidine preconditioning ameliorates lung injury induced by pulmonary ischemia/reperfusion by upregulating promoter histone H3K4me3 modification of KGF-2," Experimental Cell Research, Sep. 2021, 406, 112762, 11 pages.
Hospira Safety Data Sheet, Precedex (dexmedetomidine hydrochloride) Injection, Solution, Jun. 2, 2014, pp. 1-7.
Hossein, et al., "Comparing the effect of premedication with intranasal dexmedetomidine and intra-nasal midazolam on sedation and anxiety level in children undergoing elective surgery." Journal of Anaesthesiology and Pain (2016); 6 (3): 1-10. Abstract.
Hrishi, et al., "A Novel Use of a Novel Drug: Preoperative Nasal Preparation with Dexmedetomidine for Transnasal Transsphenoidal Neurosurgery Approach in Skull Base Neurosurgery." Indian Journal of Neurosurgery (2017); 06 (03): 170-175.
Hsu et al., "Dexmedetomidine Directly Increases Tau Phosphorylation," Journal of Alzheimer's Disease (2015) 44:839-850.
Hsu et al., "Selection of medications for pediatric procedural sedation outside of the operating room," Up to Date, Oct. 10, 2017, 15 pages, retrieved from https://www.uptodate.com/contents/selectionof-medications-for-pediatric-procedural-sedation-outside-of-the-operating-room.
Ibacache, et al., "Single-Dose Dexmedetomidine Reduces Agitation After Sevoflurane Anesthesia in Children." Anesthesia & Analgesia (2004); 98(1): 60-63.
Ibrahim, "A prospective, randomized, double blinded comparison of intranasal dexmedetomidine vs intranasal ketamine in combination with intravenous midazolam for procedural sedation in school aged children undergoing MRI." Anesthesia Essays and Researches (2014); 8 (2): 179-186.
Iirola, et al., "Bioavailability of dexmedetomidine after intranasal administration." European Journal of Clinical Pharmacology (2011); 67 (8): 825-831.
Iirola, et al., "Population pharmacokinetics of dexmedetomidine during long-term sedation in intensive care patients," British Journal of Anaesthesia 108 (3): 460-8 (2012).

(56) References Cited

OTHER PUBLICATIONS

International Search Report and Written Opinion of the International Searching Authority for International Application No. PCT/US2020/051256, dated Dec. 10, 2020, 18 paqes.
IRCT Registration No. IRCT2015103011398N9, Effect of intranasal administration of dexmedetomidine in providing moderate sedation for patients undergoing ERCP ; a randomized control trial. Iran University of Medical Sciences, Registration date Nov. 4, 2015, http://en.irct.ir/trial/11663, downloaded May 5, 2018, 12 pages.
Isik, et al., "Dexmedetomidine decreases emergence agitation in pediatric patients after sevoflurane anesthesia without surgery." Pediatric Anesthesia (2006); 16(7): 748-753.
Jaakola, et al., "Intramuscular dexmedetomidine premedication—an alternative to midazolam-fentanyl-combination in elective hysterectomy?" Acta Anaesthesiol Scand. (1994); 38(3): 238-243.
Jayaram, et al., "A comparative study to evaluate the effect of intranasal dexmedetomidine versus oral alprazolam as a premedication agent in morbidly obese patients undergoing bariatric surgery." J Anaesthesiol Clin Pharmacol. (2013); 29(2): 179-182.
Ji, "Intramuscular Dexmedetomidine in Burns Victims—Preliminary Results." Anaesthesiology and Intensive Care Medicine (2008); 2: 82-86 (with English Abstract).
Jia, et al., "A randomised study of intranasal dexmedetomidine and oral ketamine for premedication in children." Anaesthesia (2013); 68 (9): 944-949.
Jia et al., "Application of intranasal dexmedetomidine hydrochloride combined sevoflurane inhalation anesthesia in pediatric lingual frenoplasty," Journal of Xinxiang Medical University (2015), 32(8), 732-734, English Abstract only.
Jun et al., "The effects of intranasal dexmedetomidine premedication in children: a systematic review and meta-analysis," Can J Anesth/J Can Anesth (2017) 64:947-961.
Jung et al., "1877: Dexmedetomidine for Treatment of Refractory Opioid Withdrawal," Critical Care Medicine: Dec. 2016, vol. 44, No. 12 (Suppl.), p. 544.
Jung et al., "Dexmedetomidine for Treatment of Refractory Heroin Withdrawal," Journal of Emergency Nursing, 2017, 43(2):182-184.
Jung, et al., "Effect of dexmedetomidine on emergence agitation in male patients undergoing closed reduction of a nasal bone fracture." RMJ (2015); 40(2): 191-196.
Kambow, et al., "Randomized Double Blind Clinical Trial of Intramuscular Dexmedetomidine V/S Midazolam as Premedication in Paediatric Surgical Patients." J. Evolution Med. Dent. Sci. (2016); 5(42): 2566-2570.
Kang et al., "The correlation of heart rate between natural sleep and dexmedetomidine sedation," Korean J Anesthesiol. Apr. 2019; 72(2): 164-168.
Karaaslan, et al., "Comparison of buccal and intramuscular dexmedetomidine premedication for arthroscopic knee surgery." Journal of Clinical Anesthesia (2006); 18(8): 589-593.
Kawaai et al., "Dexmedetomidine decreases the oral mucosal blood flow," British Journal of Oral and Maxillofacial Surgery (2013) 51: 928-931.
Kaya, et al., "The Effects of Intramuscular Dexmedetomidine Premedication on Hemodynamics, Plasma Norepinephrine, Cortisol and Glucose Concentrations." O.M.. Tp Dergisi (2006); 23(1): 9-16.
Keating, G., "Dexmedetomidine: A Review of Its Use for Sedation in the Intensive Care Setting," Drugs (2015) 75:1119-1130.
Keles et al., "The Effect of Oral Dexmedetomidine Premedication on Preoperative Cooperation and Emergence Delirium in Children Undergoing Dental Procedures," Hindawi BioMed Research International, 2017, vol. 2017, Article ID 6742183, 7 pages.
Kelley, et al., "Intramuscular Dexmedetomidine & Midazolam for Preoperative Sedation: A Case Series." Pediatric Anesthesia (Winter 2013), University of Pittsburgh, Poster Board, 1 pagehttp://www2.pedsanesthesia.org/meetings/2013winter/posters/uploads/373--NM-293.pdf.

Khenissi, et al., "Comparison of intramuscular alfaxalone and ketamine combined with dexmedetomidine and butorphanol for castration in cats." Journal of Feline Medicine and Surgery (2016); 19(8): 791-797.
Kim, et al., "Appropriate dose of dexmedetomidine for the prevention of emergence agitation after desflurane anesthesia for tonsillectomy or adenoidectomy in children: up and down sequential allocation." BMC Anesthesiology (2015); 15: 79, 6 pages.
Kim, et al., "Dexmedetomidine for sedation in pediatric patients who received more than 20 sessions of radiation therapy-two cases report." Korean Journal of Anesthesiology (2016); 69 (6): 627-631.
Kim et al., "Risk Factors of Emergence Agitation in Adults Undergoing General Anesthesia for Nasal Surgery," Clinical and Experimental Otorhinolaryngology vol. 8, No. 1, 46-51, Mar. 2015.
Kobayashi, et al., "Efficacy of Dexmedetomidine for Controlling Delirium in Intensive Care Unit Patients." Japanese Journal of Anesthesiology [Masui] (2007); 56(10): 1155-1160.
Kobayashi, et al., "Mechanism of the Inhibitory Effect of Surfactants on Intramuscular Absorption of Drugs." Chemical and Pharmaceutical Bulletin (1977); 25(7): 1547-1554.
Konia, M., "Oral dexmedetomidine for preoperative sedation in an adult uncooperative autistic patient," Journal of Clinical Anesthesia (2016) 34, 29-31.
Korpivaara et al., "Dexmedetomidine oromucosal gel for noise-associated acute anxiety and fear in dogsa randomised, double-blind, placebo-controlled clinical study," Veterinary Record (2017) 180, 356, 7 pages.
Korpivaara et al., "Effect of dexmedetomidine oromucosal gel for alleviation of canine acute fear and anxiety associated with noise at sub-sedative doses—A pilot study," BSAVA Congress 2014, Poster, 1 page.
Kostoglou, et al., "Effect of ß-carotene on health status and performance of sows and their litters." Journal of Animal Physiology and Animal Nutrition (2000); 83 (3): 150-157.
Krimins, et al., "Hemodynamic effects in dogs after intramuscular administration of a combination of dexmedetomidine-butorphanol-tiletamine-zolazepam or dexmedetomidine-butorphanol-ketamine." American Journal of Veterinary Research (2012); 73(9): 1363-1370. Abstract.
Kstner, et al., "Clinical comparison of preanaesthetic intramuscular medetomidine and dexmedetomidine in domestic sheep." DTW. Deutsche Tierarztliche Wochenschrift (2001); 108 (10): 409-413.
Kumar, et al., "Efficacy of intranasal dexmedetomidine versus oral midazolam for paediatric premedication." Indian J Anaesth (2017); 61: 125-130.
Kumar et al., "Role of dexmedetomidine for sedation in a patient with schizophrenia for strabismus surgery," Indian J Anaesth. Nov. 2016; 60(11): 856-857.
Kumari, et al., "Clinico-anesthetic and Hemodynamic Effects of Midazolam and Dexmedetomidine-Midazolam with Propofol in Dogs During Ovariohysterectomy." The Philippine Journal of Veterinary Medicine (2017); 54(1): 46-53.
Kundra et al., "Oral ketamine and dexmedetomidine in adults' burns wound dressing—A randomized double blind cross over study," Burns 39 (2013) 1150-1156.
Kurlansky, et al., "Role of the carrier solution in cyclosporine pharmacokinetics in the baboon." The Journal of Heart Transplantation (1986); 5(4): 312-316.
Lami et al., "Transmucosal dexmedetomidine for computed tomography sedation," Paediatr Anaesth., 2008, 18:349-350.
Lehman et al., "Practice Guideline for the Treatment of Patients With Schizophrenia," American Psychiatric Association Practice Guidelines, Second Edition, 2010, 184 pages.
Lei et al., "Incidence and risk factors of bradycardia in pediatric patients undergoing intranasal dexmedetomidine sedation," Acta Anaesthesiologica Scandinavica (2020), 64: 464-471.
Levnen, et al., "Dexmedetomidine Premedication Attenuates Ketamine-induced Cardiostimulatory Effects and Postanesthetic Delirium." Anesthesiology (1995); 82: 1117-1125.
Li, et al., "A comparison of intranasal dexmedetomidine for sedation in children administered either by atomiser or by drops." Anaesthesia (2016); 71: 522-528.

(56) References Cited

OTHER PUBLICATIONS

Li et al., "Dexmedetomidine inhibits inflammation in microglia cells under stimulation of LPS and ATP by c-Fos/NLRP3/caspase-1 cascades," EXCLI Journal 2018;17:302-311.

Li et al., "Impact of dexmedetomidine on the incidence of delirium in elderly patients after cardiac surgery: A randomized controlled trial," PLoS One, Feb. 9, 2017, 15 pages.

Li, et al., "Intranasal dexmedetomidine for sedation in children undergoing transthoracic echocardiography study a prospective observational study." Pediatric Anesthesia (2015); 25 (9): 891-896.

Li, et al., "Intranasal dexmedetomidine with and without buccal midazolam for procedural sedation in autistic children: a double-blind randomised controlled trial." The Lancet (2017); 390 (4): S26.

Lili, et al., "The application of dexmedetomidine in children undergoing vitreoretinal surgery." Journal of Anesthesia (2012); 26(4): 556-561.

Lin, et al., "Efficacy of premedication with intranasal dexmedetomidine on inhalational induction and postoperative emergence agitation in pediatric undergoing cataract surgery with sevoflurane." Journal of Clinical Anesthesia (2016); 33: 289-295.

Liu et al., "Safety and sedative effect of intranasal dexmedetomidine in mandibular third molar surgery: a systematic review and meta-analysis," Drug Design, Development and Therapy (2019), 13:1301-1310.

Liu et al., "Comparison of sedative effects of two methods of intranasal dexmedetomidine in cardiac ultrasonography in infants with congenital heart disease," Practical Medicine and Clinic . 2015, 18( 12), 1452-1454, English Abstract only.

Liu et al., "Determination of the 90% effective dose of intranasal dexmedetomidine for sedation during electroencephalography in children," Acta Anaesthesiologica Scandinavica (2019), 63, 847-852.

Liu X., et al., "Dexmedetomidine Versus Propofol Sedation Improves Sublingual Microcirculation After Cardiac Surgery: A Randomized Controlled Trial," Journal of Cardiothoracic and Vascular Anesthesia, 2016, vol. 30(6), pp. 1509-1515.

Liyan, Chu et al., "Effect of dexmedetomidine on minimum alveolar concentration of sevoflurane in children undergoing inhalation anesthesia," Beijing Yixue I Beijing Medical Journal, 2017, vol. 39, Issue 6, pp. 581-584 (English abstract only).

Li et al., "Comparison of preoperative application of different doses of dexmedetomidine intranasal in children undergoing outpatient surgery," Sichuan Yixue (2015), 36(09), 1209-1211. DOI: 1 0.16252/j.cnki.issn1 004-0501-2015.09.002.

Li et al., "Pharmacokinetic and pharmacodynamic study of intranasal and intravenous dexmedetomidine," British Journal of Anaesthesia (2018), 120(5), 960-968.

Li et al., "The 95% effective dose of intranasal dexmedetomidine sedation for pulmonary function testing in children aged 1-3 years: A biased coin design up-and-down sequential method," Journal of Clinical Anesthesia (2020), 63, 109746, 5 pages.

Louis et al., "Effects of dexmedetomidine on delirium duration of non-intubated ICU patients (4D trial): study protocol for a randomized trial," Trials (2018) 19:307, 11 pages.

Lu, et al., "Intranasal Dexmedetomidine as a Sedative Premedication for Patients Undergoing Suspension Laryngoscopy: A Randomized Double-Blind Study." PLoS One (2016); 11(5): e0154192.

Maccioli et al., "Dexmedetomidine to Facilitate Drug Withdrawal," Anesthesiology, Feb. 2003, V 98, No. 2, pp. 575-575.

Madhav et al., "Orotransmucosal drug delivery systems: A review," Journal of Controlled Release (2009) 140: 2-11.

Mahmoud et al., "Dexmedetomidine: review, update, and future considerations of paediatric perioperative and periprocedural applications and limitations," British Journal of Anaesthesia 2015, 171-82, doi: 10.1093/bja/aev226.

Malhotra, et al., "Comparative evaluation of dexmedetomidine and midazolam-ketamine combination as sedative agents in pediatric dentistry: A double-blinded randomized controlled trial." Contemp Clin Dent (2016); 7: 186-192.

Manaa, et al., "Fentanyl versus dexmedetomidine effect on agitation after sevoflurane anaesthesia." Saudi J Anaesth. (2007); 1(2): 57-61, 10 pages.

Martin et al., "The Role of the 2-Adrenoceptor Agonist Dexmedetomidine in Postsurgical Sedation in the Intensive Care Unit," J Intensive Care Med 2003;18:29-41.

Mason, et al., "Intramuscular dexmedetomidine: an effective route of sedation preserves background activity for pediatric electroencephalograms." J Pediatr. (2012); 161(5): 927-932.

Mason, et al., "Intramuscular dexmedetomidine for pediatric electroencephalogram (EEG) sedation: 10AP3-7." European Journal of Anaesthesiology (EJA) (2012); 29: p. 161.

Mason, et al., "Intramuscular Dexmedetomidine Sedation for Pediatric MRI and CT." American Journal of Roentgenology (2011); 197: 720-725.

Mazy et al., "Spinal anesthesia for lengthy lower limb orthopedic surgeries: dexmedetomidine plus fentanyl versus dexmedetomidine," Ain-Shams Journal of Anesthesiology (2019) 11:10, 8 pages.

Micieli, et al., "Sedative and cardiovascular effects of intranasal or intramuscular dexmedetomidine in healthy dogs." Vet Anaesth Analg. (2017); 44(4): 703-709.

Miller et al., "Comparison of Intranasal Dexmedetomidine and Oral Pentobarbital Sedation for Transthoracic Echocardiography in Infants and Toddlers: A Prospective, Randomized, Double-Blind Trial," Anesthesia & Analgesia, Jun. 2018, vol. 126, No. 6, pp. 2009-2016.

Miller et al., "Does intranasal dexmedetomidine provide adequate plasma concentrations for sedation in children: a pharmacokinetic study," British Journal of Anaesthesia (2018), 120(5), 1056-1065.

Miller, et al., "Dosing and efficacy of intranasal dexmedetomidine sedation for pediatric transthoracic echocardiography: a retrospective study." Canadian Journal of Anesthesia (2016); 63 (7): 834-841.

Misra et al., "Effect of preoperative dexmedetomidine nebulization on the hemodynamic response to laryngoscopy and intubation: a randomized control trial," Korean Journal of Anesthesiology 2021; 7 4(2): 150-157.

Mizrak, et al., "Dexmedetomidine Use during Strabismus Surgery in Agitated Children." Med Princ Pract (2011); 20(5): 427-432.

Mizrak, et al., "Premedication with dexmedetomidine and midazolam attenuates agitation after electroconvulsive therapy." J Anesth. (2009); 23(1): 6-10.

Mohite et al., "Role of dexmedetomidine in pediatric dental sedation," J Dent Anesth Pain Med., Apr. 2019;19(2):83-90.

Montoya et al., "Validation of the Excited Component of the Positive and Negative Syndrome Scale (PANSS-EC) in a naturalistic sample of 278 patients with acute psychosis and agitation in a psychiatric emergency room," Health and Quality of Life Outcomes, 2011, 9:18, 11 pages.

Moshiri et al., "Premedication effect of dexmedetomidine and alfentanil on seizure time, recovery duration, and hemodynamic responses in electroconvulsive therapy," Annals of Cardiac Anaesthesia, Apr.-Jun. 2016, vol. 19, Issue 2, pp. 263-268.

Mostafa, et al., "Effect of Different Doses of Dexmedetomidine on Stress Response and Emergence Agitation after Laparoscopic Cholecystectomy: Randomized Controlled Double-Blind Study." J Anesth Clin Res (2017); 8: 707, 6 pages.

Mountain et al., "Dexmedetomidine as a Pediatric Anesthetic Premedication to Reduce Anxiety and to Deter Emergence Delirium," AANA Journal, Jun. 2011, vol. 79, No. 3, pp. 219-224.

Mukherjee, et al., "Emergence agitation prevention in paediatric ambulatory surgery: A comparison between intranasal Dexmedetomidine and Clonidine." J Res Pharm Pract. (2015); 4(1): 24-30.

Mult, A., "Prolonged Dexmedetomidine Infusion as an Adjunct in Treating Sedation-Induced Withdrawal," Anesth Analg 2003;96:1054-1055.

Muszkat et al., "Alpha2-Adrenergic Receptor-Induced Vascular Constriction in Blacks and Whites," Hypertension, 2004, vol. 43, pp. 31-35.

Na, et al., "Randomized controlled trial on influence of nasal administration of dexmedetomidine after induction of anesthesia on agitation of children in ophthalmologic surgery." Adverse Drug Reactions Journal (2016); 18 (2): 95-98. Abstract.

Naples, et al., "Comparison of the Anesthetic Effects of Oral Transmucosal Versus Injectable Medetomidine in Combination with

(56) References Cited

OTHER PUBLICATIONS

Tiletamine-Zolazepam for Immobilization of Chimpanzees (*Pan troglodytes*)." Journal of Zoo and Wildlife Medicine (2010); 41 (1): 50-62.
Nasr et al., "Ultra-rapid opiate detoxification using dexmedetomidine under general anesthesia," J Opioid Manag., 2011;7(5):337-344.
Nawrat, A., "Triple combo: calming Alzheimer's agitation with AI, wearables and a novel drug," Medical Device Network, Jan. 28, 2020, 4 pages, retrieved from https://www.medicaldevice-network.com/analysis/wearable-ai-device-for-agitation/#:~:text =.
Neville, et al., "Double-blind Randomized Controlled Trial of Intranasal Dexmedetomidine Versus Intranasal Midazolam as Anxiolysis Prior to Pediatric Laceration Repair in the Emergency Department." Acad Emerg Med. (2016); 23 (8): 910-917.
Ni, et al., "Effect of Dexmedetomidine on Preventing Postoperative Agitation in Children: A Meta-Analysis." PLoS One (2015); 10 (5): e0128450.
Nitturi et al., "A Comparative Evaluation of Intranasal Dexmedetomidine and Intranasal Midazolam for Premedication in Pediatric Surgery," IAIM, 2018; 5(1): 82-94.
Niyogi et al., "Attenuation of haemodynamic responses to laryngoscopy and endotracheal intubation with dexmedetomidine: A comparison between intravenous and intranasal route," Indian J Anaesth 2019;63:915-923.
Nizari et al., "Non-amyloidogenic effects of 2 adrenergic agonists: implications for brimonidine-mediated neuroprotection," Cell Death Dis., 2016; 7(12): e2514, 13 pages.
Non Final Office Action for U.S. Appl. No. 17/496,470 dated Dec. 14, 2022, 10 pages.
Nooh, et al., "Intranasal atomized dexmedetomidine for sedation during third molar extraction." Int J Oral Maxillofac Surg. (2013); 42 (7): 857-862.
Nuamah et al., "The past, present and future of opioid withdrawal assessment: a scoping review of scales and technologies," BMC Medical Informatics and Decision Making (2019) 19:113, 11 pages.
O'Brien, et al., "Dexmedetomidine and the successful management of electroconvulsive therapy postictal agitation: a case report." The Journal of ECT (2010); 26(2): 131-133.
Ocengiz et al., "Oral melatonin, dexmedetomidine, and midazolam for prevention of postoperative agitation in children," Journal of Anesthesia., 2011, pp. 184-188.
Oschman et al., "Dexmedetomidine for opioid and benzodiazepine withdrawal in pediatric patients," Am J Health-Syst Pharm. 2011; 68:1233-8.
Ouchi et al., "Dexmedetomidine Dose Dependently Enhances the Local Anesthetic Action of Lidocaine in Inferior Alveolar Nerve Block a Randomized Double-Blind Study," Reg Anesth Pain Med 2016;41: 348-355.
Pant D., et al., "Comparison of Sublingual Midazolam and Dexmedetomidine for Premedication in Children," Minerva Anestesiologica, 2014, vol. 80(2), pp. 167-175.
Parikh et al., "Single Dose Pharmacokinetics of Fentanyl Sublingual Spray and Oral Transmucosal Fentanyl Citrate in Healthy Volunteers: A Randomized Crossover Study," Clinical Therapeutics, 2013, vol. 35, No. 3, pp. 236-243.
Park et al., "Dexmedetomidine Oral Mucosa Patch for Sedation Suppresses Apoptosis in Hippocampus of Normal Rats," Int Neurourol J 2017;21 Suppl 1:S39-47.
Pasin L., et al., "Dexmedetomidine vs Midazolam as Preanesthetic Medication in Children: a Meta-Analysis of Randomized Controlled Trials," Pediatric Anesthesia, 2015, vol. 25, pp. 468-476.
Patel, et al., "Vasovagal syncope and severe bradycardia following intranasal dexmedetomidine for pediatric procedural sedation." Paediatr Anaesth. (2014); 24 (4): 446-448.
Pavithra, et al., "Comparison of two doses of intranasal dexmedetomidine as premedication in children." Pediatric Anesthesia and Critical Care Journal (2017); 5(2): 86-94.
Peker, et al., "Buccal versus intramuscular dexmedetomidine premedication for arthroscopic knee surgery under spinal anesthesia: A-600." European Journal of Anaesthesiology (EJA) (2006); 23: p. 156.
Peng, et al., "Premedication with dexmedetomidine in pediatric patients: a systematic review and meta-analysis." Clinics (2014); 69(11): 777-786.
Penttil et al., "Cardiovascular and parasympathetic effects of dexmedetomidine in healthy subjects," Canadian Journal of Physiology and Pharmacology, 2004, 82(5): 359-362.
Pestieau, et al., "The effect of dexmedetomidine during myringotomy and pressure equalizing tube placement in children." Pediatric Anesthesia (2011); 21 (11): 1128-1135.
Phan et al., "Clinical Uses of Dexmedetomidine in Pediatric Patients," Pediatr Drugs, 2008;10(1):49-69.
Pinelas, et al., "Effects of different doses of dexmedetomidine on anaesthetic induction with alfaxalone—a clinical trial." Veterinary Anaesthesia and Analgesia (2013); 41(4): 378-385.
Pons, et al., "Effects of dexmedetomidine administered at acupuncture point GV20 compared to intramuscular route in dogs." J Small Anim Pract. (2016); 58(1): 23-28.
Porters, et al., "Sedative and antinociceptive effects of dexmedetomidine and buprenorphine after oral transmucosal or intramuscular administration in cats." Veterinary Anaesthesia and Analgesia (2014); 41 (1): 90-96.
Porters, et al., "Pharmacokinetics of oral transmucosal and intramuscular dexmedetomidine combined with buprenorphine in cats." Journal of Veterinary Pharmacology and Therapeutics (2014); 38 (2): 203-208.
Posner, "Measuring Alertness," Ann. N.Y. Acad. Sci. (2008) 1129: 193-199.
Prabhu and Mehandale, "Comparison of oral dexmedetomidine versus oral midazolam as premedication to prevent emergence agitation after sevoflurane anaesthesia in paediatric patients." Indian J Anaesth. (2017); 61(2): 131-136.
Proctor et al., "Oral Dexmedetomidine Attenuates Hemodynamic Responses during Emergence from General Anesthesia in Chronically Instrumented Dogs," Anesthesiology, 1991, 74:108-114.
Proctor et al., "Premedication with Oral Dexmedetomidine Alters Hemodynamic Actions of Intravenous Anesthetic Agents in Chronically Instrumented Dogs," Anesthesiology, 1992, 77:554-562.
Purushotham et al., "Intranasal Dexmedetomidine Versus Oral Midazolam as Premedication in Anaesthesia in Children," RJPBCS, Jul.-Aug. 2017, 8(4), pp. 1219-1241.
Qi, et al., "The observation of the sedation effects of intranasal methods of dexmedetomidine for magnetic resonance imaging in children." BIO Web of Conferences 8, 01043 (2017), 4 pages.
Qiao, et al., "Intranasal atomised dexmedetomidine optimises surgical field visualisation with decreased blood loss during endoscopic sinus surgery: a randomized study." Rhinology (2016); 54: 38-44.
Qiao et al., "Pediatric premedication: a double-blind randomized trial of dexmedetomidine or ketamine alone versus a combination of dexmedetomidine and ketamine," BMC Anesthesiology (2017) 17:158, 7 pages.
Qiu et al., "Sedative effects of different doses of intranasal dexmedetomidine in different age groups of children," Journal of Medical Postgraduates 2014;(4):394-397, English abstract only.
Rahman et al., "The use of dexmedetomidine for refractory agitation in substance abuse patient," Crit Care & Shock (2010) 13:59-60.
Rajalakshmi, et al., "A Comparative Study Between Intranasal Dexmedetomidine and Intranasal Ketamine as a Premedication in Paediatric Surgeries." Indian Journal of Applied Research (2014); 4 (12): 379-381.
Raszplewicz, et al., "Comparison of sedation scores and propofol induction doses in dogs after intramuscular premedication with butorphanol and either dexmedetomidine or medetomidine." Veterinary Anaesthesia and Analgesia (2013); 40(6): 584-589.
Rathbone et al., "Mechanisms, barriers and pathways of oral mucosal drug permeation," Advanced Drug Delivery Reviews, (1993) 12: 41-60.
Ravipati, et al., "Dexmedetomidine decreases the requirement of ketamine and propofol during burns debridement and dressings." Clinical Investigation (2014); 58(2): 138-142.

(56) References Cited

OTHER PUBLICATIONS

Ray et al., "Dexmedetomidine for sedation during electroencephalographic analysis in children with autism, pervasive developmental disorders, and seizure disorders," Journal of Clinical Anesthesia (2008) 20, 364-368.
Reade and Finfer, "Sedation and delirium in the intensive care unit," New England Journal of Medicine, 2014; vol. 370 (5): pp. 444-454.
Riker et al., "Dexmedetomidine vs Midazolam for Sedation of Critically Ill Patients a Randomized Trial," JAMA, 2009;301(5):489-499.
Risinger, et al., M72 double-blind, placebo-controlled, single ascending dose study to determine the efficacy, safety, and pharmacokinetics of BXCL501 (Sublingual Dexmedetomidine) in agitation associated with Schizophrenia or related disorders, Clinical Poster, BioXcel Therapeutics, No date, 2 pages.
Roberts et al., "Characterizing the experience of agitation in patients with bipolar disorder and schizophrenia," BMC Psychiatry (2018) 18:104.
Rojas-Gomez and Nystrom, "Sedation and Physiological Response to Intranasal Dexmedetomidine (IN-DEX) in Patients with Severe Chronic Obstructive Pulmonary Disease (COPD)." ATS Journals 2016: Abstract A3548; American Journal of Respiratory and Critical Care Medicine (2016); 193: 1.
Roosens et al., "The use of dexmedetomidine in extreme agitation," Tijdschrift Voor Psychiatrie (2017) 59:9, 554-558, with English abstract.
Rosen et al., "The Pittsburgh Agitation Scale," American Journal of Geriatric Psychiatry, 1994, 1 page.
Ryu et al., "Sedation Protocol Using Dexmedetomidine for Third Molar Extraction," J Oral Maxillofac Surg, 2016 74:926.e1-926.e7, 7 pages.
Saad et al., "Intranasal dexmedetomidine versus intranasal midazolam as pre-anesthetic medication in pediatric age group undergoing adenotonsillectomy," Ain-Shams Journal of Anesthesiology (2020) 12:40, 10 pages.
Saito et al., "Usefulness of dexmedetomidine to prevent emergence agitation in a patient with Krabbe disease: a case report," JA Clinical Reports (2018) 4:34, 4 pages.
Sakurai et al., "Buccal administration of dexmedetomidine as a preanesthetic in children," Journal of Anesthesia, 2010, 24:49-53.
Santana and Mills, "Retrospective study of intranasal dexmedetomidine as a prophylactic against emergence delirium in pediatric patients undergoing ear tube surgery." International Journal of Pediatric Otorhinolaryngology (2017); 100: 39-43.
Santangelo, et al., "Transnasal administration of a combination of dexmedetomidine, midazolam and butorphanol produces deep sedation in New Zealand White rabbits." Veterinary Anaesthesia and Analgesia (2016); 43 (2): 209- 214.
Santos, et al., "Sedative and cardiorespiratory effects of dexmedetomidine and buprenorphine administered to cats via oral transmucosal or intramuscular routes." Veterinary Anaesthesia and Analgesia (2010); 37 (5): 417-424.
Santos, et al., "Effects of intramuscular dexmedetomidine in combination with ketamine or alfaxalone in swine." Veterinary Anaesthesia and Analgesia (2016); 43 (1): 81-85.
Sato, et al., "Effect of single-dose dexmedetomidine on emergence agitation and recovery profiles after sevoflurane anesthesia in pediatric ambulatory surgery." Journal of Anesthesia (2010); 24(5): 675-682.
Savla, et al., "Effect of intranasal dexmedetomidine or oral midazolam premedication on sevoflurane EC50 for successful laryngeal mask airway placement in children: a randomized, double-blind, placebo-controlled trial." Pediatric Research (2014); 24 (4): 433-439.
Sazuka et al., "Dexmedetomidine dose dependently decreases oral tissue blood flow during sevoflurane and propofol anesthesia in rabbits," Journal of Oral and Maxillofacial Surgery, 2012, 70(8): 1808-1814.
Scheinin, et al., "Intramuscular Dexmedetomidine as Premedication for General Anesthesia: A Comparative Multicenter Study." Anesthesiology (1993); 78: 1065-1075.
Scheinin, et al., "Pharmacodynamics and pharmacokinetics of intramuscular dexmedetomidine." Clinical Pharmacology & Therapeutics (1992); 52(5): 537-546.
Schmidt, et al., "Effects of preanesthetic administration of midazolam, clonidine, or dexmedetomidine on postoperative pain and anxiety in children." Pediatric Anesthesia (2007); 17(7): 667-674.
Schnellbacher, et al., "The Efficacy of Intranasal Administration of Dexmedetomidine and Ketamine to Yellow-Bellied Sliders (Trachemys scripta scripta)." Journal of Herpetological Medicine and Surgery (2012); 22 (3-4): 91-98.
Segovia, et al., "Pre-anaesthetic medication with intranasal dexmedetomidine and oral midazolam as an anxiolytic. A clinical trial." Analesdepediatria (2013); 81 (4): 226-231.
Sethi, et al., "Conscious sedation in a psychiatric patient: A challenge." J Anaesthesiol Clin Pharmacol. (2017); 33(3): 416-417.
Shah, et al., "Physiologic and biochemical effects of electroacupuncture combined with intramuscular administration of dexmedetomidine to provide analgesia in goats." American Journal of Veterinary Research (2016); 77 (3): 252-259.
Shams and El-Masry, "Ketofol-Dexmedetomidine combination in ECT: A punch for depression and agitation." Indian Journal of Anaesthesia (2014); 58(3): 275-280.
Sharan et al., "A comparison of dexmedetomidine with propofol versus esmolol with propofol to attenuate the hemodynamic stress responses after electroconvulsive therapy," Indian J Psychiatry, Jul.-Sep. 2017;59(3): 366-369.
Shehabi, et al., "The effect of dexmedetomidine on agitation during weaning of mechanical ventilation in critically ill patients." Anaesthesia and Intensive Care (2010); 38 (1): 82-90.
Sheta, et al., "Intranasal dexmedetomidine vs midazolam for premedication in children undergoing complete dental rehabilitation: a double-blinded randomized controlled trial." Pediatric Anesthesia (2014); 24 (2): 181-189.
Shetty and Aggarwal, "Efficacy of Intranasal Dexmedetomidine for Conscious Sedation in Patients Undergoing Surgical Removal of Impacted Third Molar: A Double-Blind Split Mouth Study." Journal of Maxillofacial and Oral Surgery (2016); 15 (4): 512-516.
Shi, et al., "Intranasal Dexmedetomidine in Termination of First Trimester Pregnancy of Suction Evacuation." J Anesth Clin Res (2017); 8 (11): 1000781, 7 pages.
Singh et al., "A comparative evaluation of analgo-sedative effects of oral dexmedetomidine and ketamine: a triple-blind, randomized study," Anesthesia 24 (2014) 1252-1259.
Singla, et al., "Comparison of dexmedetomidine versus midazolam for intranasal premedication in children posted for elective surgery: a double-blind, randomised study." Southern African Journal of Anaesthesia and Analgesia (2015); 21 (6):154-157.
Sivrikaya, et al., "Intranasal Dexmedetomidine Versus Midazolam Premedication in Paediatric Patients: A Prospective Study." Ecronicon Anaesthesia (2015); 2 (3): 139-147.
Slingsby, et al., "Thermal antinociception after dexmedetomidine administration in cats: a comparison between intramuscular and oral transmucosal administration." J Feline Med Surg. (2009); 11(10): 829-834.
Sobel, et al., "Intramuscular administration of human tissue-type plasminogen activator in rabbits and dogs and its implications for coronary thrombolysis." Circulation (1987); 75 (6): 1261-1272.
Song, et al., "Dexmedetomidine Injection during Strabismus Surgery Reduces Emergence Agitation without Increasing the Oculocardiac Reflex in Children: A Randomized Controlled Trial." PLoS One (2016); 11(9): e0162785, 12 pages.
Spalink, et al., "Intranasal dexmedetomidine for adrenergic crisis in familial dysautonomia." Clinical Autonomic Research (2017); 27 (4): 279-282.
Srinivasa, et al., "Study of Dexmedetomidine as intramuscular premedication in outpatient cataract surgery: A placebo—controlled study." IAIM (2016); 3(2): 60-68.
Staines, R., "BioXcel to trial Apple Watch-drug combination to prevent Alzheimer's agitation episodes," PharmaPhorum, Sep. 19, 2019, 2 pages, retrieved from: https://pharmaphorum.com/news/bioxcel-to-trial-apple-watch-drug-combination-to-prevent-alzheimers-agitation-episodes/.

(56) References Cited

OTHER PUBLICATIONS

Su et al., "Dexmedetomidine for prevention of delirium in elderly patients after non-cardiac surgery: a randomised, double-blind, placebo-controlled trial," Lancet 2016; 388: 1893-1902.

Sulton, et al., "The Use of Intranasal Dexmedetomidine and Midazolam for Sedated Magnetic Resonance Imaging in Children: A Report From the Pediatric Sedation Research Consortium." Pediatric Emergency Care (2017); 00: 00-00, 5 pages, Published Ahead of Print.

Sun et al., "Dexmedetomidine inhibits astrocyte pyroptosis and subsequently protects the brain in in vitro and in vivo models of sepsis," Cell Death and Disease (2019) 10:167, 13 pages.

Sun, et al., "Low-Dose Intramuscular Dexmedetomidine as Premedication: A Randomized Controlled Trial." Med Sci Monit (2014); 20: 2714-2719.

Sundaram and Mathian, "A Comparative Evaluation of Intranasal Dexmedetomidine and Intranasal Midazolam for Premedication in Children: A Double Blind Randomised Controlled Trial." JIDA (2011); 5 (7): 777-781.

Sutcliffe, et al., "Efficacy of Selective PDE4D Negative Allosteric Modulators in the Object Retrieval Task in Female Cynomolgus Monkeys (*Macaca fascicularis*)." PLoS One (2014); 9 (7): e102449, pp. 1-16.

Talon, et al., "Intranasal Dexmedetomidine Premedication is Comparable With Midazolam in Burn Children Undergoing Reconstructive Surgery." Journal of Burn Care & Research (2009); 30 (4): 599-605.

Tammam and Wahba, "Quality of MRI pediatric sedation: Comparison between intramuscular and intravenous dexmedetomidine." Egyptian Journal of Anaesthesia (2013); 29: 47-52.

Tammam, "Comparison of the efficacy of dexmedetomidine, ketamine, and a mixture of both for pediatric MRI sedation." Egyptian Journal of Anaesthesia (2013); 29(3): 241-246.

Tang et al., "Dexmedetomidine Controls Agitation and Facilitates Reliable, Serial Neurological Examinations in a Non-Intubated Patient with Traumatic Brain Injury," Neurocrit Care., 2011;15(1):175-181 (Published online: Mar. 3, 2010).

Tang, et al., "Intranasal Dexmedetomidine on Stress Hormones, Inflammatory Markers, and Postoperative Analgesia after Functional Endoscopic Sinus Surgery." Mediators of Inflammation (2015); Article ID 939431, 9 pages.

Tang et al., "The effect of intranasal administration of dexmedetomidine to assist local anesthesia in patients with endoscopic nasal surgery," Chinese Journal of Anesthesiology, 2016, 36(2), English abstract only, 4 pages.

Tayari, et al., "Methadone and Dexmedetomidine Combination as Premedicant Agents for Ovariectomy in Cats." American Journal of Animal and Veterinary Sciences (2015); 10 (2): 101-111.

Tazeroualti, et al., "Oral clonidine vs midazolam in the prevention of sevoflurane-induced agitation in children. A prospective, randomized, controlled trial." British Journal of Anaesthesia (2007); 98 (5): 667-671.

Tetef, S., "Effectiveness of Transmucosal Sedation for Special Needs Populations in the Ambulatory Care Setting," AORN Journal, Dec. 2014, 100(6):651-669.

Tobi et al., "Emergence Delirium in a Schizophrenic Patient who Underwent Craniotomy for Elevation of Depressed Skull Fracture under General Anaesthesia: A Case Report," International Journal for Case Reports, 2018, vol. 2, No. 2:8, 3 pages.

Tobias, J.D., "Dexmedetomidine to Control Agitation and Delirium from Toxic Ingestions in Adolescents." J Pediatr Pharmacol Ther. (2010); 15(1): 43-48.

Tobias, J.D., "Dexmedetomidine to treat opioid withdrawal in infants following prolonged sedation in the pediatric ICU," J Opioid Manag., 2006;2(4):201-205.

Tobias, J.D., "Subcutaneous dexmedetomidine infusions to treat or prevent drug withdrawal in infants and children," Journal of Opioid Management, 2008, 4(4):187-191.

Tomita et al., "The Effect of Dexmedetomidine on Oral Mucosal Blood Flow and the Absorption of Lidocaine," Anesth Prog 2018, 65: 168-176.

Trevisan et al., "Intranasal dexmedetomidine and intravenous ketamine for procedural sedation in a child with alpha-mannosidosis: a magic bullet?" Italian Journal of Pediatrics (2019) 45:119, 6 pages.

Tug, et al., "Comparison of Two Different Intranasal Doses of Dexmedetomidine in Children for Magnetic Resonance Imaging Sedation." Paediatr Drugs (2015); 17 (6): 479-485.

UK Competent Authority, Chemicals Regulation Directorate, Health and Safety Executive, United Kingdom "CLH report, Proposal for Harmonised Classification and Labelling Based on Regulation (EC) No. 1272/2008 (CLP Regulation), Annex VI, Part 2, Substance Name: Medetomidine," CLH Report for Medetomidine, Version No. 1, Oct. 2014, pp. 1-64.

UMIN-CTR Clinical Trial Identifier: UMIN000020446, Intranasal Premedication with Dexmedetomidine and midazolam in ophthalmic surgery for pediatrics, are they really equally effective? Mansoura Faculty of Medicine, mansoura university, Date of disclosure of study Feb. 1, 2016, Last modified Jan. 5, 2016, Registered Jan. 5, 2016, https://upload.umin.ac.jp/cgi-open-bin/ctr_e/ctr_view.cgi?recptno=R000023623, downloaded May 5, 2018, 5 pages.

Upadhyay et al., "Dexmedetomidine Infusion to Facilitate Opioid Detoxification and Withdrawal in a Patient with Chronic Opioid Abuse," Indian Journal of Palliative Care, Sep.-Dec. 2011, vol. 17, Issue 3, p. 251-254.

Upadhyay et al., "Prolonged dexmedetomidine infusion to facilitate drug detoxification and withdrawal in patients with multiple drugs addiction," Crit Care & Shock (2011) 14:84-88.

Uusalo et al., "Feasibility of Intranasal Dexmedetomidine in Treatment of Postoperative Restlessness, Agitation, and Pain in Geriatric Orthopedic Patients," Drugs & Aging (2021) vol. 38, pp. 441-450.

Uusalo et al., "Pharmacokinetics and Sedative Effects of Intranasal Dexmedetomidine in Ambulatory Pediatric Patients," Anesth Analg. Apr. 2020; 130(4):949-957.

Vega et al., "Prevention of Opioid Withdrawal Syndrome After Pediatric Heart Transplantation: Usefulness of Dexmedetomidine," Scientific Letters/Rev Esp Cardiol, 2013;66(7):593-595.

Virkkil, et al., "Dexmedetomidine as intramuscular premedication for day-case cataract surgery." Anesthesia, 1994, pp. 853-858.

Virkkil, et al., "Dexmedetomidine as intramuscular premedication in outpatient cataract surgery," Anesthesia, 1993, pp. 482-487.

Walsh, et al., "Use of intranasal dexmedetomidine for preoperative sedation in the pediatric population: a case series." Anesthesiology 2008; 109, A1378, 1 page.

Wang et al., "Comparison of Intranasal Dexmedetomidine and Oral Midazolam for Premedication in Pediatric Dental Patients under General Anesthesia: A Randomised Clinical Trial," BioMed Research International, 2020, vol. 2020, Article ID 5142913, 7 pages.

Wang et al., "Effects of dexmedetomidine nasal spray on preoperative sedation and analgesia and postoperative agitation in children with ventricular septal defect closure," Chinese Journal of Experimental Surgery, 2016, 33(3), English abstract only, 4 pages.

Wang et al., "Pharmacokinetics of Intranasally Administered Dexmedetomidine in Chinese Children," Front. Pharmacal., Jul. 2019, 10:756, 9 pages.

Wang, et al., "The sedative effects and the attenuation of cardiovascular and arousal responses during anesthesia induction and intubation in pediatric patients: a randomized comparison between two different doses of preoperative intranasal dexmedetomidine." Paediatr Anaesth (2014); 24 (3): 275-281.

Whittington et al., "Dexmedetomidine increases tau phosphorylation under normothermic conditions in vivo and in vitro," Neurobiology of Aging (2015) 36: 2414-2428.

Whittington et al., "Dexmedetomidine induces tau hyperphosphorylation in the mouse hippocampus," Alzheimer's & Dementia, Jul. 2012, vol. 8, Issue 4, Supplement, pp. P461-P462.

Wikipedia, Bipolar I Disorder, Mar. 30, 2018, 5 pages.

Wilson et al., "The Psychopharmacology of Agitation: Consensus Statement of the American Association for Emergency Psychiatry Project BETA Psychopharmacology Workgroup," West J Emerg Med. 2012;13(1):26-34.

Winstock et al., "Should I stay or should I go? Coming off methadone and buprenorphine treatment," International Journal of Drug Policy (2011) 22:77-81.

(56) References Cited

OTHER PUBLICATIONS

Wong and Freeman, "Cutaneous allergic reaction to intramuscular vitamin K1." Australian Journal of Dermatology (1999); 40 (3): 147-152.
Wu et al., "Annual Prevalence of Diagnosed Schizophrenia in the USA: A Claims Data Analysis Approach," Psychological Medicine 2006, pp. 1535-1540.
Wu et al., "Efficacy and safety of intravenous dexmedetomidine in adjuvant general anesthesia," Chinese Journal of Anesthesiology, 2007, Issue 9, 773-776, English abstract only, 4 pages.
Wu, et al., "Intranasally Administered Adjunctive Dexmedetomidine Reduces Perioperative Anesthetic Requirements in General Anesthesia." Yonsei Med J (2016); 57 (4): 998-1005.
Wu et al., "Neuroprotective effect of dexmedetomidine in a murine model of traumatic brain injury," Scientific Reports, (2018) 8:4935, 10 pages.
Xu et al., "ED50 of dexmedetomidine nasal drip in induction of hypnosis in children during computed tomography," Zhonghua Yi Xue Za Zhi. Jun. 24, 2014;94(24):1886-8, English abstract only.
Xu, et al., "Effects of dexmedetomidine on the recovery profiles from general anesthesia in patients undergoing endoscopic sinus surgery." Int J Clin Exp Med (2016); 9(5): 8405-8410.
Xu et al., "Effects of Two Intranasal Dexmedetomidine Doses as Premedication on Sevoflurane EC 50 for Successful Laryngeal Mask Airway Placement in Children," Zhongguo Yi Xue Ke Xue Yuan Xue Bao. Dec. 20, 2016;38(6):627-631, English abstract only.
Xu et al., "Efficacy and Safety of Intranasal Dexmedetomidine During Recovery From Sevoflurane Anesthesia in Children: A Systematic Review and Meta-analysis," Clin Neuropharmacol, 2021; 44:157-168.
Yamane et al., "Effect of Dexmedetomidine Injected Into the Oral Mucosa in Combination With Lidocaine on Local Anesthetic Potency in Humans: A Crossover Double-Blind Study," J Oral Maxillofac Surg, 2015 73:616-621.
Yang et al., "Analysis of 17 948 pediatric patients undergoing procedural sedation with a combination of intranasal dexmedetomidine and ketamine," Paediatr Anaesth., 2019; 29(1):85-91.
Yang et al., "Effect of dexmedetomidine on postoperative cognitive dysfunction and inflammation in patients after general anaesthesia, A PRISMA-compliant systematic review and meta-analysis," Medicine (2019) 98:18(e15383), 10 pages.
Yang et al., "Fifty Percent Effective Dose of Intranasal Dexmedetomidine Sedation forT ransthoracic Echocardiography in Children With Cyanotic and Acyanotic Congenital Heart Disease," Journal of Cardiothoracic and Vascular Anesthesia (2020), 34, 966-971.
Yao, et al., "Intranasal dexmedetomidine premedication reduces minimum alveolar concentration of sevoflurane for laryngeal mask airway insertion and emergence delirium in children: a prospective, randomized, doubleblind, placebocontrolled trial." Pediatric Anesthesia (2015); 25 (5): 492-498.
Yingyi, et al., "ED50 of dexmedetomidine nasal drip in induction of hypnosis in children during computed tomography." Zhonghua Yi Xue Za Zhi (2014); 94(24): 1886-1888 (with English Abstract).
Yuen, et al., "A Comparison of Intranasal Dexmedetomidine and Oral Midazolam for Premedication in Pediatric Anesthesia: A Double-Blinded Randomized Controlled Trial." Anesthesia & Analgesia (2008); 106 (6): 1715-1721.
Yuen, et al., "A Double-Blind, Crossover Assessment of the Sedative and Analgesic Effects of Intranasal Dexmedetomidine." Anesthesia & Analgesia (2007); 105 (2): 374-380.
Yuen, et al., "A randomised comparison of two intranasal dexmedetomidine doses for premedication in children." Anaesthesia (2012); 67 (11): 1210-1216.
Yuen, et al., "Optimal timing for the administration of intranasal dexmedetomidine for premedication in children." Anaesthesia (2010); 65 (9): 922-939.
Yun, et al., "Effects of intranasal dexmedetomidine for children undergoing cleft lip and palate repair surgery." International Journal of Somatology (2016); 43 (4): 401-405 (with English Abstract).
Zhang, et al., "Median Effective Dose of Intranasal Dexmedetomidine for Rescue Sedation in Pediatric Patients Undergoing Magnetic Resonance Imaging." Anesthesiology (2016); 125 (6): 1130-1135.
Zhang et al., "The Effect of Dexmedetomidine on Cognitive Function and Protein Expression of A, p-Tau, and PSD95 after Extracorporeal Circulation Operation in Aged Rats," Hindawi BioMed Research International, Jan. 2018, vol. 2018, Article ID 4014021, 8 pages.
Zhang et al., "The Safety and Efficacy of Intranasal Dexmedetomidine During Electrochemotherapy for Facial Vascular Malformation: A Double-Blind, Randomized Clinical Trial," J Oral Maxillofac Surg, 2013 71:1835-1842.
Zheng et al., "Administration of Dexmedetomidine inhibited NLRP3 inflammasome and microglial cell activities in hippocampus of traumatic brain injury rats," Bioscience Reports, Accepted Manuscript, Sep. 19, 2018, 29 pages.
Zornow, et al., "Dexmedetomidine Decreases Cerebral Blood Flow Velocity in Humans." Journal of Cerebral Blood Flow & Metabolism (1993); 13(2): 350-353.
Zub et al., "Preliminary experience with oral dexmedetomidine for procedural and anesthetic premedication," Pediatric Anesthesia 2005 15: 932-938.
Abdel-Ghaffar, H. S., et al., "Oral trans-mucosal dexmedetomidine for controlling of emergence agitation in children undergoing tonsillectomy: a randomized controlled trial", Revista Brasileira de Anestesiologia (2019); 69(5): 469-476.
Aikaterini, A., et al. "Bradycardia leading to asystole following dexmedetomidine infusion during cataract surgery: dexmedetomidine-induced asystole for cataract surgery", Case Reports in Anesthesiology (2018); 2018(2896032); 2 pages.
Aravindhanthan, V., et al., "Sublingual spray: a new technology oriented formulation with multiple benefits", International Journal of Research in Pharmaceutical Sciences (2019); 10(4): 2875-2885.
Author Unknown, Assessment Report ([Trade Name] Precedex Injection 200μg [Abott] and [Maruishi], Date of Application: Dec. 7, 2001), Oct. 22, 2003, p. 1-57.
Bala, R., et al., "Orally dissolving strips: A new approach to oral drug delivery system", International Journal of Pharmaceutical Investigation (2013); 3(2): 67-76.
Barr, J., et al., "Clinical practice guidelines for the management of pain, agitation, and delirium in adult patients in the intensive care unit", Critical Care Medicine (2013); 41(1): 263-306.
Batandier, C., et al., "Acute stress delays brain mitochondrial permeability transition", Journal of Neurochemistry (2014); 131: 314-322.
Bharati, S., et al., "Incidence of cardiac arrest increases with the indiscriminate use of dexmedetomidine: a case series and review of published case reports", Acta Anaesthesiologica Taiwanica (2011); 49(4): 165-167.
BioXcel Therapeutics, Inc., "BioXcel Therapeutics Announces FDA Approval of IGALMI™ (dexmedetomidine) Sublingual Film for Acute Treatment of Agitation Associated with Schizophrenia or Bipolar I or II Disorder in Adults", Press Release (Apr. 6, 2022); 5 pages.
BioXcel Therapeutics, Inc., "BioXcel Therapeutics Reports Second Quarter 2018 Financial Results and Provides Business Update," Globe Newswire, Aug. 8, 2018, 3 pages, retrieved from: https://ir.bioxceltherapeutics.com/press-releases/detail/49/bioxcel-therapeutics-reports-second-quarter-2018-financial.
Blevins, T., et al., "Effects of acute and chronic ethanol exposure on heteromeric N-methyl-d-aspartate receptors expressed in HEK 293 cells", Journal of Neurochemistry (1997); 69(6): 2345-2354.
Boyer J et al., "Treating Agitation With Dexmedetomidine in the ICU," Dimensions of Critical Care Nursing, 2009, vol. 28(3), pp. 102-109.
Brandt, J., "The Hopkins Verbal Learning Test: Development of a new memory test with six equivalent forms", The Clinical Neuropsychologist (1991); 5(2): 125-142.
Browning, M., et al., "A single dose of citalopram increases fear recognition in healthy subjects", Journal of Psychopharmacology (2007); 21(7): 684-690.
Center for Drug Evaluation and Research, Application No. 21-038, Medical Review(s), Drug Name: Precedex (dexmedetomidine hcl injection), Dec. 18, 1998, 183 pages.

(56) References Cited

OTHER PUBLICATIONS

Center for Drug Evaluation and Research, Application No. 215390, Multi-Discipline Review, Drug Name: IGALMI (dexmedetomidine hydrochloride orally dissolving film), Mar. 1, 2021, 159 pages.
Charney, et al., "The psychobiology of resilience and vulnerability to anxiety disorders: implications for prevention and treatment". Dialogues Clin Neurosci. Sep. 2003; 5(3): 207-221.
Citrome, L., et al., "Sublingual Dexmedetomidine for Agitation Associated with Schizophrenia or Bipolar Disorder: A Post Hoc Analysis of Number Needed to Treat, Number Needed to Harm, and Likelihood to be Helped or Harmed", Advances in Therapy (Oct. 2022); 39: 4821-4835.
ClinicalTrials.gov Identifier: NCT02836431, Pharmacokinetic Study of Dexmedetomidine After Intra-nasal Dosing in Children, First Posted—Jul. 19, 2016, Last Update Posted—Jul. 30, 2018, retrieved from https://clinicaltrials.gov/ct2/show/NCT02836431, 8 pages.
ClinicalTrials.gov Identifier: NCT02955732, Pharmacological Characteristics of Intranasally Given Dexmedetomidine in Paediatric Patients (PINDEX), First Posted Nov. 4, 2016, Last Update Posted—Sep. 12, 2018, retrieved from https://clinicaltrials.gov/ct2/show/NCT02955732, 5 pages.
ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—May 18, 2021, retrieved from https://clinicaltrials.gov/ct2/show/study/NCT03668951, 8 pages.
ClinicalTrials.gov Identifier: NCT04010305, Sub-Lingual Dexmedetomidine in Agitation Associated With Schizophrenia, First Posted—Jul. 8, 2019, Access Date—Jun. 9, 2023, retrieved from https://clinicaltrials.gov/ct2/show/NCT04010305, 9 pages.
ClinicalTrials.gov Identifier: NCT04268303, Dexmedetomidine in the Treatment of Agitation Associated With Schizophrenia (Serenity I), First Posted—Feb. 13, 2020; Access Date Apr. 27, 2023, retrieved from https://clinicaltrials.gov/ct2/show/NCT04268303; 9 pages.
ClinicalTrials.gov Identifier: NCT04276883, Dexmedetomidine in the Treatment of Agitation Associated With Bipolar Disorder (Serenity II), First Posted—Feb. 19, 2020, Access Date—May 30, 2023, retrieved from https://clinicaltrials.gov/ct2/show/NCT04276883, 21 pages.
Co-pending U.S. Appl. No. 17/628,021, inventors Kakumanu; Vasukumar et al., filed Jan. 18, 2022.
De Assis Brasil, E. S., et al., "The blockade of the serotoninergic receptors 5-HT5A, 5-HT6 and 5-HT7 in the basolateral amygdala, but not in the hippocampus facilitate the extinction of fear memory", Behavioural Brain Research (2019); 372: 112055, 7 pages.
Detke and Lucki, "Active behaviors in the rat forced swimming test differentially produced by serotonergic and noradrenergic antidepressants". Psychopharmacology (Berl). Sep. 1995; 121(1): 66-72.
D'Orazi, F. T., et al., "Citalopram/opiate alkaloids Serotonin syndrome, treated with dexmedetomidine: case report", Reactions Weekly, Nov. 2015,; 1579(1): 117.
Ely, E. W., et al., "Monitoring sedation status over time in ICU patients: reliability and validity of the Richmond Agitation-Sedation Scale (RASS)", Jama (2003); 289(22): 2983-2991.
Extended European Search Report for European Patent Application No. 20844019.8, dated Mar. 31, 2023, 19 pages.
Flaquer, A., et al., "Mitochondrial genetic variants identified to be associated with posttraumatic stress disorder", Translational Psychiatry (2015); 5: e524; 7 pages.
Gerlach, A. T., et al., "Dexmedetomidine-associated bradycardia progressing to pulseless electrical activity: case report and review of the literature", Pharmacotherapy: The Journal of Human Pharmacology and Drug Therapy (2009); 29: 392e-398e.
Gertler, et al., Dexmedetomidine: a novel sedative-analgesic agent, BUMC Proceedings, 2001, pp. 13-21.
Gioeni, D., et al., "Oral transmucosal or intramuscular administration of dexmedetomidine-methadone combination in dogs: Sedative and physiological effects", Animals (2020); 10(2057): 1-11.

Glue et al., "Influence of CYP2D6 activity on the pharmacokinetics and pharmacodynamics of a single 20 mg dose of ibogaine in healthy volunteers," The Journal of Clinical Pharmacology, 2015, 20 pages, vol. 55, No. 6.
Gossop, M., "The development of a short opiate withdrawal scale (SOWS)", Addictive Behaviors (1990); 15(5): 487-490.
Gray, M. J., et al., "Psychometric properties of the life events checklist", Assessment (2004); 11(4): 330-341.
Howland, J., et al., "Caffeinated alcoholic beverages: An emerging public health problem", American Journal of Preventive Medicine (2011); 40(2): 268-271.
Hsiao, J. K., "Sublingual dexmedetomidine as a potential new treatment for agitation", JAMA (Feb. 22, 2022); 327(8); 723-725.
Igalmi (dexmedetomidine) sublingual film, for sublingual or buccal use, Highlights of Prescribing Information, Jul. 2022; 21 pages.
International Preliminary Report on Patentability in International Application No. PCT/US2015/055828 dated Apr. 18, 2017, 8 pages.
International Preliminary Report on Patentability in International Application No. PCT/US2017/069030, dated Jul. 11, 2019, 7 pages.
International Preliminary Report on Patentability in International Application No. PCT/US2019/039268, dated Jan. 7, 2021, 18 pages.
International Preliminary Report on Patentability in International Application No. PCT/US2019/039308, dated Jan. 7, 2021, 12 pages.
International Preliminary Report on Patentability in International Application No. PCT/US2020/042618 dated Feb. 3, 2022, 19 pages.
International Preliminary Report on Patentability in International Application No. PCT/US2020/051256, dated Mar. 31, 2022, 16 pages.
International Preliminary Report on Patentability in International Application No. PCT/US2021/017857, dated Aug. 25, 2022, 8 pages.
International Preliminary Report on Patentability in International Application No. PCT/US2021/054171, dated Apr. 20, 2023, 13 pages.
International Search Report and Written Opinion, for International Application No. PCT/US2017/069030, dated Feb. 28, 2018, 8 pages.
International Search Report and Written Opinion for International Application No. PCT/US2021/017857 dated Apr. 26, 2021, 9 pages.
International Search Report and Written Opinion for International Application No. PCT/US2022/011130 dated Mar. 16, 2022, 10 pages.
International Search Report and Written Opinion for International Application No. PCT/US2022/017963 dated May 23, 2022, 15 pages.
International Search Report and Written Opinion of the International Searching Authority for International Application No. PCT/US2019/039268, dated Sep. 13, 2019, 20 pages.
International Search Report and Written Opinion of the International Searching Authority for International Application No. PCT/US2019/039308, dated Sep. 13, 2019, 15 pages.
International Search Report and Written Opinion of the International Searching Authority for International Application No. PCT/US2020/042618, dated Mar. 1, 2021, 22 pages.
International Search Report and Written Opinion of the International Searching Authority for International Application No. PCT/US2020/051256, dated Dec. 10, 2020, 18 pages.
International Search Report and Written Opinion of the International Searching Authority for International Application No. PCT/US2021/054171, dated Feb. 15, 2022, 18 pages.
International Search Report, PCT appl. No. PCT/US2015/055828, 4 pages (dated Mar. 1, 2016).
Invitation to Pay Additional Fees in International Application No. PCT/US2015/055828 dated Dec. 9, 2015, 2 pages.
Invitation to Pay Additional Fees in International Application No. PCT/US2020/042618 dated Dec. 22, 2020, 2 pages.
Invitation to Pay Additional Fees in International Application No. PCT/US2021/054171 dated Dec. 15, 2021, 2 pages.
Johnson, B. A., et al., "The Combine Saftee: a structured instrument for collecting adverse events adapted for clinical studies in the alcoholism field", Journal of Studies on Alcohol (2005); Supplement 15: 157-167.

(56) References Cited

OTHER PUBLICATIONS

Keck Jr, P. E., "The management of acute mania", BMJ (2003); 327(7422): 1002-1003.
Kerfoot, K., et al., "Effects of family history of alcohol dependence on the subjective response to alcohol using the intravenous alcohol clamp", Alcoholism: Clinical and Experimental Research (2013); 37(12): 2011-2018.
Kranzler, H. R., et al., "Naltrexone vs. nefazodone for treatment of alcohol dependence: A placebo-controlled trial", Neuropsychopharmacology (2000); 22(5): 493-503.
Lalumiere, R. T., et al., "Post-Training Intra-Basolateral Amygdala Infusions of Norepinephrine Enhance Consolidation of Memory for Contextual Fear Conditioning", The Journal of Neuroscience (Jul. 30, 2003); 23(17): 6754-6758.
Lang, P. J., et al., "Emotional imagery: Conceptual structure and pattern of somato-visceral response", Psychophysiology (1980); 17(2): 179-192.
Lang, P. J., et al., "Fear behavior, fear imagery, and the psychophysiology of emotion: the problem of affective response integration", Journal of Abnormal Psychology (1983); 92(3): 276-306.
Lee et al., "Antioxidant approaches for the treatment of Alzheimer's disease," Expert Rev Neurother. (Jul. 2010); 10(7): 1201-1208.<div id="gtx-trans" style="position: absolute; left: 387px; top: 45.7969px;">.
Lieberman, D. Z., et al., "Separate and concomitant use of lamotrigine, lithium, and divalproex in bipolar disorders", Current Psychiatry Reports (2004); 6(6): 459-465.
Lu, Q., "Modern Traditional Chinese Medicine Formulation Technology", Hubei Science and Technology Press (Sep. 30, 2001); 460-463.
Machida, Nenmaku tekiyou seizai [mucous membrane applying pharmaceutical formulation or mucous membrane application product], New Drug Delivery System, 1st impression, published on (Jan. 31, 2000); p. 77-85.
MacLaren et al., "A randomized, double-blind pilot study of dexmedetomidine versus midazolam for intensive care unit sedation: patient recall of their experiences and short-term psychological outcomes," Journal of Intensive Care Medicine, 2015, vol. 30(3): 167-175.
Martin, C. S., et al., "Development and validation of the biphasic alcohol effects scale", Alcoholism: Clinical and Experimental Research (1993); 17(1): 140-146.
Mello, et al., "Buprenorphine effects on human heroin self-administration: an operant analysis." Journal of Pharmacology and Experimental Therapeutics (Oct. 1982); 223 (1): 30-39.
Miller, et al., "Current Understanding of the Neurobiology of Agitation". West J Emerg Med. Jul. 2020; 21(4): 841-848.
Mohr et al., "Treatment of acute agitation in psychotic disorders," Neuroendocrinology Letters, 2005, vol. 26, No. 4, pp. 327-335.
Morean, M. E., et al., "The drug effects questionnaire: psychometric support across three drug types", Psychopharmacology (2013); 227: 177-192.
Ohmori, T., et al., "Post-operative cardiac arrest induced by co-administration of amiodarone and dexmedetomidine: a case report", Journal of Intensive Care (2015); 3(43): 1-5.
Parmar et al., "A Review on Sublingual Spray: Novel Drug Delivery System," IJPSR, 2017; vol. 8(11): pp. 4533-4539.
Picard et al., "Psychological Stress and Mitochondria: A Systematic Review," Psychosom Med., 2018; 80(2): 141-153.
Precedex Label, Highlights of Prescribing Information, Jun. 2013, 24 pages.
Precedex Label, Highlights of Prescribing Information, Mar. 2016, 23 pages.
Preskorn, et al., "Effect of Sublingual Dexmedetomidine vs Placebo on Acute Agitation Associated With Bipolar Disorder a Randomized Clinical Trial", Jama. Feb. 22, 2022; 327(8): 727-36.
Preskorn, et al., Meeting: Poster Session I—M72. Double-Blind, Placebo-Controlled, Single Ascending Dose, Study to Determine the Efficacy, Safety, and Pharmacokinetics of a BXCL 501 (Sublingual Dexmedetomidine) in Agitation Associated With Schizophrenia or Related Disorders, Neuropsychopharmacology, Oct. 2019, pp. 78-229.
Preskorn, How an Understanding of the Function of the Locus Coeruleus Led to Use of Dexmedetomidine to Treat Agitation in Bipolar Disorder: Example of Rational Development of Psychiatric Medications, Psychopharmacology, Journal of Psychiatric Practice, May 2022, pp. 227-233, vol. 28, No. 3.
Ralevski, E., et al., "Preliminary findings on the interactive effects of IV ethanol and IV nicotine on human behavior and cognition: a laboratory study", Nicotine & Tobacco Research (2012); 14(5): 596-606.
Ray, S., et al., "Acute alcohol effects on repetition priming and word recognition memory with equivalent memory cues", Brain and Cognition (2006); 60(2): 118-127.
Reynolds, B., et al., "Measuring state changes in human delay discounting: an experiential discounting task." Behavioural processes (2004); 67(3): 343-356.
Risinger, et al., M72 double-blind, placebo-controlled, single ascending dose study to determine the efficacy, safety, and pharmacokinetics of BXCL501 (Sublingual Dexmedetomidine) in agitation associated with Schizophrenia or related disorders, BioXcel Therapeutics, ACNP Clinical Poster 2019, 2 pages.
Rosen, M. I., et al., "Neuropsychological correlates of suboptimal adherence to metformin", Journal of Behavioral Medicine (2003); 26: 349-360.
Rossi, G., et al., "Management of agitation in Huntington's disease: A review of the literature", Cureus (2020); 12(8): e9748; 5 pages.
Rothbaum et al., "Early intervention may prevent the development of posttraumatic stress disorder: a randomized pilot civilian study with modified prolonged exposure," Biol Psychiatry (2012); 72: 957-963.
Schweizer, T. A., et al., "Neuropsychological profile of acute alcohol intoxication during ascending and descending blood alcohol concentrations", Neuropsychopharmacology (2006); 31(6): 1301-1309.
Sessler, C. N., et al., "The Richmond Agitation—Sedation Scale: validity and reliability in adult intensive care unit patients", American Journal of Respiratory and Critical Care Medicine (2002); 166(10): 1338-1344.
Shaikh et al., "Mucoadhesive drug delivery systems," J Pharm Bioall Sci 2011;1:89-100.
Sheehan, D. V., et al., "The Mini-International Neuropsychiatric Interview (MINI): the development and validation of a structured diagnostic psychiatric interview for DSM-IV and ICD-10", Journal of Clinical Psychiatry (1998); 59(20): 22-33.
Sinha, R., "How does stress increase risk of drug abuse and relapse?", Psychopharmacology (2001); 158: 343-359.
Sobell, L. C., et al., "Timeline follow-back: A technique for assessing self-reported alcohol consumption", Measuring Alcohol Consumption: Psychosocial and Biochemical Methods (1992): 41-72.
Sofuoglu, M., et al., "Riluzole and d-amphetamine interactions in humans", Progress in Neuro-Psychopharmacology and Biological Psychiatry (2008); 32(1): 16-22.
Sperl et al., "Alpha-2 Adrenoreceptor Antagonist Yohimbine Potentiates Consolidation of Conditioned Fear," Int J Neuropsychopharmacol., 2022, pyac038 (Online ahead of print), 15 pages.
Subramanian, M. G., et al., "A three-stage alcohol clamp procedure in human subjects", Alcoholism: Clinical and Experimental Research (2002); 26(10): 1479-1483.
Surendar, et al., "A comparative evaluation of intranasal dexmedetomidine, midazolam and ketamine for their sedative and analgesic properties: a triple blind randomized study." J Clin Pediatr Dent. (2014); 38 (3): 255-261.
Swift, R. M., et al., "Naltrexone-induced alterations in human ethanol intoxication", The American Journal of Psychiatry (1994); 151(10): 1463-1467.
Upthegrove, R., et al., "Depression and schizophrenia: cause, consequence, or trans-diagnostic issue?", Schizophrenia Bulletin (2017); 43(2): 240-244.
U.S. Appl. No. 16/474,882: Declaration of Dr. W. Douglas Weaver, M.D. with Appendix A, B, C and D, signed May 9, 2023; 120 pages.
U.S. Appl. No. 17/993,422: Declaration of Dr. W. Douglas Weaver, M.D. with Appendix A, signed May 8, 2023; 212 pages.

(56) References Cited

OTHER PUBLICATIONS

Vandael, E., et al., "Risk factors for QTc-prolongation: systematic review of the evidence", International Journal of Clinical Pharmacy (Feb. 2017); 39(1): 16-25. Epub Dec. 23, 2016.

Ward and Citrome, "The treatment of acute agitation associated with schizophrenia or bipolar disorder: investigational drugs in early stages of their clinical development, and their clinical context and potential place in therapy", Expert Opinion on Investigational Drugs, Mar. 2020, 29(3): 245-257.

Weafer, J., et al., "Alcohol-related stimuli reduce inhibitory control of behavior in drinkers", Psychopharmacology (2012); 222: 489-498.

Wesson, D. R., et al., "The clinical opiate withdrawal scale (COWS)", Journal of Psychoactive Drugs (2003); 35(2): 253-259.

Wikipedia, "Young Mania Rating Scale", Dec. 28, 2019 (Dec. 28, 2019), retrieved on Dec. 9, 2021 from https://en.wikipedia.org/w/index.php?title=Young_Mania_Rating_Scale&oldid=932847993; 2 pages.

Written Opinion of the International Searching Authority, PCT appl. No. PCT/US2015/055828, 7 pages (dated Mar. 1, 2016).

Wu et al., "Annual Prevalence of Diagnosed Schizophrenia in the USA: A Claims Data Analysis Approach," Psychological Medicine Nov. 2006; 36(11): 1535-1540. Epub Aug. 15, 2006.

Xu, J., et al., "Assessment of the Effects of Dexmedetomidine on Outcomes of Traumatic Brain Injury Using Propensity Score Analysis", BMC Anesthesiology (Apr. 12, 2022); 22: 280; 8 pages.

Zeller and Citrome, "Managing Agitation Associated with Schizophrenia and Bipolar Disorder in the Emergency Setting". West J Emerg Med. Mar. 2016; 17(2): 165-172. Epub Mar. 2, 2016.

Zhang et al., "Dimebon (Latrepirdine) Enhances Mitochondrial Function and Protects Neuronal Cells from Death," Journal of Alzheimer's Disease (2010); 21(2): 389-402.

Zimmermann, U. S., et al., "Modeling alcohol self-administration in the human laboratory", Behavioral Neurobiology of Alcohol Addiction (2013): 315-353.

International Preliminary Report on Patentability for International Application No. PCT/US2022/011130, dated Jul. 13, 2023, 8 pages.

U.S. Appl. No. 16/474,882: Declaration of Dr. Sheldon Preskorn, M.D. with Appendix A and B, signed Jul. 30, 2023; 58 pages.

U.S. Appl. No. 17/496,470: Declaration of Dr. Sheldon Preskorn, M.D. with Appendix A and B, signed Jul. 29, 2023; 57 pages.

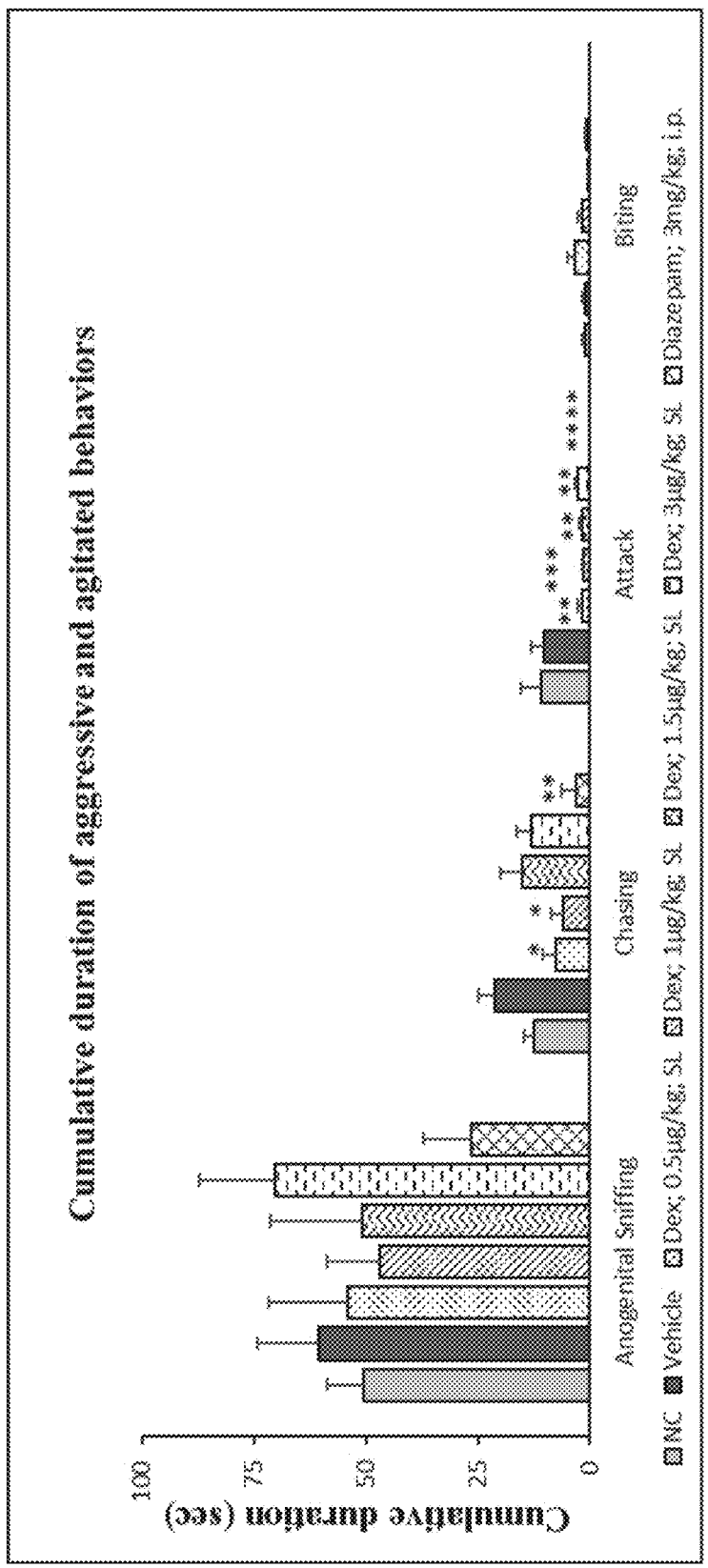
Figure 1A. Effect of sublingually administered Dexmedetomidine hydrochloride (Dex) at varying doses (0.5~ 3 µg/kg) on cumulative duration of aggressive and agitated behaviors. Data expressed as Mean ± SEM. One-way ANOVA followed by Dunnett's post-hoc test. *$p<0.05$ $p<0.01$, *$p<0.001$ and ****$p<0.0001$ vs vehicle controls (vehicle).

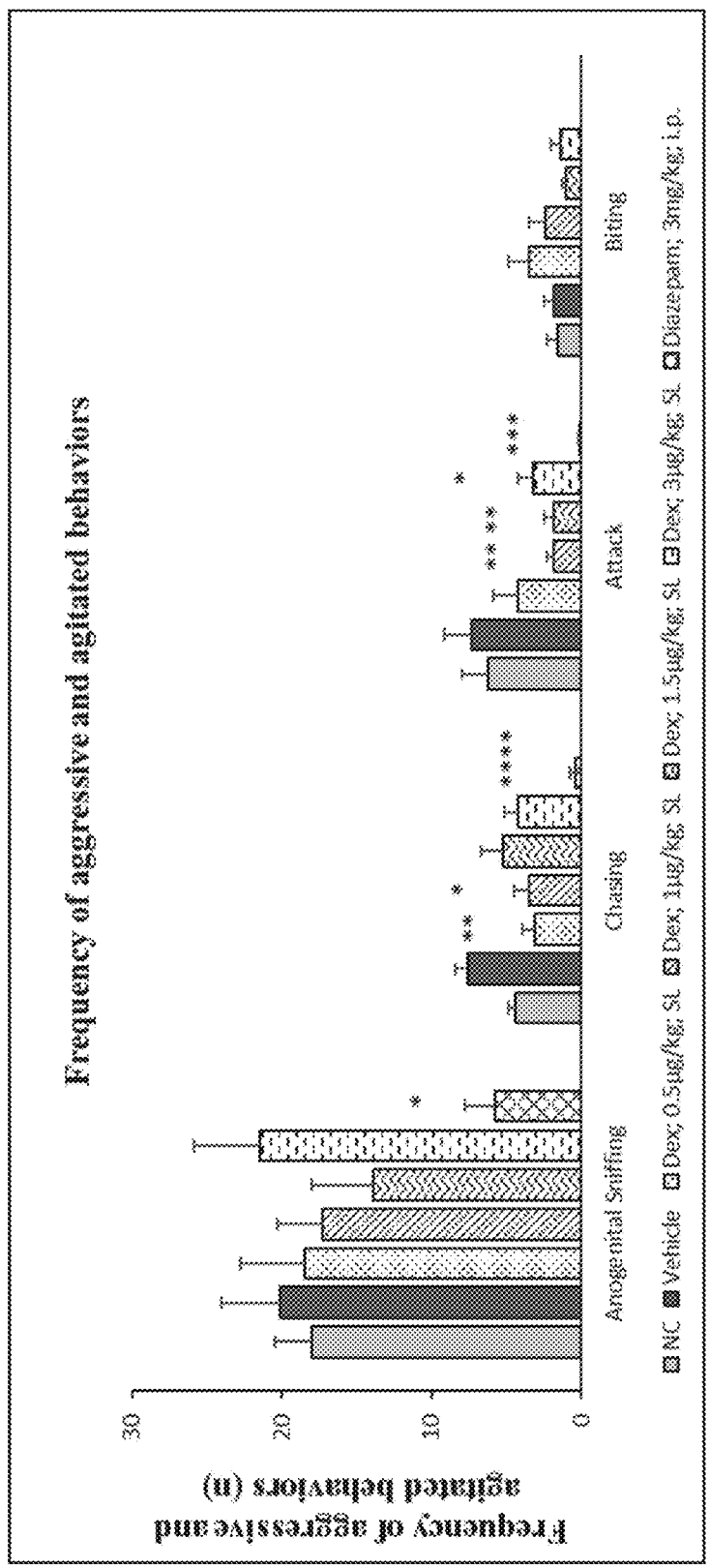
Figure 1B. Effect of sublingually administered Dexmedetomidine hydrochloride (Dex) at varying doses (0.5- 3 µg/kg) on frequency of aggressive and agitated behaviors. Data expressed as Mean ± SEM. One-way ANOVA followed by Dunnett's post-hoc test. $*p<0.05$, $p<0.01$, $*p<0.001$ and $****p<0.0001$ vs vehicle controls (vehicle).

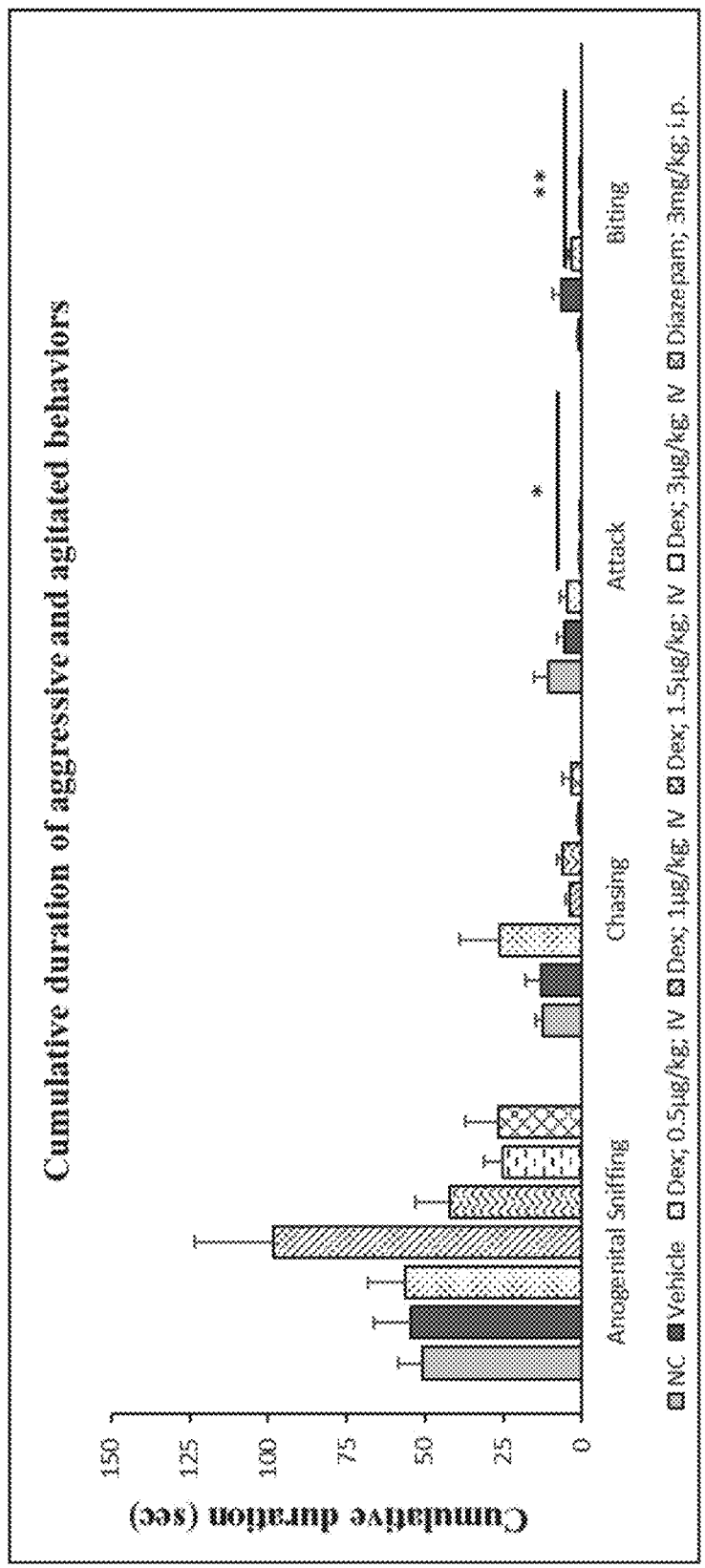
Figure 1C. Effect of intravenously administered Dexmedetomidine hydrochloride (Dex) at varying doses (0.5-3 μg/kg) on cumulative duration of aggressive and agitated behaviors. Data expressed as Mean ± SEM. One-way ANOVA followed by Dunnett's post-hoc test. *$p<0.05$ $p<0.01$, *$p<0.001$ and ****$p<0.0001$ vs vehicle controls (vehicle).

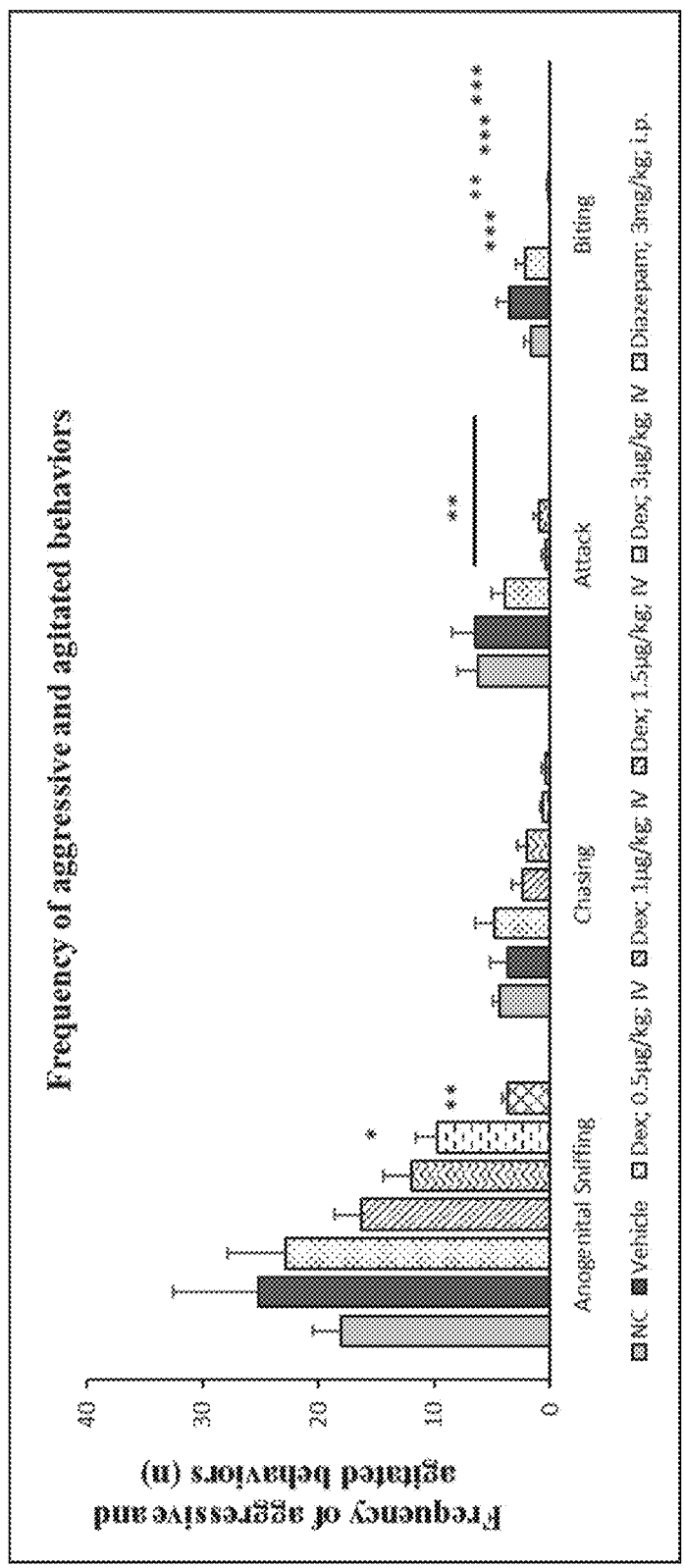
Figure 1D. Effect of intravenously administered Dexmedetomidine hydrochloride (Dex) at varying doses (0.5-3 µg/kg) on frequency of aggressive and agitated behaviors. Data expressed as Mean ± SEM. One-way ANOVA followed by Dunnett's post-hoc test. *$p<0.05$ $p<0.01$, *$p<0.001$ and ****$p<0.0001$ vs vehicle controls (vehicle).

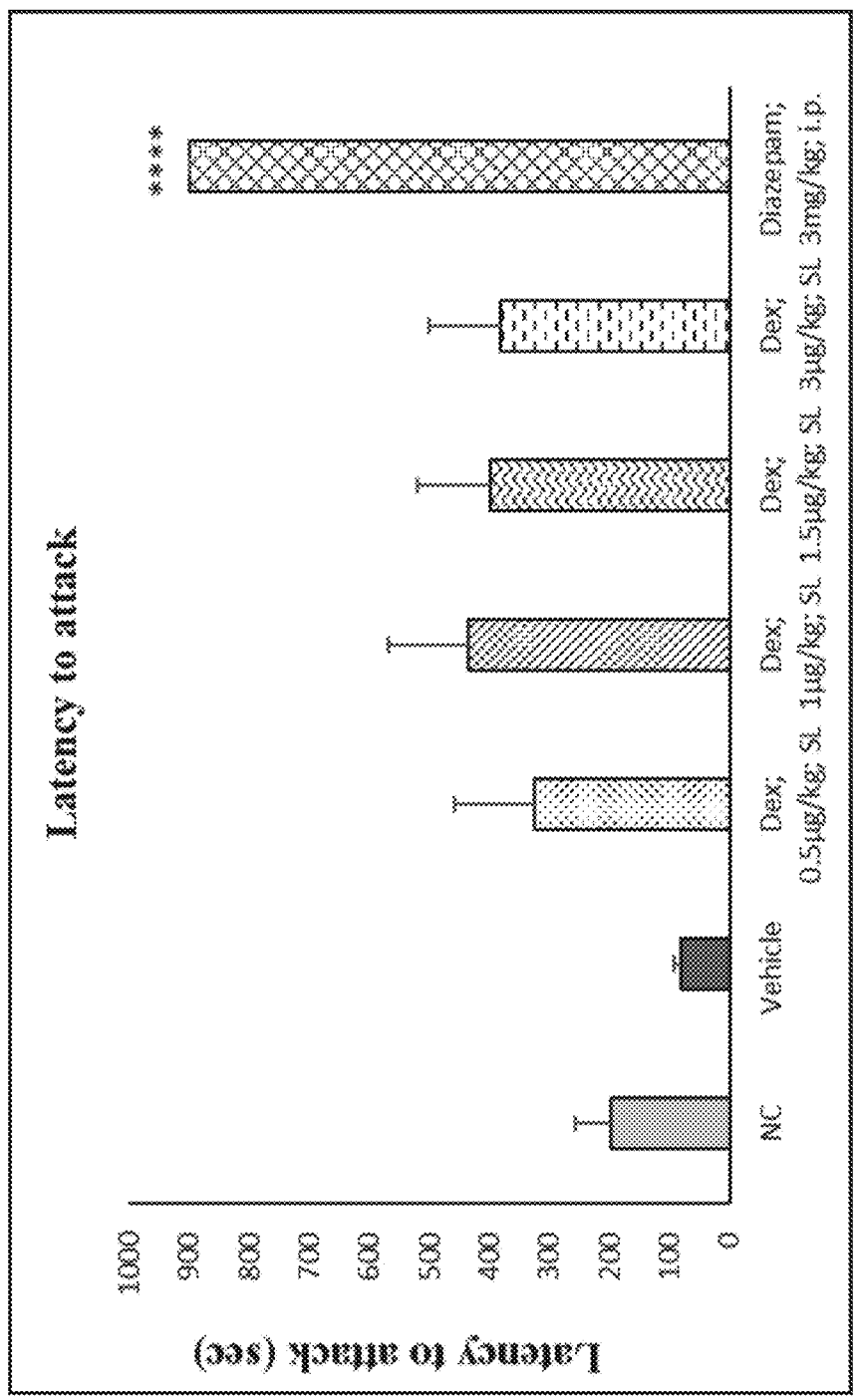
Figure 2A. Effect of sublingually administered Dexmedetomidine hydrochloride (Dex) at varying doses (0.5-3 µg/kg) on Latency to attack. Data is expressed as Mean ± SEM. Statistical analysis was performed by One-way ANOVA followed by Dunnett's post-hoc test. $*p<0.05$ $p<0.01$, $*p<0.001$ and $****p<0.0001$ vs vehicle controls (vehicle).

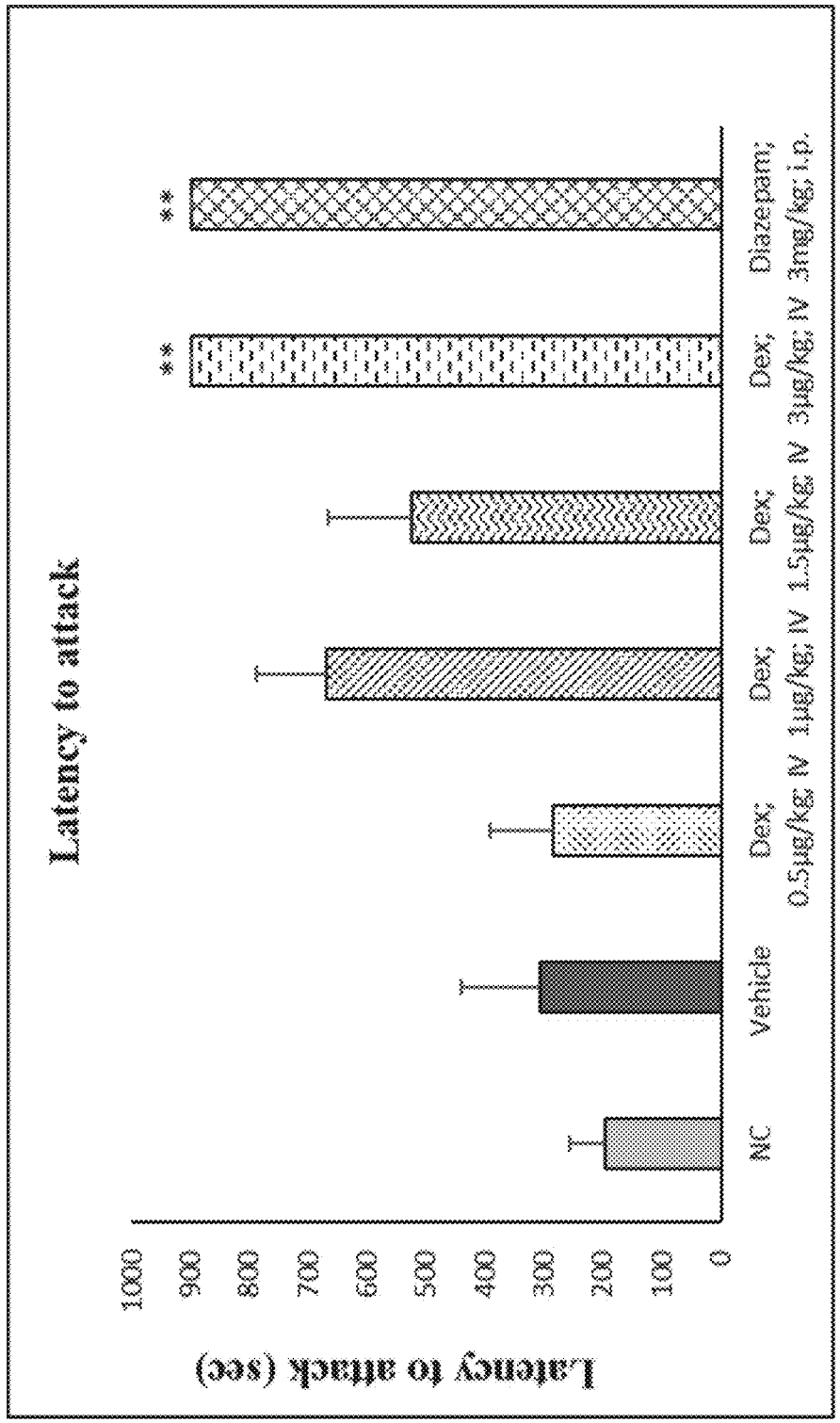
Figure 2B. Effect of intravenously administered Dexmedetomidine hydrochloride (Dex) at varying doses (0.5-3 μg/kg) on Latency to attack. Data is expressed as Mean ± SEM. Statistical analysis was performed by One-way ANOVA followed by Dunnett's post-hoc test. *p<0.05 p<0.01, *p<0.001 and ****p<0.0001 vs vehicle controls (vehicle).

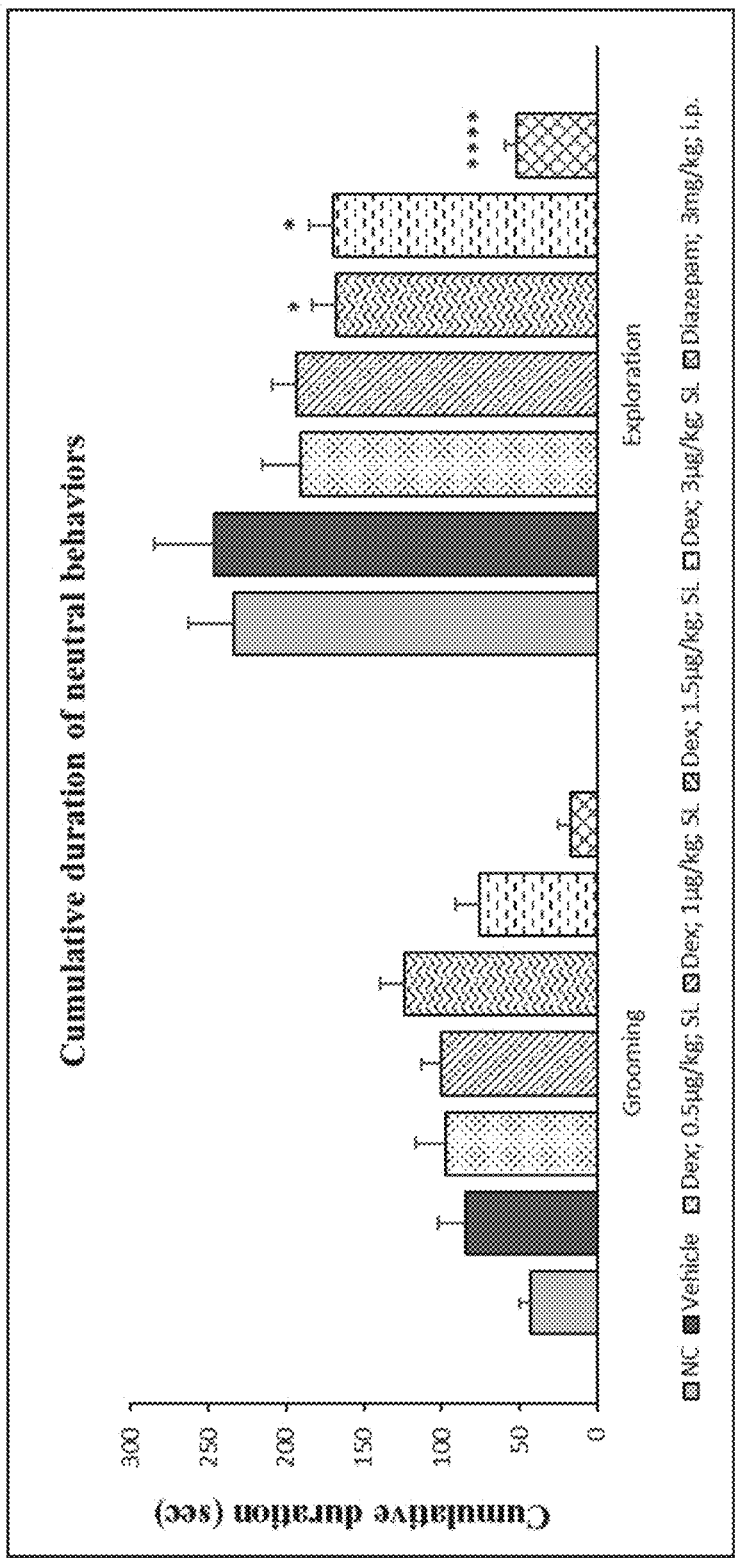

Figure 3A. Effect of sublingually administered Dexmedetomidine hydrochloride (Dex) at varying doses (0.5-3 μg/kg) on Cumulative duration of Neutral behaviours such as grooming, and exploration. Data expressed as Mean ± SEM. Data is expressed as Mean ± SEM. Statistical analysis was performed by One-way ANOVA followed by Dunnett's post-hoc test. *$p<0.05$ $p<0.01$, *$p<0.001$ and ****$p<0.0001$ vs vehicle controls (vehicle).

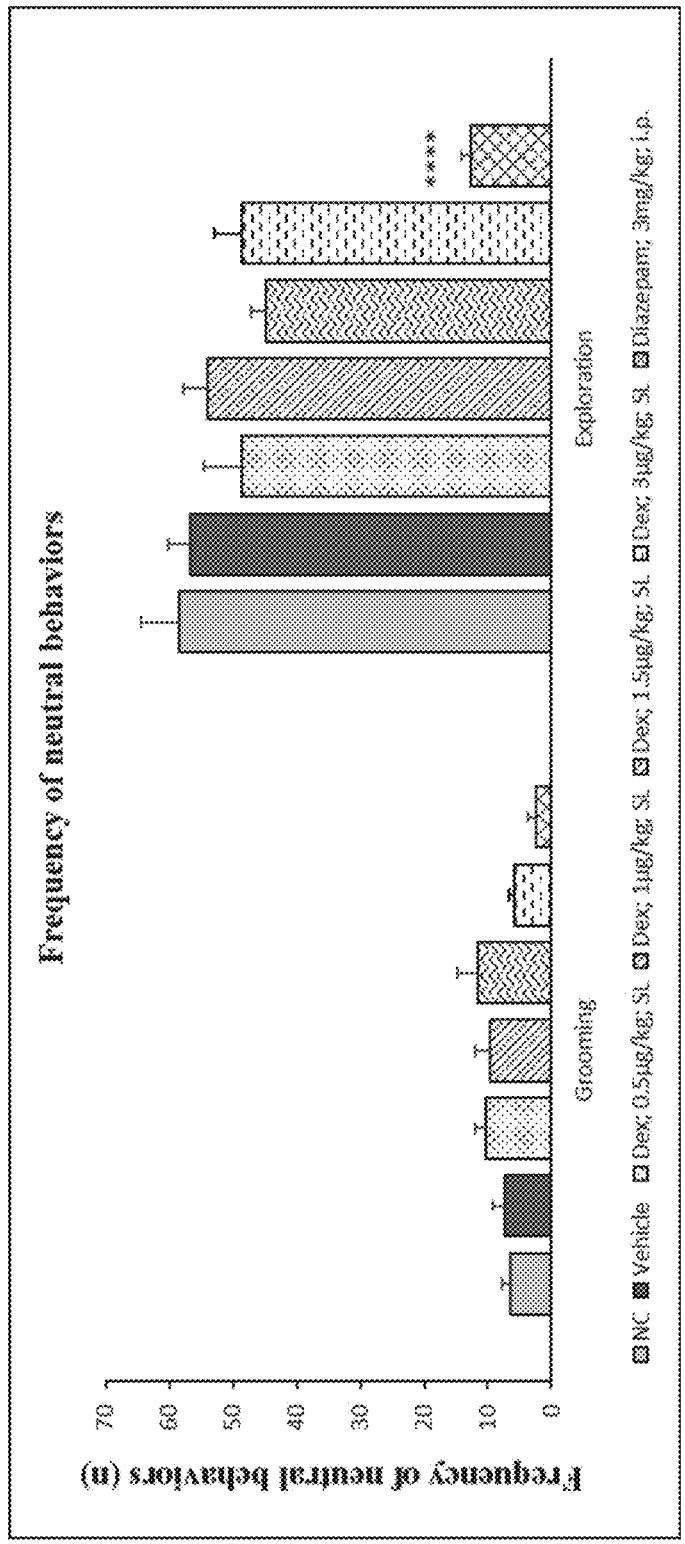

Figure 3B. Effect of sublingually administered Dexmedetomidine hydrochloride (Dex) at varying doses (0.5-3 µg/kg) on Frequency of Neutral behaviours such as grooming, and exploration. Data expressed as Mean ± SEM. Data is expressed as Mean ± SEM. Statistical analysis was performed by One-way ANOVA followed by Dunnett's post-hoc test. *$p<0.05$ $p<0.01$, *$p<0.001$ and ****$p<0.0001$ vs vehicle controls (vehicle).

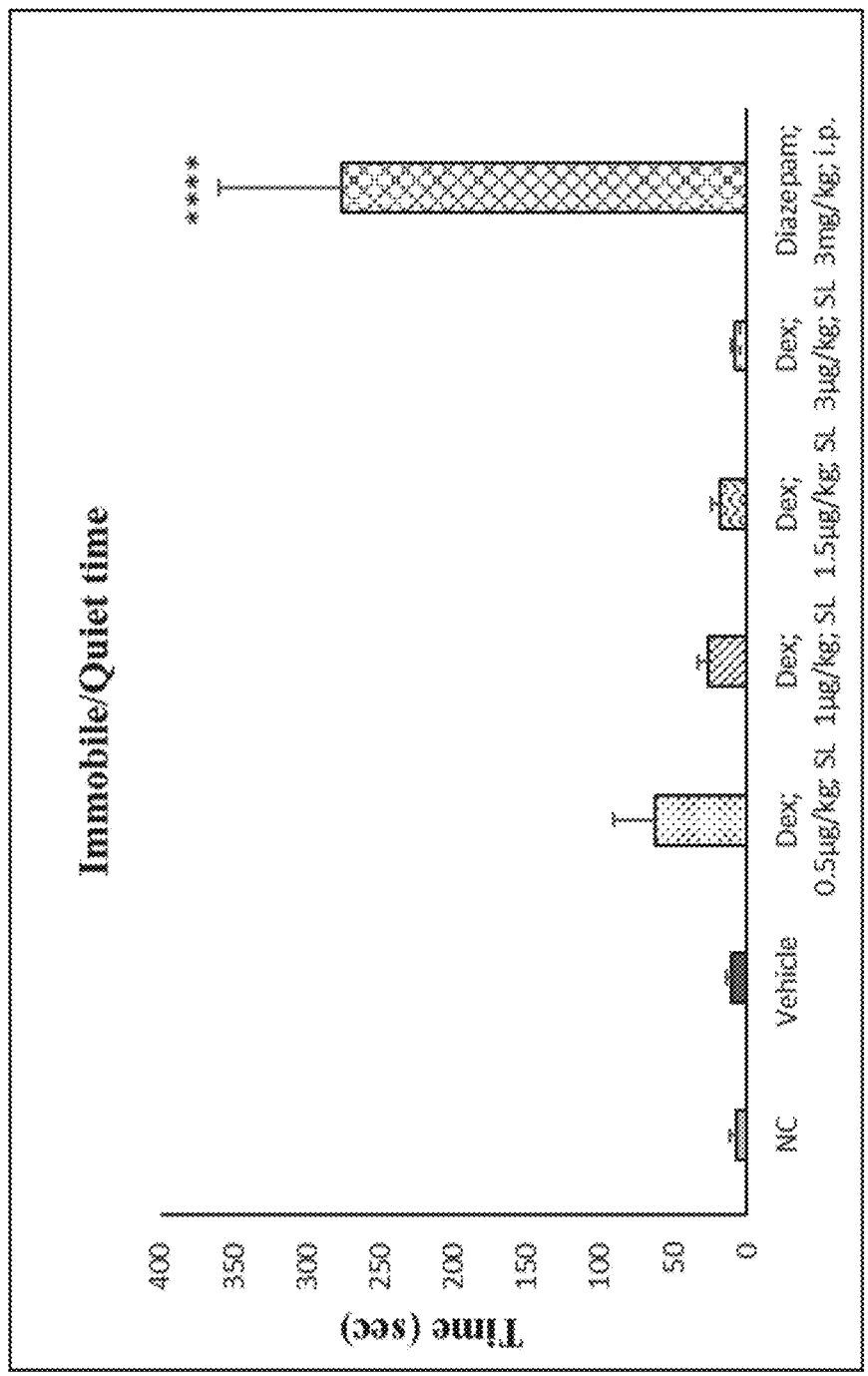
Figure 3C. Effect of sublingually administered Dexmedetomidine hydrochloride (Dex) at varying doses (0.5-3 µg/kg) on Neutral behaviours such as immobile/quiet time. Data expressed as Mean ± SEM. Data is expressed as Mean ± SEM. Statistical analysis was performed by One-way ANOVA followed by Dunnett's post-hoc test. $*p<0.05$ $p<0.01$, $*p<0.001$ and $****p<0.0001$ vs vehicle controls (vehicle).

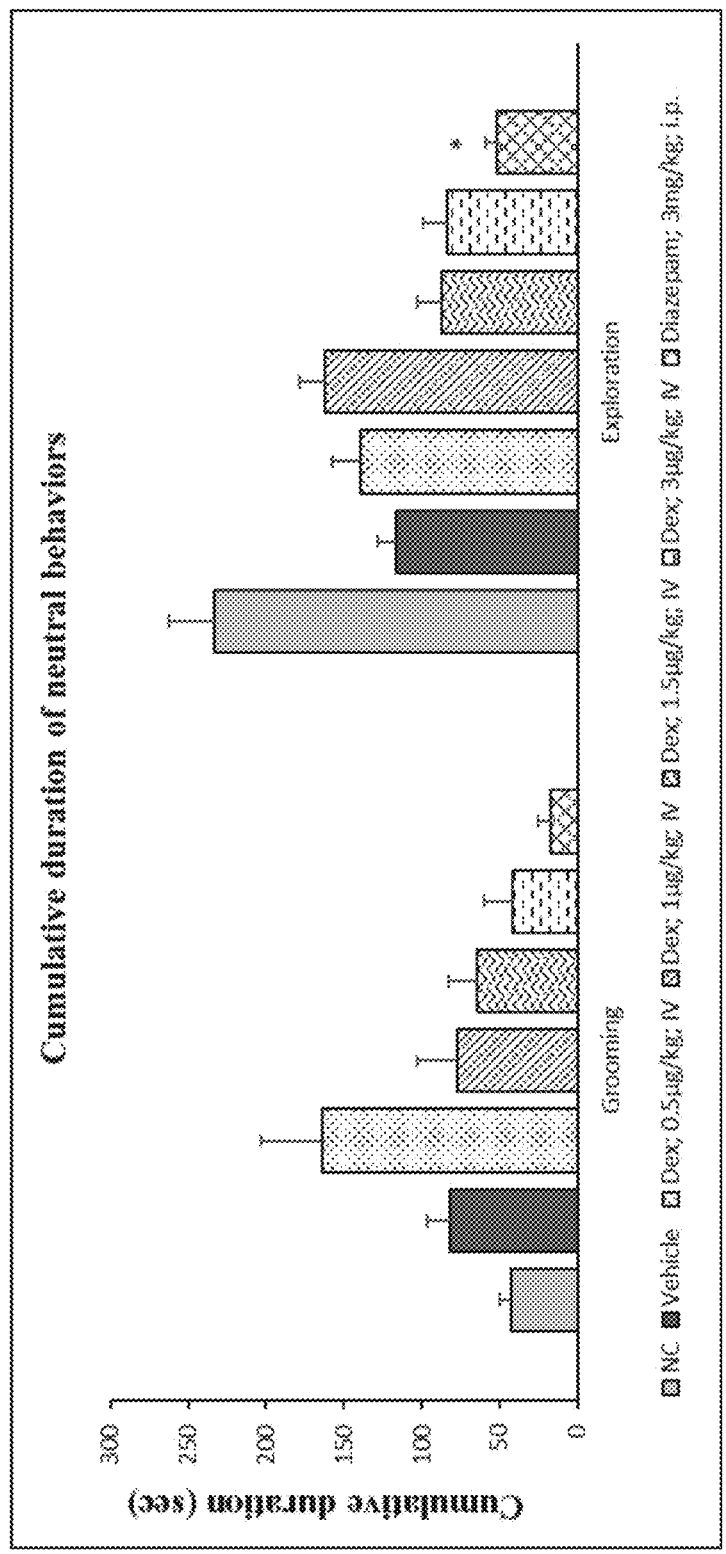

Figure 3D. Effect of intravenously administered Dexmedetomidine hydrochloride (Dex) at varying doses (0.5-3 µg/kg) on Cumulative duration of Neutral behaviours such as grooming, and exploration. Data expressed as Mean ± SEM. Data is expressed as Mean ± SEM. Statistical analysis was performed by One-way ANOVA followed by Dunnett's post-hoc test. *p<0.05 p<0.01, *p<0.001 and ****p<0.0001 vs vehicle controls (vehicle).

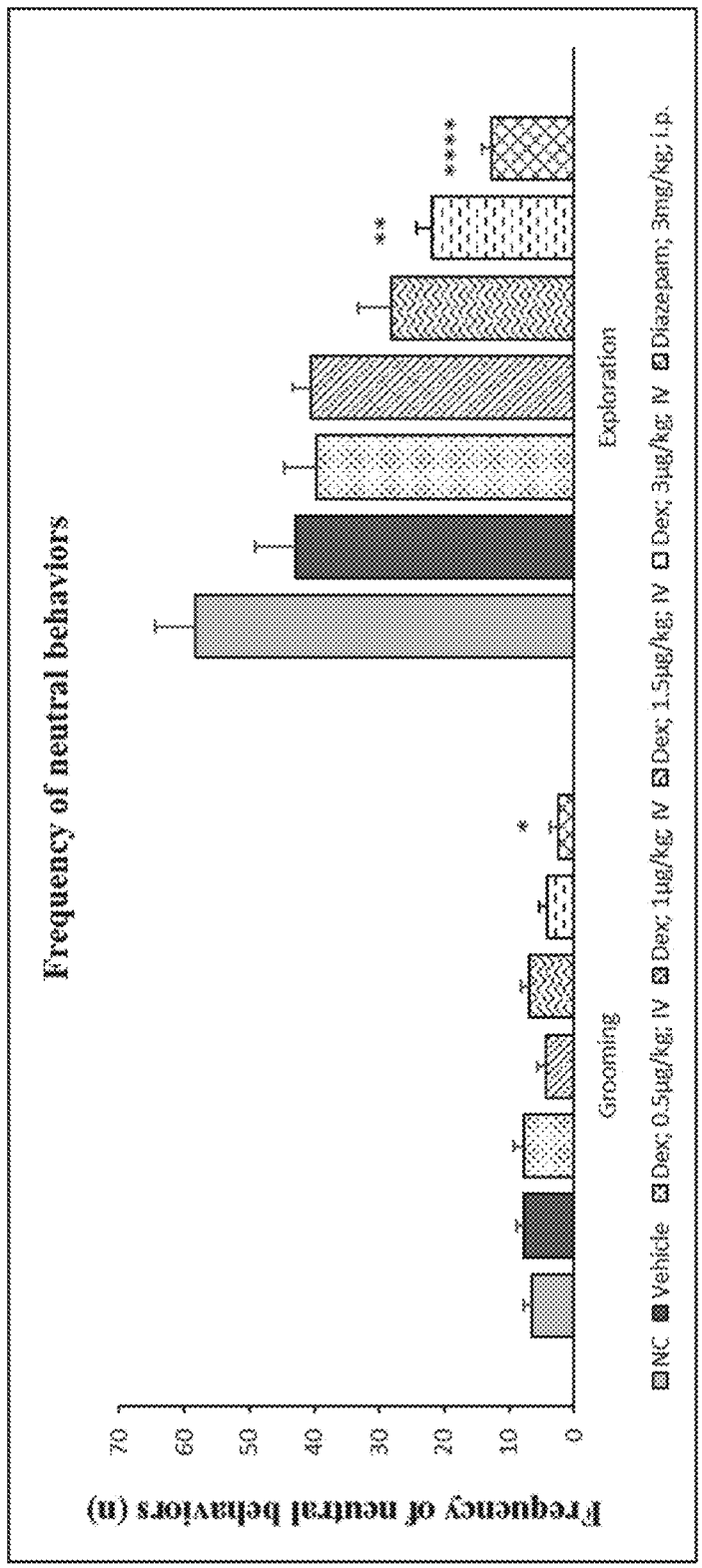
Figure 3E. Effect of intravenously administered Dexmedetomidine hydrochloride (Dex) at varying doses (0.5-3 µg/kg) on Frequency of Neutral behaviours such as grooming, and exploration. Data expressed as Mean ± SEM. Statistical analysis was performed by One-way ANOVA followed by Dunnett's post-hoc test. *p<0.05, p<0.01, *p<0.001 and ****p<0.0001 vs vehicle controls (vehicle).

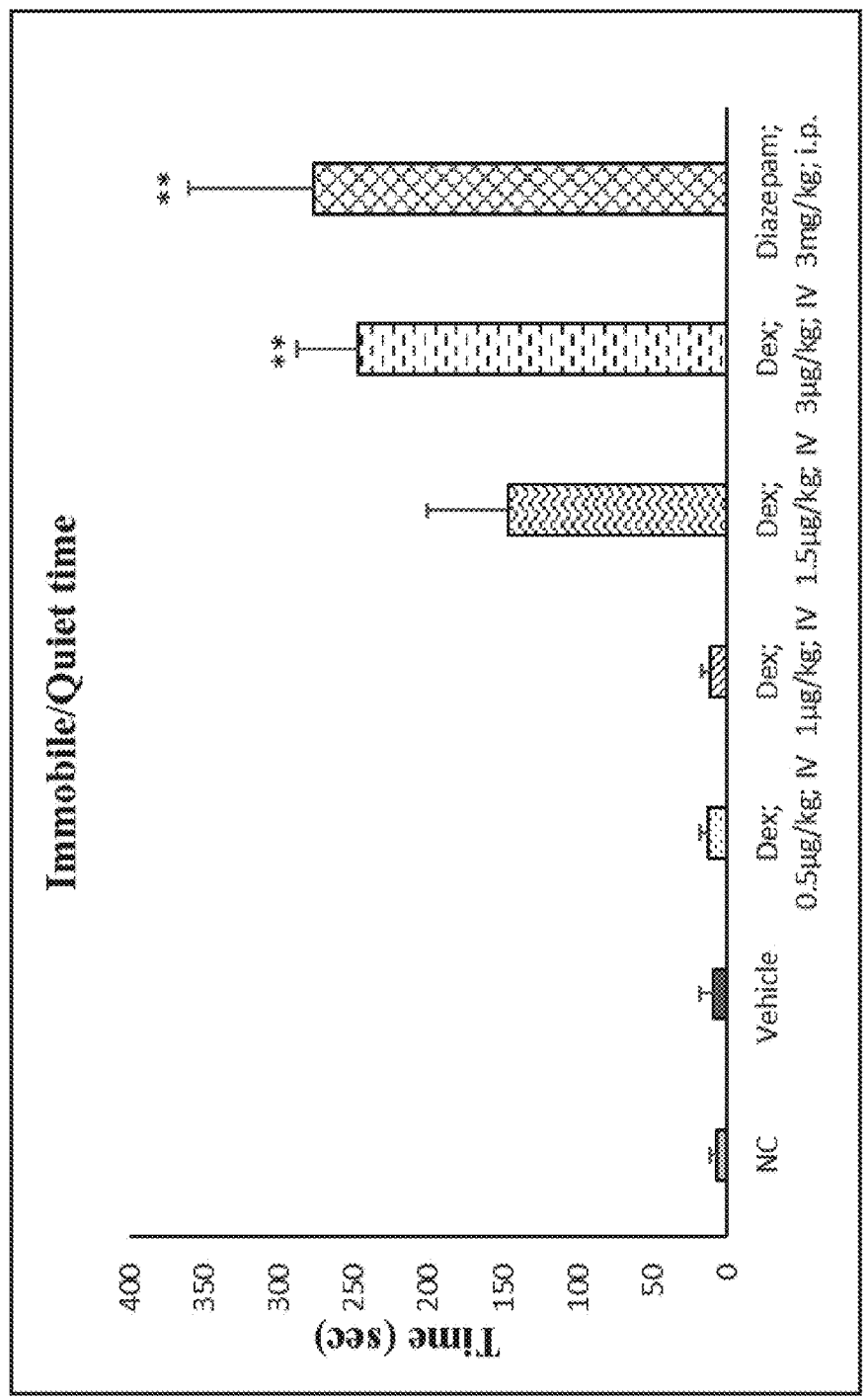
Figure 3F. Effect of intravenously administered Dexmedetomidine hydrochloride (Dex) at varying doses (0.5-3 µg/kg) on Neutral behaviours such as immobile/quiet time. Data expressed as Mean ± SEM. Data is expressed as Mean ± SEM. Statistical analysis was performed by One-way ANOVA followed by Dunnett's post-hoc test. *$p<0.05$ $p<0.01$, *$p<0.001$ and ****$p<0.0001$ vs vehicle controls (vehicle).

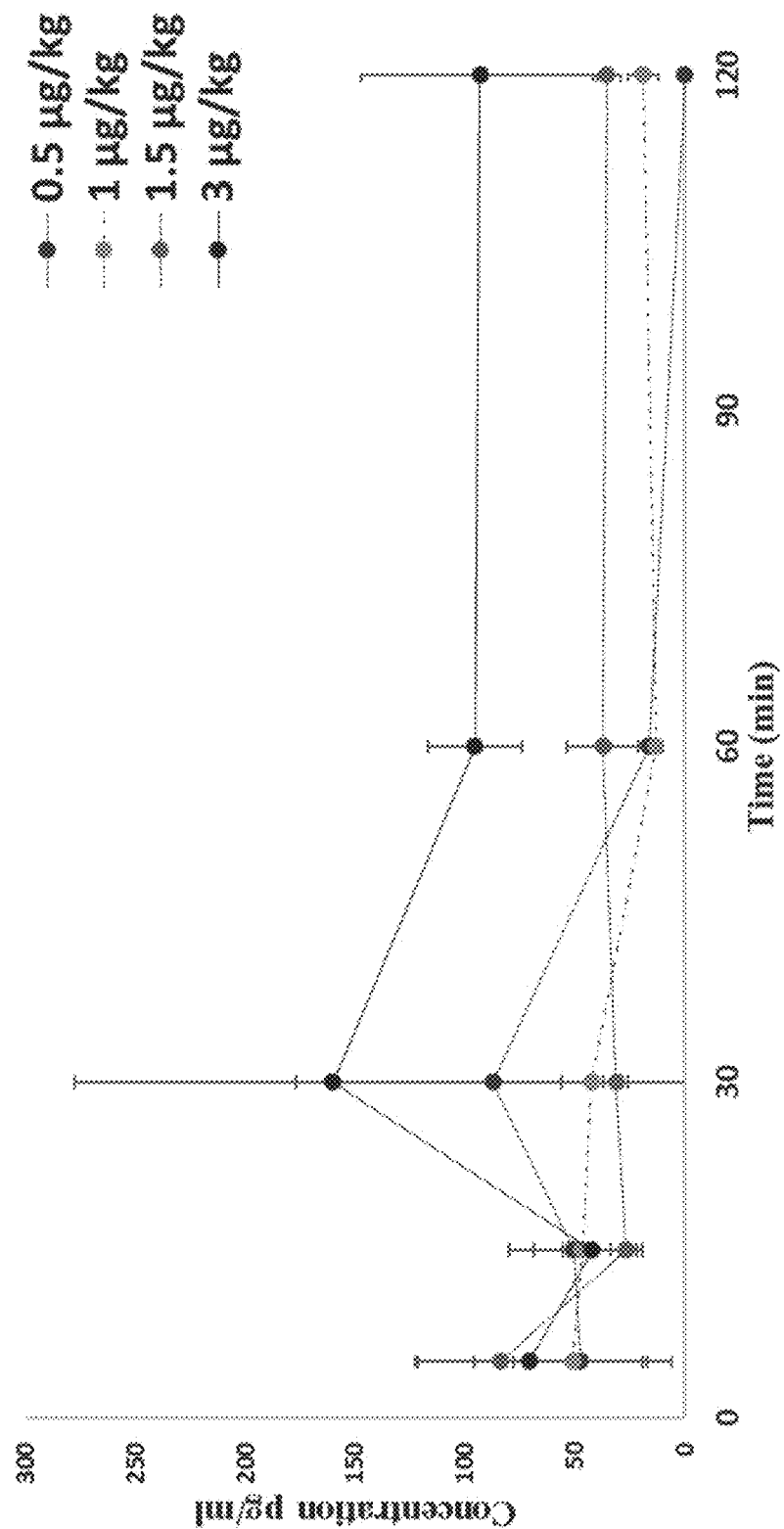
Figure 4A: Mean plasma concentrations following Sublingual (SL) Dexmedetomidine hydrochloride administration in rats. Data expressed as Mean ± SD

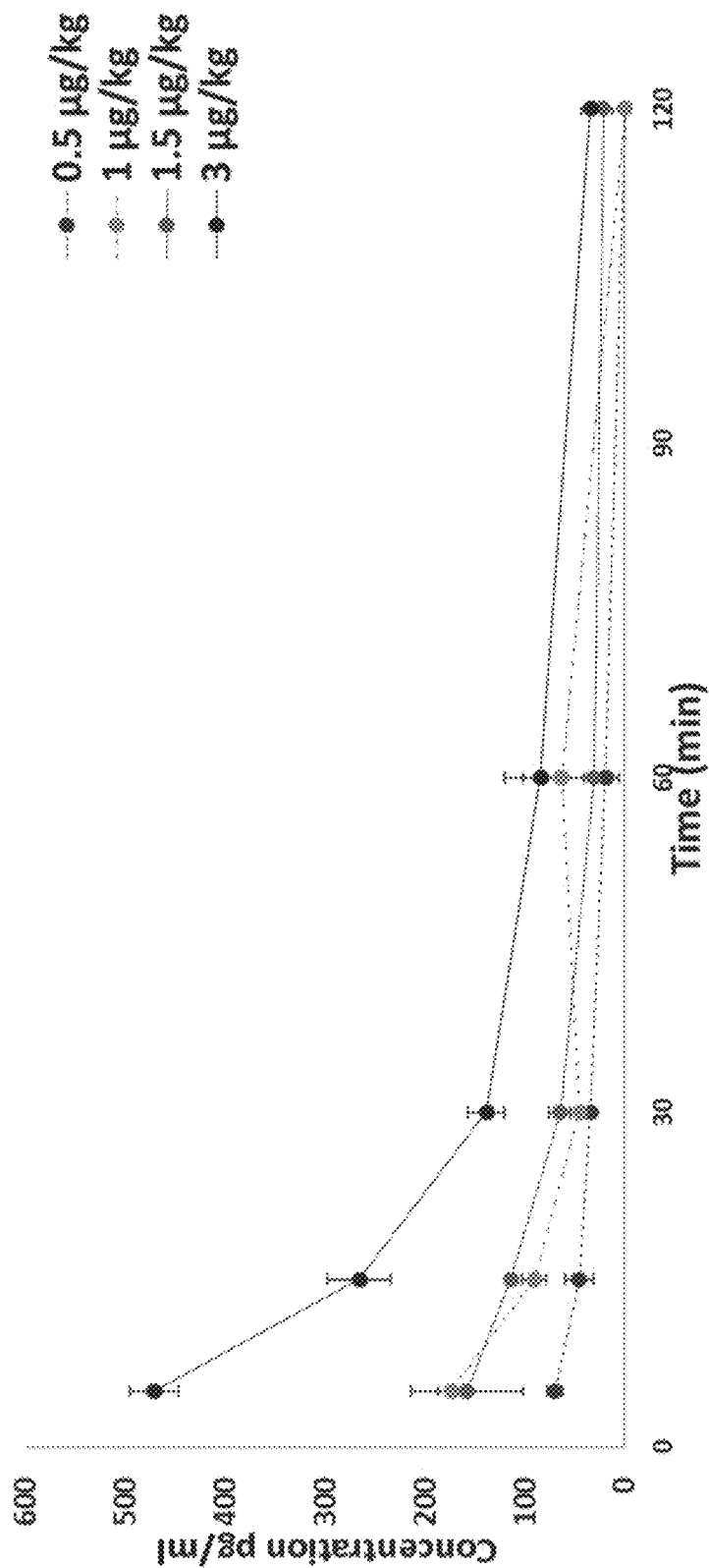
Figure 4B: Mean plasma concentrations following Intravenous (IV) Dexmedetomidine hydrochloride administration in rats. Data expressed as Mean ± SD

USE OF SUBLINGUAL DEXMEDETOMIDINE FOR THE TREATMENT OF AGITATION

CROSS REFERENCE TO RELATED APPLICATION

This application is a continuation of U.S. patent application Ser. No. 16/474,882, filed Jun. 28, 2019, which is a U.S. national stage application of International Patent Application No. PCT/US2017/069030, filed Dec. 29, 2017, which claims the benefit of priority to U.S. Provisional Application No. 62/441,164 filed Dec. 31, 2016, U.S. Provisional Application No. 62/471,393 filed Mar. 15, 2017 and U.S. Provisional Application No. 62/542,323 filed Aug. 8, 2017, the disclosures of which are herein incorporated by reference in their entirety for all purposes.

FIELD OF THE INVENTION

The present invention discloses a method of treating agitation or the signs of agitation in a subject comprising sublingually administering an effective amount of an alpha-2 adrenergic agonist, more particularly Dexmedetomidine or a pharmaceutically acceptable salt thereof. The present invention also discloses a sublingual composition for treating agitation or the signs of agitation comprising an effective amount of Dexmedetomidine or a pharmaceutically acceptable salt thereof together with one or more pharmaceutically acceptable carriers and/or excipients, along with the preparation thereof.

BACKGROUND OF THE INVENTION

Agitation is an umbrella term that can refer to a range of behavioral disturbances or disorders, including aggression, combativeness, hyperactivity, and disinhibition. Agitation is a nonspecific constellation of relatively unrelated behaviors that can be seen in several different clinical conditions, usually presenting a fluctuating course. Agitation may be caused by several different medical conditions and drug interactions or by any circumstances that worsen the person's ability to think. Multiple underlying pathophysiologic abnormalities are mediated by dysregulations of dopaminergic, serotonergic, noradrenergic, and GABAergic systems. Agitation is characterized by non-productive, diffuse and excessive over-activity both motor (akathisia) and cognitive, and accompanied by an inner unpleasant tension. The key to safety is to intervene early to prevent progression of agitation to aggression and violence.

Agitation can be associated with neurodegenerative disorders. One of the important manifestations of long-term progressive neurodegenerative process is clinically known as dementia. Dementias include Alzheimer's disease dementia (AD), Fronto-temporal dementia (FTD), Vascular dementia, Lewy body disease (LBD), and Down dementia. Dementia in adults, gradually destroy a person's memory and ability to learn, reason, make judgments, communicate and carry out daily activities. In later stages, patients may experience changes in personality and behavior, such as anxiety, suspicion, agitation and aggression.

Sebastiaan Engelborghs et al., in Neurochemistry International 2007 November, 52(6): 1052-60, disclosed that, in frontotemporal dementia, increased activity of dopaminergic neurotransmission and altered serotonergic modulation of dopaminergic neurotransmission are associated with agitated and aggressive behavior respectively. Pia Jul et al., in Journal of Alzheimer's disease 2015 September, 49(3):783-95, disclosed that rTg4510 mice exhibited P301L-tau-dependent hyperactivity, and agitation-like phenotypes in these mice may form a correlation to some of the behavioral disturbances observed in advanced Alzheimer's disease (AD) and Frontotemporal dementia (FTD). Nathan Hermann et. al., in Journal of Neuropsychiatry 2004 Aug., 16(3): 261-276, disclosed that a compensatory increase in activity within the noradrenergic system may contribute to the behavioral and psychological symptoms of agitation and aggression in Alzheimer's disease.

Agitation can also be associated with neuropsychiatric conditions such as schizophrenia, bipolar illness such as bipolar disorder or mania, depression, delirium, etc or agitation can be associated with alcohol and substance abuse withdrawal. Acute agitation, represented by a state of motor restlessness and accompanying mental tension, is a serious medical problem that can be present in some psychiatric disorders, including schizophrenia and bipolar mania, and may escalate quickly to aggressive behavior. Acute agitation is characterized by signs that include pacing, hand wringing, fist clenching, pressured speech, yelling, and threatening people with escalated agitation.

To date, there is no single medication considered as the "standard of care" for treating agitation in patients with dementia or schizophrenia. Generally, three classes of medications are used most frequently, depending on the severity of the agitation, namely first-generation antipsychotics, second-generation antipsychotics, and benzodiazepines, administered orally, intramuscularly or intravenously. Intramuscular injection of typical antipsychotics and benzodiazepines, given alone or in combination, has been a treatment of choice for agitation over the past few decades. The currently preferred treatment paradigm for acute agitation is to use atypical antipsychotic drugs administered with or without supplemental benzodiazepines.

More specifically, patients with agitation are usually prescribed beta blockers such as propranolol and Pindolol, anxiety medications such as Buspirone, benzodiazepines such as Lorazepam, anti-convulsants such as Valproate and Lamotrigine, anti-psychotics such as Haloperidol, Droperidol, Ziprasidone and other high-potency dopamine-blocking agents, and atypical antipsychotics such as Olanzapine. However, Buspirone, Valproate, Haloperidol, Droperidol and Ziprasidone have potential adverse effects, and optimal dosage and long-term efficacy in the management of chronic agitation in dementia is very limited. Lorazepam is only effective for treating agitation in patients when used before medical procedures. Loxapine (an antipsychotic) is FDA approved for treating agitated patients via inhalation, but is associated with a black box warning for bronchospasm and increased mortality in elderly patients with dementia-related psychosis (FDA label, Loxapine or Adasuve®). Olanzapine, Ziprasidone or its combination with Haloperidol, is also associated with QT prolongation, and extrapyramidal side effects should be watched very carefully in hospital set ups. Reports of adverse events (including eight fatalities) associated with intramuscular olanzapine underscores the need to follow strict prescribing guidelines and avoid simultaneous use with other CNS depressants.

The Expert Consensus Guidelines for treatment of behavioral emergencies cite speed of onset as one of the most important factors in choosing a drug and its route of administration. However, antipsychotic medications can take from days to weeks before having a robust antipsychotic effect. Nevertheless, they do generally have a calming effect on agitated patients within minutes. For example, benzodiazepines or fast-acting sedatives quickly calm a severely agitated patient, but continuous treatment with these drugs leads to tolerance.

Therefore, the treatment of agitation in patients with neuropsychiatric conditions (such as schizophrenia or bipolar mania) and neurodegenerative diseases is still limited because of the potential for significant side effects associated with currently used drugs, their route of administration (intravenous/intramuscular) and the consequent need for hospital set ups for administering these drugs. In an ideal situation, an anti-agitation drug for schizophrenics or dementia patient should have a rapid onset of calming without sedation, be well tolerated and easy to administer with a high safety margin.

Alpha-2 adrenergic agonists have been used therapeutically for a number of conditions, including hypertension, congestive heart failure, angina pectoris, spasticity, glaucoma, diarrhea and for suppression of opiate withdrawal symptoms. Examples of alpha-2 adrenergic agonists include Clonidine, Guanfacine, Guanabenz, Guanoxabenz, Guanethidine, Xylazine, Tizanidine, Medetomidine, Dexmedetomidine, Methyldopa, Methylnorepinephrine, Fadolmidine, Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione. The inventors of the present invention have unexpectedly found that the sub-lingual administration of an alpha-2 adrenergic agonist or a pharmaceutically acceptable salt thereof is a particularly effective and safe intervention for the treatment of agitation.

(S)-4-[1-(2,3-Dimethylphenyl)ethyl]-3H-imidazole(Dexmedetomidine) is commercially available as an injectable formulation for sedation of initially intubated and mechanically ventilated patients during treatment in an intensive care setting, and for non-intubated patients prior to and/or during surgical and other procedures.

Dexmedetomidine is reported to have anti-agitational effects when administered intravenously or buccally during surgical procedures and intensive care unit (ICU) setups. For example, Ibacache et. al., in Anesthesia & Analgesia 2004 January; 98(1):60-3, discloses the administration of an intravenous single-dose of Dexmedetomidine to reduce agitation following sevoflurane anesthesia in children. Other intravenous administrations ar reported by Jeanne Boyer et al., in Nursing Critical care 2010 January, 5(1):30-34, Yahya Shehabi et. al., in Anesthetic Intensive Care 2010 January, 38(1):82-90, and Joseph D. Tobias in Journal of Pediatric Pharmacology Therapeutic, January-March 2010, 15(1): 43-48. NCT 02720705 (clinical trial identification number from clinicaltrials.gov) discloses the administration of trans-buccal Dexmedetomidine for the prevention of emergence agitation in pre-school children treated with sevoflurane in an intensive care unit setting.

The sublingual use of Dexmedetomidine is disclosed in WO 2016/061413. However, the focus of WO 2016/061413 is the administration of Dexmedetomidine sublingually at doses appropriate to treat sleep disorders and induce significant sedation. We have now surprisingly found that Dexmedetomidine or a pharmaceutically acceptable salt thereof, administered sublingually, can effectively treat agitation, including agitation associated with neurodegenerative diseases (e.g. Alzheimer's disease, fronto-temporal dementia, and sundown syndrome in Alzheimer's disease/dementia), agitation associated with neuropsychiatric conditions (e.g. bipolar disorder, schizophrenia, bipolar mania, delirium and depression), agitation associated with alcohol and substance abuse withdrawal or agitation associated with other conditions such as OPD/IPD procedures (e.g. MRI, CT or CAT scan, lumbar puncture, bone marrow aspiration/biopsy, tooth extraction or other dental procedures). The dose to be administered sublingually may be selected to be effective to treat agitation, yet insufficient to causing significant sedation.

SUMMARY OF THE INVENTION

The present invention provides a method of treating agitation or the signs of agitation in a subject in need thereof, comprising administering an effective amount of an alpha-2 adrenergic agonist or a pharmaceutically acceptable salt thereof sublingually to the subject, wherein the said agitation is associated with a neurodegenerative disease like dementia, Alzheimer's disease, frontotemporal dementia, or Parkinsonism, or associated with a neuropsychiatric condition like schizophrenia, bipolar disorder, bipolar mania, delirium, or depression, or associated with an OPD/IPD procedure (e.g. MRI, CT or CAT scan, lumbar puncture, bone marrow aspiration/biopsy, tooth extraction or other dental procedures), or associated with an alcohol and substance abuse withdrawal. In a particular aspect, the agitation is suppressed without also causing significant sedation.

In a preferred aspect, the present invention provides a method of treating agitation or the signs of agitation in a subject in need thereof, comprising administering an effective amount of Dexmedetomidine or a pharmaceutically acceptable salt thereof sublingually to the subject. In a particular aspect, the agitation is suppressed without also causing significant sedation.

Another aspect of the present invention provides a method of treating agitation or the signs of agitation in a subject in need thereof, wherein said agitation is associated with neurodegenerative disease, comprising administering an effective amount of Dexmedetomidine or a pharmaceutically acceptable salt thereof sublingually to the subject. In a particular aspect, the agitation is suppressed without also causing significant sedation.

Yet another object of the present invention provides a method of treating agitation or the signs of agitation in a subject in need thereof, wherein said agitation is associated with dementia, Alzheimer's disease, frontotemporal dementia, Parkinsonism or other neurodegenerative diseases, comprising administering an effective amount of Dexmedetomidine or a pharmaceutically acceptable salt thereof sublingually to the subject. In a particular aspect, the agitation is suppressed without also causing significant sedation.

Another object of the present invention provides a method of treating agitation or the signs of agitation in a subject in need thereof, wherein said agitation is associated with schizophrenia, bipolar disorder, bipolar mania, delirium, depression, or another related neuropsychiatric condition, comprising administering an effective amount of Dexmedetomidine or a pharmaceutically acceptable salt thereof sublingually to the subject. In a particular aspect, the agitation is suppressed without also causing significant sedation.

A further object of the present invention provides a method of treating, preventing or reducing the signs of agitation in a subject in need thereof, wherein said agitation is associated with sundown syndrome in Alzheimer's disease/dementia, comprising administering an effective amount of Dexmedetomidine or a pharmaceutically acceptable salt thereof sublingually to the subject. In a particular aspect, the agitation is suppressed without also causing significant sedation.

Yet another objective of the present invention provides a method for treating agitation or the signs associated with agitation in a subject in need thereof, wherein said agitation is associated with an OPD/IPD procedure (e.g., MRI, CT or CAT scan, lumbar puncture, bone marrow aspiration/biopsy, tooth extraction or other dental procedures), comprising administering an effective amount of Dexmedetomidine or a pharmaceutically acceptable salt thereof sublingually to the subject. In a particular aspect, the agitation is suppressed without also causing significant sedation.

Yet another objective of the present invention provides a method for treating agitation or the signs associated with agitation in a subject in need thereof, wherein said agitation is associated with an alcohol and substance abuse withdrawal, comprising administering an effective amount of Dexmedetomidine or a pharmaceutically acceptable salt thereof sublingually to the subject. In a particular aspect, the agitation is suppressed without also causing significant sedation.

A further aspect of the present invention provides a sublingual composition for treating agitation or the signs of agitation in a subject in need thereof, wherein said agitation is associated with a neurodegenerative disease, and said sublingual composition comprises an effective amount of Dexmedetomidine or a pharmaceutically acceptable salt thereof, together with one or more pharmaceutical acceptable carriers and/or excipients.

Another aspect of the present invention provides a sublingual composition for treating agitation or the signs of agitation in a subject in need thereof, wherein said agitation is associated with schizophrenia, bipolar disorder, bipolar mania, delirium, depression, or another related neuropsychiatric condition, and said sublingual composition comprises an effective amount of Dexmedetomidine or a pharmaceutically acceptable salt thereof, together with one or more pharmaceutically acceptable carriers and/or excipients.

An additional aspect of the present invention provides a sublingual composition for treating agitation or the signs of agitation in a subject in need thereof, wherein said agitation is associated with sundown syndrome in Alzheimer's disease/dementia, and said sublingual composition comprises an effective amount of Dexmedetomidine or a pharmaceutically acceptable salt thereof together with one or more pharmaceutically acceptable carriers and/or excipients.

Yet another aspect of the present invention provides a sublingual composition for treating agitation or the signs associated with agitation in a subject in need thereof, wherein said agitation is associated with an OPD/IPD procedure (e.g. MRI, CT or CAT scan, lumbar puncture, bone marrow aspiration/biopsy, tooth extraction or other dental procedures), and said sublingual composition comprises an effective amount of Dexmedetomidine or a pharmaceutically acceptable salt thereof together with one or more pharmaceutically acceptable carriers and/or excipients.

Yet another aspect of the present invention provides a sublingual composition for treating agitation or the signs associated with agitation in a subject in need thereof, wherein said agitation is associated with an alcohol and substance abuse withdrawal, and said sublingual composition comprises an effective amount of Dexmedetomidine or a pharmaceutically acceptable salt thereof together with one or more pharmaceutically acceptable carriers and/or excipients.

Another object of the present invention provides a sublingual composition comprising an effective amount of Dexmedetomidine or a pharmaceutically acceptable salt thereof together with one or more pharmaceutically acceptable carriers and/or excipients, wherein said sublingual composition is selected from the group consisting of a film, wafer, patch, lozenge, gel, spray, tablet, liquid drops or the like.

A further object of the present invention provides a method of sublingually administering an effective amount of Dexmedetomidine or a pharmaceutically acceptable salt thereof to a subject's oral mucosa to treat agitation or the signs of agitation at a dosage which does not cause significant sedation.

In a particular aspect of the invention, the dosage administered sublingually may conveniently be in the range of between about 3 micrograms to about 100 micrograms, Examples of suitable dosages include: about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms. The dose may be administered one or more times a day.

BRIEF DESCRIPTION OF THE DRAWINGS

FIG. 1A. Effect of sublingually administered Dexmedetomidine hydrochloride (Dex) at varying doses (0.5-3 µg/kg) on cumulative duration of aggressive and agitated behaviors. Data expressed as Mean±SEM. One-way ANOVA followed by Dunnett's post-hoc test. *$p<0.05$ $p<0.01$, *$p<0.001$ and ****$p<0.0001$ vs vehicle controls (vehicle).

FIG. 1B. Effect of sublingually administered Dexmedetomidine hydrochloride (Dex) at varying doses (0.5-3 µg/kg) on frequency of aggressive and agitated behaviors. Data expressed as Mean±SEM. One-way ANOVA followed by Dunnett's post-hoc test. *$p<0.05$ $p<0.01$, *$p<0.001$ and ****$p<0.0001$ vs vehicle controls (vehicle).

FIG. 1C. Effect of intravenously administered Dexmedetomidine hydrochloride (Dex) at varying doses (0.5-3 µg/kg) on cumulative duration of aggressive and agitated behaviors. Data expressed as Mean±SEM. One-way ANOVA followed by Dunnett's post-hoc test. $p<0.05$ $p<0.01$, *$p<0.001$ and **$p<0.0001$ vs vehicle controls (vehicle).

FIG. 1D. Effect of intravenously administered Dexmedetomidine hydrochloride (Dex) at varying doses (0.5-3 µg/kg) on frequency of aggressive and agitated behaviors.

Data expressed as Mean±SEM. One-way ANOVA followed by Dunnett's post-hoc test. *p<0.05 p<0.01, *p<0.001 and ****p<0.0001 vs vehicle controls (vehicle).

FIG. 2A. Effect of sublingually administered Dexmedetomidine hydrochloride (Dex) at varying doses (0.5-3 μg/kg) on Latency to attack. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 2B. Effect of intravenously administered Dexmedetomidine hydrochloride (Dex) at varying doses (0.5-3 μg/kg) on Latency to attack. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3A. Effect of sublingually administered Dexmedetomidine hydrochloride (Dex) at varying doses (0.5-3 μg/kg) on Cumulative duration of Neutral behaviors such as grooming, and exploration. Data expressed as Mean±SEM. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3B. Effect of sublingually administered Dexmedetomidine hydrochloride (Dex) at varying doses (0.5-3 μg/kg) on Frequency of Neutral behaviors such as grooming, and exploration. Data expressed as Mean±SEM. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3C. Effect of sublingually administered Dexmedetomidine hydrochloride (Dex) at varying doses (0.5-3 μg/kg) on Neutral behaviors such as immobile/quiet time. Data expressed as Mean±SEM. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3D. Effect of intravenously administered Dexmedetomidine hydrochloride (Dex) at varying doses (0.5-3 μg/kg) on Cumulative duration of Neutral behaviors such as grooming, and exploration. Data expressed as Mean t SEM. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3E. Effect of intravenously administered Dexmedetomidine hydrochloride (Dex) at varying doses (0.5-3 μg/kg) on Frequency of Neutral behaviors such as grooming, and exploration. Data expressed as Mean±SEM. Data is expressed as Mean t SEM. Statistical analysis was performed by One-way ANOVA followed by Dunnett's post-hoc test. *p<0.05 p<0.01, *p<0.001 and ****p<0.0001 vs vehicle controls (vehicle).

FIG. 3F. Effect of intravenously administered Dexmedetomidine hydrochloride (Dex) at varying doses (0.5-3 μg/kg) on Neutral behaviors such as immobile/quiet time. Data expressed as Mean±SEM. Data is expressed as Mean±SEM. Statistical analysis was performed by One-way ANOVA followed by Dunnett's post-hoc test. *p<0.05 p<0.01, *p<0.001 and ****p<0.0001 vs vehicle controls (vehicle).

FIG. 4A: Mean plasma concentrations following Sublingual (SL) Dexmedetomidine hydrochloride administration in rats. Data expressed as Mean±SD FIG. 4B: Mean plasma concentrations following Intravenous (IV) Dexmedetomidine hydrochloride administration in rats. Data expressed as Mean±SD

DETAILED DESCRIPTION OF THE INVENTION

I. Abbreviations

The following abbreviations are used throughout this specification:
AD: Alzheimer's disease
AUC: Area under the curve
BZDs: Benzodiazepines
CNS: Central nervous system
CT/CAT scan: computed tomography scan
Cmax: Maximum (or peak) serum concentration that a drug achieves in a specified compartment
EPS: Extrapyramidal side effects
FD & C: Federal Food, Drug, and Cosmetic
FTD: Fronto-temporal dementia
GABA: Gamma-aminoautyric Acid
5-HT: 5-Hydroxytryptamine
ICU: Intensive care unit
IPD: In-Patient department
MRI: Magnetic resonance imaging
Mg: Milligram
NE: Nor-epinephrine
OPD: Out-patient department
PTSD: Post-traumatic stress disorders
RSS: Ramsay sedation score
RIT: Rat intruder test
SLOS: Smith-Lemli Opitz syndrome
$T_{max}$: Time at which the C is observed.

II. Definitions

It will be understood that the terminology used herein is for the purpose of describing embodiments only, and is not intended to be limiting. As used in this specification, the singular forms "a", "an" and "the" include plural referents unless the context clearly dictates otherwise. Thus, for example, reference to "a solvent" includes one or more such solvents and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

The terms "treating," and "treatment," as used herein refer to curative therapy, prophylactic therapy, and/or preventative therapy and can be used interchangeably.

As used herein, unless indicated otherwise, the terms "pharmaceutical composition", "composition", "formulation" and "composition of the invention," are used interchangeably. Unless stated otherwise, the terms are meant to encompass, and are not limited to, pharmaceutical compositions containing drug substance i.e. Dexmedetomidine. The composition may also contain one or more "excipients" that are "inactive ingredients" or "compounds" devoid of pharmacological activity or other direct effect in the diagnosis, cure, mitigation, treatment, or prevention of disease or to affect the structure or any function of the human body.

As used herein, the term "an effective amount" is interchangeable with "therapeutically effective dose," or "therapeutically effective amount," and refers to an amount sufficient to produce the desired effect. An effective amount is sufficient to cause an improvement in a clinically significant condition of the subject.

As used herein, "pharmaceutically acceptable salt" refers to a salt known to be non-toxic and commonly used in the pharmaceutical literature. Typical inorganic acids used to form such salt include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyl alkandioic acids, aromatic acids, aliphatic and aromatic sulfonic acids may also be used. A preferred salt is the hydrochloride salt.

As used herein, the term "subject" preferably refers to a human patient. In some embodiments, the subject can be any animal, including non-human mammals, such as mice, rats, other rodents, rabbits, dogs, cats, swine, cattle, sheep, horses, or primates.

The term "agitation", as used herein, means irritability, emotional outburst, impaired thinking, or excess motor and verbal activity that may occur due to either dysfunction of specific brain regions such as frontal lobes or due to dysfunction of neurotransmitter systems such as dopamine and nor-epinephrine. In the present invention, agitation also includes aggression and hyper-arousal in post-traumatic stress disorder. The agitation may be acute or chronic.

The term "the signs of agitation" includes excessive motor activity (examples include: pacing, rocking, gesturing, pointing fingers, restlessness, performing repetitious mannerisms), verbal aggression (e.g. yelling, speaking in an excessively loud voice, using profanity, screaming, shouting, threatening other people), physical aggression (e.g. grabbing, shoving, pushing, clenching hands into fists, resisting, hitting others, kicking objects or people, scratching, biting, throwing objects, hitting self, slamming doors, tearing things, and destroying property).

The term "acute agitation" means agitation that occurs rapidly and is severe and sudden in onset. Acute agitation may be associated with, for example, neurodegenerative disease and neuropsychiatric conditions, although it may particularly exist in neuropsychiatric conditions. Acute agitation may lead to chronic agitation if it remains untreated.

The term "chronic agitation" means agitation developed over a long period of time, and is less severe than acute agitation. Chronic agitation may be associated with, for example, neurodegenerative disease and neuropsychiatric conditions, although it may particularly exist in neurodegenerative diseases.

The term "neurodegenerative disease" includes, but is not limited to, Alzheimer disease, frontotemporal dementia (or Pick's disease), Dementia, Dementia with Lewy bodies, post-traumatic stress disorder, Parkinson's disease, vascular dementia, vascular cognitive impairment, Huntington's disease, multiple sclerosis, Creutzfeldt-Jakob disease, multiple system atrophy, progressive supranuclear palsy or other related neurodegenerative diseases.

The term "neuropsychiatric conditions" includes, but is not limited to, schizophrenia, bipolar illness (bipolar disorder, bipolar mania), depression, delirium or other related neuropsychiatric conditions.

"Sundown syndrome" is a late-day circadian syndrome of increased confusion and restlessness, generally in a patient with some form of dementia. It seems to occur more frequently during the middle stages of Alzheimer dementia. It seems to subside with the progression of a patient's dementia. About 20-45% of Alzheimer type patients will experience some sort of sundowning confusion. Confusion and agitation worsen in the late afternoon and evening, or as the sun goes down.

The term "perioperative agitation" means agitation before, during or after any surgical procedure or ICU agitation unassociated with a neurodegenerative disease or neuropsychiatric condition.

The term "sublingual" literally means "under the tongue" and refers to a method of administering substances via the mouth in such a way that the substances are rapidly absorbed via the blood vessels under the tongue rather than via the digestive tract. Sublingual absorption occurs through the highly vascularized sublingual mucosa, which allows a substance direct access to the blood circulation, thereby providing for direct systemic administration independent of gastrointestinal influences and avoiding undesirable first-pass hepatic metabolism. Accordingly, the total amount of Dexmedetomidine or a pharmaceutically acceptable salt thereof in the formulation may be reduced, thereby reducing the likelihood of deleterious side effects and providing a cost benefit to the manufacturer.

"Sedation" as used herein means depressed consciousness in which a patient or subject retains the ability to independently and continuously maintain an open airway and a regular breathing pattern, and to respond appropriately and rationally to physical stimulation and verbal commands. As used herein "without causing significant sedation" means that the patient experiences a level of sedation not greater than Level 3 on the Ramsay Sedation Scale. Level 3 means sedated but responds to commands.

III. Methods

The present invention provides a method of treating agitation or the signs of agitation in a subject comprising administering an effective amount of an alpha-2 adrenergic agonist or a pharmaceutically acceptable salt thereof sublingually to the subject. In a particular aspect, the agitation is suppressed without also causing significant sedation.

In one embodiment, the alpha-2 adrenergic agonist includes, but is not limited to, Clonidine, Guanfacine, Guanabenz, Guanoxabenz, Guanethidine, Xylazine, Tizanidine, Medetomidine, Dexmedetomidine, Methyldopa, Methylnor-epinephrine, Fadolmidine, Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione or a pharmaceutically acceptable salt thereof.

In one preferred embodiment, the present invention provides a method of treating agitation or the signs of agitation in a subject comprising administering an effective amount of Dexmedetomidine or a pharmaceutically acceptable salt thereof sublingually to the subject. In a particular aspect, the agitation is suppressed without also causing significant sedation.

Agitation may be effectively treated using a relatively low dose of Dexmedetomidine or a pharmaceutically acceptable salt thereof via the sublingual route. Consequently, in addition to providing relief from agitation without causing significant sedation, the treatment is also effective with reduced or no side effects (for example, cardiac or respiratory side effects).

In a further embodiment, the present invention is directed to a method of treating agitation or the signs of agitation in a subject comprising administering Dexmedetomidine or a pharmaceutically acceptable salt thereof sublingually to the subject to provide fast-acting relief without a substantial portion of Dexmedetomidine or its pharmaceutically acceptable salt thereof passing into the liver of the patient.

In another embodiment, the present invention provides a method of treating agitation or the signs of agitation in a subject in need thereof, comprising administering an effective amount of Dexmedetomidine or a pharmaceutically acceptable salt thereof via a sublingual composition to the subject, wherein the sublingual composition is selected from a film, wafer, patch, lozenge, gel, spray, tablet, and liquid drops.

In a further embodiment, the present invention provides a method of treating agitation or the signs of agitation in a subject in need thereof, comprising administering to the subject an effective amount of an alpha-2 adrenergic agonist together with one or more pharmaceutically acceptable carriers and/or excipients via a sublingual composition, wherein the sublingual composition is a sublingual film. In a particular aspect, the agitation is associated with a neurodegenerative disease or neuropsychiatric condition. In another particular aspect, the treatment is effective without causing significant sedation.

In a further embodiment, the present invention provides a method of treating agitation or the signs of agitation in a subject in need thereof, comprising administering to the subject an effective amount of Dexmedetomidine or a pharmaceutically acceptable salt thereof together with one or more pharmaceutically acceptable carriers and/or excipients via a sublingual composition, wherein the sublingual composition is a sublingual film. In a particular aspect, the agitation is associated with a neurodegenerative disease or neuropsychiatric condition. In another particular aspect, the treatment is effective without causing significant sedation.

In yet other embodiment, the present invention provides a method of treating agitation or signs of agitation in a subject in need thereof, comprising administering to said subject an effective amount of an alpha-2 adrenergic agonist or a pharmaceutically acceptable salt thereof at a dosage that does not cause a significant sedation. Suitable alpha-2 adrenergic agonists include, but are not limited to, Clonidine, Guanfacine, Guanabenz, Guanoxabenz, Guanethidine, Xylazine, Tizanidine, Medetomidine, Dexmedetomidine, Methyldopa, Methylnorepinephrine, Fadolmidine, Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione or a pharmaceutically acceptable salt thereof. In a particular aspect of the invention, the dosage of alpha-2 adrenergic agonist used in the composition is from about 3 micrograms to about 100 micrograms.

In another embodiment, the present invention provides a method of treating agitation or the signs of agitation in a subject in need thereof, comprising administering to said subject an effective amount of Dexmedetomidine or a pharmaceutically acceptable salt thereof sublingually at a dosage that does not cause significant sedation. In a particular aspect of the invention, the dosage of Dexmedetomidine or a pharmaceutically acceptable salt thereof used in the sublingual composition is from about 3 micrograms to about 100 micrograms. Examples of suitable dosages include: about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms. The dose may be administered one or more times a day.

In a further embodiment, the present invention provides a method of treating agitation or the signs of agitation in a subject in need thereof, comprising administering to said subject an effective amount of Dexmedetomidine or a pharmaceutically acceptable salt thereof sublingually at a dosage of from about 0.05 micrograms/kg weight of subject to about 1.5 micrograms/kg weight of subject. Examples of suitable dosages include: about 0.1 micrograms/kg to about 1 micrograms/kg, about 0.1 micrograms/kg to about 0.5 micrograms/kg, about 0.1 micrograms/kg to about 0.4 micrograms/kg, about 0.1 micrograms/kg to about 0.3 micrograms/kg, about 0.1 micrograms/kg to about 0.2 micrograms/kg, about 0.07 micrograms/kg, about 0.05 micrograms/kg, about 0.1 micrograms/kg, about 0.2 micrograms/kg, about 0.3 micrograms/kg, about 0.4 micrograms/kg, about 0.5 micrograms/kg, about 0.6 micrograms/kg, about 0.7 micrograms/kg, about 0.8 micrograms/kg, about 0.9 micrograms/kg, about 1.0 micrograms/kg, about 1.1 micrograms/kg, about 1.2 micrograms/kg, about 1.3 micrograms/kg, about 1.4 micrograms/kg, about 1.5 micrograms/kg. The dose may be administered one or more times a day.

In yet other embodiment, the present invention provides a method of treating agitation or signs of agitation associated with neurodegenerative disease in a subject in need thereof, comprising administering to said subject an effective amount of an alpha-2 adrenergic agonist or a pharmaceutically acceptable salt thereof at a dosage that does not cause a significant sedation. Suitable alpha-2 adrenergic agonists include, but are not limited to, Clonidine, Guanfacine, Guanabenz, Guanoxabenz, Guanethidine, Xylazine, Tizanidine, Medetomidine, Dexmedetomidine, Methyldopa, Methylnorepinephrine, Fadolmidine Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione or a pharmaceutically acceptable salt thereof. The dosage of alpha-2 adrenergic agonist used in the composition is conveniently from about 3 micrograms to about 100 micrograms.

In a yet further embodiment, the present invention provides a method of treating agitation or the signs of agitation associated with neurodegenerative disease in a subject in need thereof, comprising sublingually administering to said subject an effective amount of Dexmedetomidine or a pharmaceutically acceptable salt thereof at a dosage that does not cause unwanted (e.g., significant) sedation. The dosage of Dexmedetomidine or a pharmaceutically acceptable salt thereof used may conveniently be from about 3 micrograms to about 100 micrograms, e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms, about 5 micrograms, about 6 micrograms, about 7 micrograms, about 8 micrograms, about 9 micrograms, about 10 micrograms, about 12 micrograms, about 14 micrograms, about 16 micrograms, about 18 micrograms. The dose may be administered one or more times a day.

In yet other embodiment, the present invention provides a method of treating agitation or signs of agitation associated with neuropsychiatric condition in a subject in need thereof, comprising administering to said subject an effective amount of an alpha-2 adrenergic agonist or a pharmaceutically acceptable salt thereof at a dosage that does not cause a significant sedation. Suitable alpha-2 adrenergic agonists include, but are not limited to, Clonidine, Guanfacine, Guanabenz, Guanoxabenz, Guanethidine, Xylazine, Tizanidine, Medetomidine, Dexmedetomidine, Methyldopa, Methylnorepinephrine, Fadolmidine, Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione or a pharmaceutically acceptable salt thereof. The dosage of alpha-2 adrenergic agonist used in the composition is conveniently from about 3 micrograms to about 100 micrograms.

In another embodiment, the present invention provides a method of treating agitation or the signs of agitation associated with neuropsychiatric condition in a subject in need thereof, comprising administering to said subject an effective amount of Dexmedetomidine or a pharmaceutically acceptable salt thereof sublingually at a dosage that does not cause significant sedation. The dosage of Dexmedetomidine or a pharmaceutically acceptable salt thereof used in a sublingual composition may conveniently be from about 3 micrograms to about 100 micrograms, e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms, about 5 micrograms, about 6 micrograms, about 7 micrograms, about 8 micrograms, about 9 micrograms, about 10 micrograms, about 12 micrograms, about 14 micrograms, about 15 micrograms, about 16 micrograms, about 18 micrograms, about 20 micrograms, about 30 micrograms, about 50 micrograms. The dose may be administered one or more times a day.

The level of acceptable sedation when treating a subject according to a method of the present invention is preferably at or below Level 3 according to the Ramsay sedation scoring (RSS) system. Thus, a particular embodiment of the present invention provides a method of treating agitation or the signs of agitation in a human subject in need thereof, comprising administering Dexmedetomidine or a pharmaceutically acceptable salt thereof sublingually to said subject at a dose in the range of about 3 micrograms to about 100 micrograms, thereby achieving an RSS at or below Level 3 (e.g. Level 2 or Level 3).

IV. Pharmaceutical Compositions

The present invention also provides sublingual pharmaceutical compositions comprising an effective amount of an alpha-2 adrenergic agonist or a pharmaceutically acceptable salt thereof, preferably Dexmedetomidine or a pharmaceutically acceptable salt thereof.

The sublingual pharmaceutical compositions of the present invention may also comprise a pharmaceutically acceptable carrier and/or excipient. Suitable pharmaceutically acceptable carriers include water, sodium chloride, binders, penetration enhancers, diluents, lubricants, flavouring agents, coloring agents and so on.

The sublingual pharmaceutical compositions of the present invention may be administered to a subject alone or in combination with one or more other suitable active ingredients.

In one embodiment, the present invention provides a sublingual pharmaceutical composition comprising an effective amount of Dexmedetomidine or a pharmaceutically acceptable salt thereof for the treatment of agitation in a subject, e.g., agitation associated with neurodegenerative disease, sundown syndrome in Alzheimer's disease or dementia. In a particular aspect, the sublingual pharmaceutical composition effectively treats agitation in a subject without causing significant sedation.

In another embodiment, the present invention provides a sublingual pharmaceutical composition comprising an effective amount of Dexmedetomidine or a pharmaceutically acceptable salt thereof for the treatment of agitation in a subject associated with schizophrenia, bipolar disorder, bipolar mania, other bipolar illness, depression, delirium or another related neuropsychiatric condition. In a particular aspect, the sublingual pharmaceutical composition effectively treats agitation in a subject without causing significant sedation.

The sublingual pharmaceutical composition of the present invention may be, for example, a film, wafer, patch, lozenge, gel, spray, tablet, liquid drops or the like.

In one embodiment of the invention, the sublingual pharmaceutical composition is in the form of a tablet or packed powder.

In another embodiment of the invention, the sublingual pharmaceutical composition is in the form of a patch or film (e.g. thin film). The patch may have adhesive qualities to prevent movement or swallowing of the patch. The patch may be ingestible in case of accidental swallowing or to allow for its easy disposal, or the patch may be removed from under the tongue after a prescribed time.

In yet another embodiment of the invention, the sublingual pharmaceutical composition is in the form of a paste, gel or ointment. The viscosity of the paste, gel or ointment can be adjusted to allow for retention under the tongue.

In a further embodiment of the invention, the sublingual pharmaceutical composition is in a liquid (e.g. as a solution, suspension or emulsion), and may be, for example, presented as a spray or as drops. Solutions include the active ingredient together with a diluent such as water, normal saline, sodium chloride solution, or any other suitable solvent such as propylene glycol, glycerol, ethyl alcohol and so on. The diluent for the solution may particularly be physiological saline solution or water. The amount of solution administered may conveniently be about 0.01 ml to about 1 ml (e.g., about 0.025-0.5 ml).

The non-solid compositions of the invention may conveniently be administered by spraying, dripping, painting or squirting the composition under the tongue.

In a particular embodiment of the invention, Dexmedetomidine or a pharmaceutically acceptable salt thereof is sublingually administered in liquid form, e.g. in a flavored or unflavored physiological saline solution. The liquid composition may conveniently be administered under the tongue as drops or as a spray.

Dexmedetomidine, or a pharmaceutically acceptable salt thereof may conveniently represent from about 0.001% to about 99.99% of the overall composition, e.g. about 0.01% to about 90%, more particularly about 0.01% to about 30/%.

When the composition is a liquid or gel, a first unit dose is applied and held in place under the tongue for a predetermined time, for example for at least about 30 seconds, or more particularly about 60 seconds or more. A second unit dose may then be applied and held in place for a similar amount of time. Surprisingly, this procedure noticeably increases the effect of the composition of the invention in the treatment of agitation or the signs of agitation.

In another embodiment, the sublingual composition of Dexmedetomidine or a pharmaceutically acceptable salt thereof is a hard tablet or a compressed powder tablet. The tablet may conveniently be designed to dissolve under the tongue in about 30 to 120 seconds as disclosed in U.S. Pat. No. 6,221,392 to Khankari, et al., incorporated herein by reference. In a particular embodiment, the sublingual composition of Dexmedetomidine or a pharmaceutically acceptable salt thereof is a hard tablet having a low grit component for an organoleptically pleasant mouth feel. The tablet (or particles thereof containing the active ingredient which can be compressed to form the tablet) may also comprise a protective outer coating, e.g. any polymer conventionally used in the formation of microparticles, matrix-type microparticles and microcapsules.

In a further embodiment, the sublingual composition of Dexmedetomidine or a pharmaceutically acceptable salt thereof is a hard, compressed, rapidly dissolvable tablet. The tablet conveniently includes the active ingredient within a matrix. The matrix may be composed of, for example, at least one filler and a lubricant. Fillers include, for example, lactose or mannitol, and suitable lubricants include magnesium stearate, silicon dioxide and talc. The matrix may also include one or more of: a binder (e.g. povidone, a sugar or carboxymethylcellulose), a disintegrant (e.g. croscarmellose sodium, crospovidone or sodium starch glycolate), a sweeting agent (e.g. sucralose) and the like. The tablet may conveniently have a friability of about 2% or less and a hardness of about 15 to about 50 Newtons.

Another aspect of the present invention provides a method of making a packaged, sublingual tablet. The method includes the steps of: (a) forming a mixture comprising Dexmedetomidine or a pharmaceutically acceptable salt thereof and a matrix including at least a non-direct compression filler and a lubricant; (b) compressing the mixture to form a plurality of hard, compressed, rapidly disintegrable particles (e.g. beads) including the active ingredient distributed in the sublingually dissolvable matrix; and (c) storing the product in bulk prior to packaging. In another embodiment, the dosage forms are then packaged in a lumen of a package such that there are more than one per package. Direct compression is the preferred method of forming the dosage forms. There is also provided hereby an openable and reclosable package containing a plurality of hard, compressed, rapidly dissolving tablets adapted for direct oral dosing as described above.

In another embodiment, the present invention is a sublingual tablet comprising an effervescent agent. The effervescent agent may conveniently be present in an amount up to about 95% by weight, based on the weight of the finished tablet, and more particularly in an amount of between about 30% and about 80% by weight. Sufficient effervescent material is included in the tablet composition to generate more than about 5 $cm^3$ but less that about 30 $cm^3$ of gas upon exposure of the tablet to an aqueous environment. Sublingual compositions comprising effervescent agents are disclosed in U.S. Pat. No. 6,200,604, which is incorporated herein by reference.

In one particular embodiment, an effervescent agent releases carbon dioxide e.g., as a result of the reaction of a soluble acid source with an alkaline carbonate or bicarbonate. The acid source may conveniently include food acids and acids such as citric acid, tartaric, amalic, fumeric, adipic and succinic acid. Carbonate and bicarbonate sources include dry solid carbonate and bicarbonate salts such as sodium bicarbonate, sodium carbonate, potassium bicarbonate, potassium carbonate, magnesium carbonate and the like.

Spray compositions of the present invention for sublingual administration may include one or more pharmaceutically acceptable liquids (e.g., present in the amount of about 30% to about 99.99% by weight of the composition). Such liquids may be solvents, co-solvents, or non-solvents for Dexmedetomidine or a pharmaceutically acceptable salt thereof. Examples of pharmaceutically acceptable liquids include water, ethanol, dimethyl sulfoxide, propylene glycol, polyethylene glycol, propylene carbonate, pharmaceutically acceptable oils (e.g., soybean, sunflower, peanut, peppermint etc.) and the like. The pharmaceutically acceptable liquid is selected either to dissolve the active pharmaceutical ingredient, to produce a stable, homogenous suspension or solution of it, or to form any combination of a suspension or solution.

Furthermore, sublingual, spray formulations of Dexmedetomidine or a pharmaceutically acceptable salt thereof may include one or more carriers and/or excipients. Examples of carriers/excipients include viscosity-modulating materials (e.g. polymers, sugars, sugar alcohols, gums, clays, silicas, and the like). One particular polymer that may conveniently be used is polyvinylpyrrolidone (PVP). The viscosity-modulating material may conveniently be present in the amount of from about 0.01% to about 65% by weight of the spray formulation. Other examples of carriers/excipients include preservatives (e.g. ethanol, benzyl alcohol, propylparaben and methylparaben). Preservatives may conveniently be present in the amount of from about 0.001% to about 10% by weight of the spray formulation. Carriers/excipients may also be flavoring agents, sweeteners (e.g. sugars such as sucrose, glucose, dextrose, maltose, fructose, etc.), artificial sweeteners (e.g. saccharin, aspartame, acesulfame, sucralose etc.), or sugar alcohols (e.g. mannitol, xylitol, lactitol, maltitol syrup etc.) present conveniently in an amount of from about 0.001% to about 65% by weight of the spray formulation. Other examples of carriers/excipients include buffers and pH-adjusting agent (e.g., sodium hydroxide, citrate, and citric acid) conveniently present in an amount of from about 0.01% to about 5% by weight of the spray formulation. Coloring agents (e.g. present in an amount of from about 0.001% to about 5% by weight of the spray formulation), fragrances (e.g. present in an amount of from about 0.001% to about 1% by weight of the spray formulation), chelating agents such as EDTA (e.g. present in an amount of from about 0.001% to about 1% by weight of the spray formulation), UV absorbers (e.g. present in an amount of from about 0.001% to about 10% by weight of the spray formulation), and anti-foam agents (e.g. low molecular weight alcohols, dimethicone) conveniently present in an amount of from about 0.001% to about 5% by weight of the spray formulation may also be included as appropriate carriers/excipients in the spray formulations of the present invention.

One particular aspect of the present invention provides a sublingual film comprising Dexmedetomidine or a pharmaceutically acceptable salt thereof, together with one or more carriers and/or excipients, for the treatment of agitation.

Excipients which may be incorporated into the sublingual films of the present invention include one or more of the following: film forming agents, mouth feel improvers, plasticizers, stabilizers, surfactants, preservatives, sweetening agents, colorants, flavourants, emulsifiers, disintegrants, salivating agents, antioxidants, permeation enhancers, solvents and the like.

Film forming agents generally mean agents that provide structure to the film of the present invention. The effective amount of the film forming agent ranges from about 10% to about 99%, more preferably about 50% to about 90% by weight of the composition. Film forming agents that can be utilized as part of the film composition of the present invention include, but are not limited to, cellulose ethers, modified starches, natural gums, edible polymers, seaweed extracts, land plant extracts, pullulan, polyvinylpyrrolidone, derivatives thereof and combinations thereof.

Examples of cellulose ethers include, but are not limited to, methylhydroxycellulose, methylcellulose, ethylcellulose, hydroxyethylcellulose, carboxymethylcellulose, derivatives thereof and combinations thereof.

Modified starches include, but are not limited to, acid and enzyme hydrolyzed corn and potato starches, derivatives thereof and combinations thereof.

Examples of natural gums include, but are not limited to, gum arabic, guar gum, locust bean gum, carrageenan gum, acacia, karaya, ghatti, tragacanth agar, tamarind gum, xanthan gum, derivatives thereof and combinations thereof.

Examples of edible polymers include, but are not limited to, microcrystalline cellulose, cellulose ethers, xanthan, derivatives thereof and combinations thereof.

Seaweed extract examples include, but are not limited to, sodium alginate, carrageenans, derivatives thereof and. combinations thereof.

Land plant extracts include, but are not limited to, konjac, pectin, arabinoglactan, derivatives thereof and combinations thereof.

Particular film forming agents include pullulan, sodium alginate, polyvinylpyrrolidone, methylcellulose and methylhydroxycellulose (MHC).

The term "solvent" generally refers to liquids that will dissolve solutes. A solvent may be used to dissolve film-forming agents and other excipients to prepare film-forming compositions of the present invention. Solvents include, but are not limited to, demineralized/distilled water, ethyl alcohol, isopropyl alcohol, methyl ethyl ketone, propylene glycol methyl ether acetate, dimethyl acetamide, ethylene glycol mono-propyl ether, and toluene. A sublingual film of the present invention may conveniently comprise a solvent in an amount up to about 1% w/w.

The term "stabilizer" generally refers to an agent that will impart stability to the formulation during its shelf life. Stabilizers of the present invention can include, for example, oil/water emulsifiers and flavor fixatives. The effective amount of a stabilizer agent in a composition of the invention may be, for example, in the range of about 0% to about 45%, more particularly about 4% to about 25%, by weight of the composition. Examples of suitable stabilizing agents of the present invention include, but are not limited to, gum arabic, microcrystalline cellulose, carrageenan, xanthan gum, locust bean gum, derivatives thereof and combinations thereof. Particular stabilizing agents of the present invention include gum arabic and microcrystalline cellulose.

"Disintegrants" can aid the dissolution of edible films allowing for the efficacy of the film to be realized sooner. Suitable disintegrants for use in an edible film of the present invention include, but are not limited to, alginic acid, microcrystalline cellulose and carboxymethylcellulose. Special disintegrants known as super-disintegrants are also suitable for use in an edible film of the present invention. Super-disintegrants include cross-linked polymers (e.g. crospovidone), cross-linked starches (e.g. sodium starch glycolate), and cross-linked celluloses (e.g. a modified carboxymethylcellulose such as croscarmellose). These super-disintegrants are insoluble in water and most other solvents, have rapid swelling properties, and have good water uptake with high capillary action, resulting in fast disintegration. Their insolubility in many solvents also means they enable the manufacture of sublingual compositions of this invention in a single step process as opposed to costly multi-step processes.

The disintegrants or super-disintegrants are conveniently present in a sublingual composition of this invention (e.g. an edible film) in an amount ranging from about 1% to about 10%, more particularly about 1% to about 5% by weight of the composition.

"Emulsifiers" suitable for use in an edible film of the present invention include, but are not limited to, gum arabic, carrageenan, triethanolamine stearate, quaternary ammonium compounds, acacia, gelatin, lecithin, bentonite, veegum, derivatives thereof and combinations thereof. Emulsifiers can be used in a composition of the present invention in an amount up to about 40%, more particularly up to about 25%, by weight of the composition. The emulsifier can be a stabilizer creating an oil/water emulsion encapsulating volatile oils and flavoring agents, thereby essentially acting as a flavor fixative. A particular emulsifier for use in an edible film of the present invention is gum arabic.

A "plasticizing agent" or "plasticizer" may be utilized to improve flexibility and reduce brittleness of an edible film composition of the present invention. The plasticizing agent may conveniently constitute up to about 30%, e.g. up to about 15% by weight of the composition. Examples of suitable plasticizing agents include, but are not limited to, glycerin, sorbitol, triacetin, monoacetin, diacetin, polyethylene glycol, propylene glycol, hydrogenated starch hydrolysates, corn syrups, low molecular weight propylene glycols, phthalate derivatives like dimethyl, diethyl and dibutyl phthalate, citrate derivatives such as tributyl, triethyl, acetyl citrate and castor oil derivatives thereof and combinations thereof. Particular plasticizing agents of the present invention include sorbitol and glycerin.

The term "preservative" generally refers to an excipient used to kill microorganisms or prevents, inhibits or retards their growth and reproduction, and is included in a product in a concentration only sufficient to prevent spoilage or the growth of inadvertently added microorganisms. Suitable preservative includes, but are not limited to, methylparaben, propylparaben and sodium benzoate. The preservative may conveniently be present in the composition from about 0.001% to about 10% w/w of the composition.

The term "sweetening agent" generally refers to an excipient used to impart sweetness to a pharmaceutical composition. Suitable sweetening agents for use in a composition of the present invention include, but are not limited to, aspartame, dextrose, glycerin, mannitol, saccharin sodium, sorbitol and sucrose. The sweetening agent may conveniently be present in the composition in an amount of from about 5% to about 20% w/w of the composition.

The term "coloring agent" or "colorant" generally refers to an excipient used to impart color to a pharmaceutical composition. Suitable colorants include, but are not limited to, FD&C Red No. 3, FD&C Red No. 20, FD&C Yellow No. 6, FD&C Blue No. 2, D&C Green No. 5, D&C Orange No. 5, D&C Red No. 8, other F. D. & C. dyes, caramel, red ferric oxide, and natural coloring agents such as grape skin extract, beet red powder, beta-carotene, annatto, carmine, turmeric or paprika. The colorant may conveniently be present in the composition in an amount of from about 0.001% to about 10% w/w of the composition.

The term "flavoring agent" or "flavorant" generally refers to an excipient used to impart a pleasant flavor (and often also odor) to a pharmaceutical composition. Suitable flavorants include, but are not limited to, synthetic flavoring oils, flavoring aromatics, natural oils, extracts from whole plants or parts thereof such as leaves, flowers, fruits or combinations thereof. Examples include cinnamon oil, wintergreen oil, peppermint oil, clove oil, bay oil, anise oil, eucalyptus oil, thyme oil, cedar leave oil, nutmeg oil, sage oil, bitter almond oil and cassia oil. Other useful flavorants include vanilla, citrus fruit oils such as lemon, orange, grape, lime or grapefruit oil, and fruit essences such as apple, pear, peach, strawberry, raspberry, cherry, plum, pineapple or apricot essence. Flavorants of particular interest for use in a composition of the present invention include commercially available orange, grape, cherry and bubble gum flavors and mixtures thereof. The amount of flavoring used will depend on a number of factors, including the organoleptic effect desired. Particular flavorants include grape and cherry flavors, and citrus fruit flavors such as orange flavor. The flavorant may conveniently be present in the composition in an amount of from about 0.001% to about 10% w/w of the composition.

The term "salivating agent" is an agent that promotes greater salivation during use of a composition of the present invention. This may be an important feature if the composition is intended to be taken by the patient without the aid of water to help in the transporting of the composition to the stomach of the patient. The salivating agent can be, for example, an emulsifier or a food acid that initiates salivation in the mouth of the patient. Examples of emulsifiers useful as salivating agents include alkyl aryl sulfonates, alkyl sulfates, sulfonated amides and amines, sulfated and sulfonated esters and ethers, alkyl sulfonates, polyethoxylated esters, mono-, di-, and triglycerides, diacetyl tartaric esters of monoglycerides, polyglycerol esters, sorbitan esters and ethoxylates, lactylated esters, phospholipids such as lecithin, polyoxyethylene sorbitan esters, proplyene glycol esters, sucrose esters, and mixtures thereof. The emulsifier may be either saturated or unsaturated. It should be noted that some of the emulsifiers that are salivating agents may also function as binders. Examples of food acids useful as salivating agents include citric acid, malic acid, tartarate, food salts such as sodium chloride and salt substitutes, potassium chloride, and mixtures thereof. The amount of salivating agent present in a sublingual film of the present invention may convenient be up to about 15% by weight of the final composition, e.g. in the range of from about 0.3% to 0.4% by weight of the composition.

The term "antioxidant" generally refers to an excipient used to inhibit oxidation and thus prevent deterioration of active agents by oxidative processes. Suitable antioxidants include, for example, ascorbic acid, ascorbyl palmitate, butylated hydroxyanisole, butylated hydroxytoluene, hypophosphorous acid, monothio-glycerol, propyl gallate, sodium ascorbate, citric acid, sodium bisulfite, sodium formaldehyde sulfoxylate, sodium metabisulfite, EDTA and sodium edetate. The anti-oxidant may conveniently be present in the composition in an amount of from about 0.001% to about 2% w/w of the composition.

The term "permeation enhancer" generally refers to an excipient used to enhance permeation of an active agent to cellular membranes or enhance the local/systemic absorption of the active agent. Permeation enhancers that may be used in the present invention include, but are not limited to, solubilizers such as alcohols, polyethylene glycols, chelating agents (e.g. cyclodextrins), sucrose laurate or sucrose oleate. The permeation enhancer may conveniently be present in the composition in an amount of from about 0.1% to about 5% w/w of the composition.

In one embodiment of the present invention, the sublingual pharmaceutical composition of the present invention includes a mucosal permeation enhancer appropriate for enhancing the mucosal absorption of the composition.

Sublingual Dexmedetomidine formulations (such as sprays, drops, and the like) may be made by mixing appropriate quantities of the foregoing ingredients in accordance with standard good manufacturing practices. The relative amounts of each ingredient should not interfere with the desirable pharmacological and pharmacokinetic properties of the resulting formulation.

Sublingual Dexmedetomidine films of the present invention may be conveniently prepared using PharmFilm® technology (owned by MonoSol) or technology owned by ARx LLC. Various patents and patent applications are incorporated herein in entirety and includes U.S. Pat. or Publication Nos. 9585961, 7470397, 7727466, 9248146, 9545376, 2017-0087084, 9662297, 9662301, 2017-0246108, 2017-0252294, 9441142 assigned to ARx LLC and 7425292, 7357891, 8663687, 8685437, 7897080, 8241661, 8617589, 8936825, 9561191, 9303918, 9346601, 8282954, 7972618, 9073294 assigned to Monosol Rx.

In preparing the sublingual film of the present invention the active agent, e.g. Dexmedetomidine or a pharmaceutically acceptable salt thereof, film forming agents and optionally one or more carriers and/or excipients selected from the group comprising of mouth feel improver, plasticizer, stabilizer, surfactant, preservative, sweetening agent, colorant, flavourant, emulsifier, disintegrant, salivating agent, antioxidant, permeation enhancer are dissolved in a compatible solvent to form a film forming composition. Compatible solvents include water, alcohols such as ethanol, ethyl acetate, acetone, and mixtures thereof. The film forming composition is cast on a releasable carrier and dried to form a sheet/film. The carrier material must have a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed. The sublingual film of the present invention can also be prepared by other established processes e.g. extrusion (for example, Hot melt extrusion, Solid dispersion extrusion), casting (for example, solid casting or semi-solid casting), Rolling methods and the like.

V. Administration

In an aspect, the present invention provides a sublingual composition comprising an alpha-2 adrenergic agonist or a pharmaceutically acceptable salt thereof, administered to a subject in an amount sufficient to effectively treat agitation. The amount of alpha-2 adrenergic agonist is sufficient to effectively treat agitation without causing significant sedation. The alpha-2 adrenergic agonist may conveniently be delivered on an "as needed basis" in one, two or more doses per day to the animal (e.g. human) subject. The composition may also be administered via a single dosage form or via multiple dosage forms.

In another aspect, the present invention provides a sublingual composition comprising Dexmedetomidine or a pharmaceutically acceptable salt thereof, administered to a subject in an amount sufficient to effectively treat agitation. In a particular aspect, the amount of Dexmedetomidine or a pharmaceutically acceptable salt thereof used is sufficient to effectively treat agitation without causing significant sedation. The Dexmedetomidine or a pharmaceutically acceptable salt thereof may conveniently be delivered on an "as needed basis" in one, two or more doses per day to the animal (e.g. human) subject. The composition may also be administered via a single dosage form or via multiple dosage forms.

Following administration of a composition of this invention to a subject, a therapeutic (i.e. anti-agitation) effect may begin within about 60 minutes (e.g. within about 30, 20, 15, 10, 5, 3, 2 or 1 minutes) after administration, or within about 30 seconds after administration. The signs of agitation may also be relieved within about 1 to about 60 minutes after administration, and more typically within about 5 to about 30 minutes. A second dose of the composition of this invention may be administered to the subject if the signs of agitation are not relieved within about 60 minutes.

Treatment protocols may include one or more dosage intervals (e.g. two or more dosage intervals, five or more dosage intervals, or ten or more dosage intervals). Depending on the physiology of the subject and the desired therapeutic effect, the duration of dosage intervals and treatment protocols according to embodiments of the present invention may vary.

Dexmedetomidine or a pharmaceutically acceptable salt thereof may be administered as a sublingual composition to treat agitation or the signs of agitation either alone or in combination with one or more further active agents. When used in combination, the active agents can either be formulated as a single composition or as two or more separate compositions, which can be administered simultaneously, sequentially or separated by an appropriate period of time.

Where Dexmedetomidine or a pharmaceutically acceptable salt thereof is administered with a second active agent to treat agitation or the signs of agitation, the weight ratio of respectively Dexmedetomidine or a pharmaceutically acceptable salt thereof to the second active agent may generally be in the range from about 1:2 to about 1:2.5; about 1:2.5 to about 1:3; about 1:3 to about 1:3.5 about 1:3.5 to about 1:4; about 1:4 to about 1:4.5, about 1:4.5 to about 1:5; about 1:5 to about 1:10; and about 1:10 to about 1:25. For example, the weight ratio may particularly be between about 1:1 to about 1:5; about 1:5 to about 1:10; about 1:10 to about 1:15; or about 1:15 to about 1:25. Alternatively, the weight ratio of respectively the second active agent to Dexmedetomidine or a pharmaceutically acceptable salt may be in the range of from about 2:1 to about 2.5:1; about 2.5:1 to about 3:1; about 3:1 to about 3.5:1; about 3.5:1 to about 4:1; about 4:1 to about 4.5:1; about 4.5:1 to about 5:1; about 5:1 to about 10:1; and about 10:1 to about 25:1. For example, the weight ratio of respectively the second active agent to Dexmedetomidine or a pharmaceutically acceptable salt thereof may particularly be in the range of from about 1:1 to about 5:1; about 5:1 to about 10:1; about 10:1 to about 15:1; or about 15:1 to about 25:1. It is to be understood that all ranges between the quoted ranges are also covered herein, and constitute further particular aspects of this invention.

VI. Dosing Regimen

The dosing regimen employed may depend on several factors, such as the type of agitation treated, the severity of the signs, and whether the agitation is due to an underlying medical condition.

Dexmedetomidine or a pharmaceutically acceptable salt thereof may be administered sublingually in any appropriate dose to an animal (e.g. human). In certain embodiments, the human dose may be from about 3 micrograms to about 100 micrograms (e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms). The dose may be administered one or more times a day.

Dexmedetomidine or a pharmaceutically acceptable salt thereof may be administered sublingually in any appropriate dose to a human. In some variations, the human dose may be from about 0.05 micrograms/kg weight of subject to about 1.5 micrograms/kg weight of subject. Examples of suitable dosages include: about 0.1 micrograms/kg to about 1 micrograms/kg, about 0.1 micrograms/kg to about 0.5 micrograms/kg, about 0.1 micrograms/kg to about 0.4 micrograms/kg, about 0.1 micrograms/kg to about 0.3 micrograms/kg, about 0.1 micrograms/kg to about 0.2 micrograms/kg, about 0.07 micrograms/kg, about 0.05 micrograms/kg, about 0.1 micrograms/kg, about 0.2 micrograms/kg, about 0.3 micrograms/kg, about 0.4 micrograms/kg, about 0.5 micrograms/kg, about 0.6 micrograms/kg, about 0.7 micrograms/kg, about 0.8 micrograms/kg, about 0.9 micrograms/kg, about 1.0 micrograms/kg, about 1.1 micrograms/kg, about 1.2 micrograms/kg, about 1.3 micrograms/kg, about 1.4 micrograms/kg, about 1.5 micrograms/kg. The dose may be administered one or more times a day.

VII. Specific Embodiments of the Invention

Embodiment 1. A method of treating agitation or the signs of agitation in a subject in need thereof comprising administering sublingually to said subject an effective amount of Dexmedetomidine or a pharmaceutically acceptable salt thereof.

Embodiment 2. A method of treating agitation or the signs of agitation in a subject in need thereof comprising administering to said subject an effective amount of Dexmedetomidine or a pharmaceutically acceptable salt thereof, wherein said Dexmedetomidine or a pharmaceutically acceptable salt thereof is sublingually administered at a dosage that treats agitation or the signs of agitation without causing significant sedation.

Embodiment 3. The method according to Embodiment 1 or 2, wherein said dosage of Dexmedetomidine or a pharmaceutically acceptable salt thereof is in range of from about 3 micrograms to about 100 micrograms (e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms).

Embodiment 4. The method according to Embodiments 1, 2 or 3, wherein said subject is mammal, preferably human.

Embodiment 5. The method according to any one of Embodiments 1 to 4, wherein said agitation is associated with a neurodegenerative disease.

Embodiment 6. The method according to Embodiment 5, wherein said neurodegenerative disease is selected from Alzheimer disease, fronto-temporal dementia (FTD), dementia, dementia with Lewy bodies (DLB), post-traumatic stress disorder, Parkinson's disease, vascular dementia, vascular cognitive impairment, Huntington's disease, multiple sclerosis, Creutzfeldt-Jakob disease, multiple system atrophy, and progressive supranuclear palsy.

Embodiment 7. The method according to any one of Embodiments 1 to 4, wherein the agitation is associated with a neuropsychiatric condition.

Embodiment 8. The method according to Embodiment 7, wherein said neuropsychiatric condition is selected from schizophrenia, bipolar illness (such as mania, disorder), delirium, and depression.

Embodiment 9. The method according to Embodiment 5, wherein the agitation is associated with sundown syndrome in dementia or Alzheimer's disease.

Embodiment 10. A sublingual composition for use in the treatment of agitation or the signs of agitation in a subject in need thereof, wherein said agitation is not perioperative agitation and said sublingual composition comprises an effective amount of Dexmedetomidine or a pharmaceutically acceptable salt thereof and one or more pharmaceutically acceptable carriers/excipients.

Embodiment 11. A sublingual composition for use in the treatment of agitation or the signs of agitation in a subject in need thereof, wherein said agitation is associated with a neurodegenerative disease and said sublingual composition comprises an effective amount of Dexmedetomidine or a pharmaceutically acceptable salt thereof and one or more pharmaceutically acceptable carriers/excipients.

Embodiment 12. A sublingual composition for use in the treatment of agitation or the signs of agitation in a subject in need thereof, wherein said agitation is associated with a neuropsychiatric condition and said sublingual composition comprises an effective amount of Dexmedetomidine or a pharmaceutically acceptable salt thereof and one or more pharmaceutically acceptable carriers/excipients.

Embodiment 13. A sublingual composition for use in the treatment of agitation or the signs of agitation in a subject in need thereof, wherein said agitation is associated with sundown syndrome in dementia or Alzheimer's disease and said sublingual composition comprises an effective amount of Dexmedetomidine or a pharmaceutically acceptable salt thereof and one or more pharmaceutically acceptable carriers/excipients.

Embodiment 14. The sublingual composition according to Embodiment 11, wherein said neurodegenerative disease is selected from the group consisting of Alzheimer disease, frontotemporal dementia (FTD), dementia, dementia with Lewy bodies (DLB), post-traumatic stress disorder, Parkinson's disease, vascular dementia, vascular cognitive impairment, Huntington's disease, multiple sclerosis Creutzfeldt-Jakob disease, multiple system atrophy, and progressive supranuclear palsy.

Embodiment 15. The sublingual composition according to Embodiment 14, wherein said neurodegenerative disease is selected from dementia, frontotemporal dementia, Alzheimer's disease and Parkinson's disease.

Embodiment 16. The sublingual composition according to Embodiment 12, wherein said neuropsychiatric condition is selected from the group consisting of schizophrenia, bipolar illness (such as mania, disorder), delirium and depression.

Embodiment 17. The sublingual composition according to any one of Embodiments 10 to 16, wherein said composition is selected from a film, wafer, patch, lozenge, gel, spray, tablet, liquid drops or the like.

Embodiment 18. The sublingual composition according to Embodiment 17, wherein the composition is a film.

Embodiment 19. The sublingual composition according to Embodiment 18, wherein the film is mucoadhesive in nature and provides a quick onset of action.

Embodiment 20. The sublingual composition according to any one of Embodiments 10 to 19, wherein Dexmedetomidine or a pharmaceutically acceptable salt thereof is administered at a dosage that treats agitation or the signs of agitation without causing significant sedation.

Embodiment 21. The sublingual composition according to Embodiment 20 wherein the observed level of sedation is not greater than 3 on the Ramsay sedation scale.

Embodiment 22. The sublingual composition according to any one of Embodiments 10 to 21, wherein Dexmedetomidine or a pharmaceutically acceptable salt thereof is administered to said subject (e.g. human) at a dosage in the range of from about 3 micrograms to about 100 micrograms (e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms).

Embodiment 23. A method of treating agitation or the signs of agitation in a subject in need thereof, the method comprises sublingually administering to said subject an effective amount of Dexmedetomidine or a pharmaceutically acceptable salt thereof, wherein the agitation is not perioperative agitation.

Embodiment 24. The method according to Embodiment 23, wherein the agitation is associated with a neurodegenerative disease and/or neuropsychiatric condition.

Embodiment 25. The method according to Embodiment 24, wherein the neurodegenerative disease is selected from the group consisting of Alzheimer disease, frontotemporal dementia (FTD), dementia, dementia with Lewy bodies (DLB), post-traumatic stress disorder, Parkinson's disease, vascular dementia, vascular cognitive impairment, Huntington's disease, multiple sclerosis, Creutzfeldt-Jakob disease, multiple system atrophy, progressive supranuclear palsy or other related neurodegenerative disorder.

Embodiment 26. The method according to Embodiment 24, wherein the neuropsychiatric condition is selected from the group consisting of schizophrenia, bipolar illness (e.g. bipolar disorder or bipolar mania), delirium and depression.

Embodiment 27. The method according to any one of Embodiments 23 to 26, wherein agitation or the signs of agitation are treated effectively without causing significant sedation.

Embodiment 28. The method according to any one of Embodiments 23 to 27, wherein Dexmedetomidine or a pharmaceutically acceptable salt thereof is administered in form of a film, wafer, patch, lozenge, gel, spray, tablet, liquid drops or the like.

Embodiment 29. A method of treating of agitation or the signs of agitation in a subject in need thereof, wherein said agitation is associated with an OPD/IPD procedure (e.g. MRI, CT or CAT scan, lumbar puncture, bone marrow aspiration/biopsy, tooth extraction or other dental procedures), and said method comprises administering to said subject sublingually an effective amount of Dexmedetomidine or a pharmaceutically acceptable salt thereof.

Embodiment 30. A method of treating of agitation or the signs of agitation in a subject in need thereof, wherein said agitation is associated with an alcohol and substance abuse withdrawal and said method comprises administering to said subject sublingually an effective amount of Dexmedetomidine or a pharmaceutically acceptable salt thereof.

Embodiment 31. The method according to Embodiment 29 or 30, wherein said Dexmedetomidine or a pharmaceutically acceptable salt thereof is sublingually administered at a dosage that treats said agitation or the signs of agitation without causing significant sedation.

Embodiment 32. The method according to Embodiment 31, wherein said dosage of Dexmedetomidine or a pharmaceutically acceptable salt thereof is in range of from about 3 micrograms to about 100 micrograms (e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms).

Embodiment 33. The composition or method according to any preceding Embodiment, wherein Dexmedetomidine or a pharmaceutically acceptable salt thereof is administered once, twice or thrice daily or on an "as needed" basis.

Embodiment 34. The composition or method according to any preceding Embodiment, wherein Dexmedetomidine or a pharmaceutically acceptable salt thereof is administered in a manner that produces a therapeutic effect in less than about 60 minutes, particularly within about 30 seconds to about 30 minutes.

Embodiment 35. A method of treating agitation or the signs of agitation in a subject in need thereof comprising administering sublingually to said subject an effective amount of an alpha-2 adrenergic agonist or a pharmaceutically acceptable salt thereof.

Embodiment 36. A method of treating agitation or the signs of agitation in a subject in need thereof comprising administering to said subject an effective amount of an alpha-2 adrenergic agonist or a pharmaceutically acceptable salt thereof, wherein said alpha-2 adrenergic agonist is sublingually administered at a dosage that treats agitation or the signs of agitation without causing significant sedation.

Embodiment 37. The method according to Embodiment 35 or 36, wherein said dosage of alpha-2 adrenergic agonist is in range of from about 3 micrograms to about 100 micrograms (e.g. about 5 micrograms to about 100 micrograms, about 5 micrograms to about 90 micrograms, about 5 micrograms to about 85 micrograms, about 5 micrograms to about 80 micrograms, about 5 micrograms to about 75 micrograms, about 5 micrograms to about 70 micrograms, about 5 micrograms to about 65 micrograms, about 5 micrograms to about 60 micrograms, about 5 micrograms to about 55 micrograms, about 5 micrograms to about 50 micrograms, about 5 micrograms to about 45 micrograms, about 5 micrograms to about 40 micrograms, about 5 micrograms to about 35 micrograms, about 5 micrograms to about 30 micrograms, about 5 micrograms to about 25 micrograms, about 5 micrograms to about 20 micrograms, about 5 micrograms to about 15 micrograms, about 5 micrograms to about 10 micrograms, less than 10 micrograms (e.g. about 5, 6, 7, 8, or 9 micrograms), about 10 micrograms, about 12 micrograms, about 14 micrograms, about 15 micrograms, about 16 micrograms, about 18 micrograms, about 20 micrograms, about 30 micrograms, about 50 micrograms).

Embodiment 38. The method according to Embodiments 35, 36 or 37, wherein said subject is mammal, preferably human.

Embodiment 39. The method according to any one of Embodiments 35 to 38, wherein said agitation is associated with a neurodegenerative disease.

Embodiment 40. The method according to Embodiment 39, wherein said neurodegenerative disease is selected from Alzheimer disease, fronto-temporal dementia (FTD), dementia, dementia with Lewy bodies (DLB), post-traumatic stress disorder, Parkinson's disease, vascular dementia, vascular cognitive impairment, Huntington's disease, multiple sclerosis, Creutzfeldt-Jakob disease, multiple system atrophy, and progressive supranuclear palsy.

Embodiment 41. The method according to any one of Embodiments 35 to 38, wherein the agitation is associated with a neuropsychiatric condition.

Embodiment 42. The method according to Embodiment 41, wherein said neuropsychiatric condition is selected from schizophrenia, bipolar illness (such as mania, disorder), delirium, and depression.

Embodiment 43. The method according to Embodiment 39, wherein the agitation is associated with sundown syndrome in dementia or Alzheimer's disease.

Embodiment 44. The method according to any one of Embodiments 35 to 38, wherein said agitation is associated with an OPD/IPD procedure (e.g. MRI, CT or CAT scan, lumbar puncture, bone marrow aspiration/biopsy, tooth extraction or other dental procedures).

Embodiment 45. The method according to any one of Embodiments 35 to 38, wherein said agitation is associated with an alcohol and substance abuse withdrawal.

Embodiment 46. The method according to any one of Embodiments 35 to 38, wherein said alpha-2 adrenergic agonist include, but is not limited to, Clonidine, Guanfacine, Guanabenz, Guanoxabenz, Guanethidine, Xylazine, Tizanidine, Medetomidine, Dexmedetomidine, Methyldopa, Methylnorepinephrine, Fadolmidine Iodoclonidine, Apraclonidine, Detomidine, Lofexidine, Amitraz, Mivazerol, Azepexol, Talipexol, Rilmenidine, Naphazoline, Oxymetazoline, Xylometazoline, Tetrahydrozoline, Tramazoline, Talipexole, Romifidine, propylhexedrine, Norfenefrine, Octopamine, Moxonidine, Lidamidine, Tolonidine, UK14304, DJ-7141, ST-91, RWJ-52353, TCG-1000, 4-(3-aminomethyl-cyclohex-3-enylmethyl)-1,3-dihydro-imidazole-2-thione, and 4-(3-hydroxymethyl-cyclohex-3-enylmethyl)-1,3-dihydro-imidazole-2-thione or a pharmaceutically acceptable salt thereof.

Embodiment 47. A method of treating, preventing or reducing the symptoms of agitation in a subject in need thereof, wherein said agitation is associated with neurodegenerative diseases and said method comprises administering to said subject a therapeutically effective amount of Dexmedetomidine, or a pharmaceutically acceptable salt thereof.

Embodiment 48. A method of treating, preventing or reducing the symptoms of agitation in a subject in need thereof, wherein said agitation is associated with sundowning syndrome in dementia or Alzheimer's disease and said method comprises: administering to said subject a therapeutically effective amount of Dexmedetomidine, or a pharmaceutically acceptable salt thereof.

Embodiment 49. A method of treating, preventing or reducing the symptoms of agitation in a subject in need thereof, wherein said agitation is associated with schizophrenia, bipolar disorder, bipolar mania, delirium, intoxication and other neuropsychiatric conditions and said method comprises: administering to said subject a therapeutically effective amount of Dexmedetomidine, or a pharmaceutically acceptable salt thereof.

Embodiment 50. The method as embodied in embodiment 47, wherein said neurodegenerative disease is Dementia, Frontotemporal dementia, Alzheimer's disease, Parkinson's disease, Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-Lemli Opitz syndrome, Fragile x syndrome, Mulvihill-smith syndrome, Transmissible spongiform encephalopathy, Morvan syndrome, Morvan's fibrillary chorea, Peripheral nerve hyperexcitability and Agrypnia Excitata.

Embodiment 51. The method as embodied in embodiment 50, wherein said neurodegenerative disease is preferably Dementia, Frontotemporal dementia, Alzheimer's disease, Parkinson's disease.

Embodiment 52. The method as embodied in embodiments 47 to 49, wherein dexmedetomidine, or a pharmaceutically acceptable salt thereof is administered to said subject by oromucosal route including sublingual or buccal route in the form of pharmaceutical composition.

Embodiment 53. The method as embodied in embodiment 52, wherein dexmedetomidine, or a pharmaceutically acceptable salt thereof is administered to said subject by sublingual route.

Embodiment 54. The method as embodied in embodiments 47 to 49, wherein dexmedetomidine, or a pharmaceutically acceptable salt thereof is administered to said subject (i.e. Human) is in a range of about 1 μg to about 105 μg, preferably 3 μg to 100 μg, more preferably 5 μg to 50 μg.

Embodiment 55. A method of treating, preventing or reducing the symptoms of agitation in a subject in need thereof wherein said agitation is associated with neurodegenerative diseases and said method comprises administering to said subject a pharmaceutical composition comprising a therapeutically effective amount of dexmedetomidine, or a pharmaceutically acceptable salt thereof and pharmaceutical acceptable excipient(s).

Embodiment 56. A method of treating, preventing or reducing the symptoms of agitation in a subject in need thereof wherein said agitation is associated with schizophrenia, bipolar disorder, bipolar mania, delirium, post-traumatic stress disorder, alcohol and substance abuse withdrawal, intoxication and other neuropsychiatric conditions and said method comprises administering to said subject a pharmaceutical composition comprising a therapeutically effective amount of dexmedetomidine, or a pharmaceutically acceptable salt thereof and pharmaceutical acceptable excipient(s).

Embodiment 57. A method of treating, preventing or reducing the symptoms of agitation in a subject in need thereof wherein said agitation is associated with sundowning syndrome in dementia or Alzheimers disease and said method comprises administering to said subject a pharmaceutical composition comprising a therapeutically effective amount of dexmedetomidine, or a pharmaceutically acceptable salt thereof and pharmaceutical acceptable excipient(s).

Embodiment 58. A pharmaceutical composition for use in the treatment, prevention or reduction in the symptoms of agitation in a subject in need thereof wherein said chronic agitation is associated with neurodegenerative diseases and said pharmaceutical composition comprises dexmedetomidine, or a pharmaceutically acceptable salt thereof and pharmaceutical acceptable excipient(s).

Embodiment 59. A pharmaceutical composition for use in the treatment, prevention or reduction in the symptoms of agitation in a subject in need thereof wherein said agitation is associated with schizophrenia, bipolar disorder, bipolar mania, delirium, intoxication and other neuropsychiatric conditions and said pharmaceutical composition comprises dexmedetomidine, or a pharmaceutically acceptable salt thereof and pharmaceutical acceptable excipient(s).

Embodiment 60. A pharmaceutical composition for use in the treatment, prevention or reduction in the symptoms of agitation in a subject in need thereof wherein said agitation is associated with sundowning syndrome in dementia or Alzheimer's disease and said pharmaceutical composition comprises dexmedetomidine, or a pharmaceutically acceptable salt thereof and pharmaceutical acceptable excipient(s).

Embodiment 61. The method/composition as embodied in embodiments 55 and 58, wherein said neurodegenerative disease is selected from Frontotemporal dementia, Dementia, Alzheimer's disease, Parkinson's disease Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-Lemli Opitz syndrome, Fragile x syndrome, Mulvihill-smith syndrome, Transmissible spongiform encephalopathy, Morvan syndrome, Morpervan's fibrillary chorea, Peripheral nerve hyperexcitability and Agryphia Excitata.

Embodiment 62. The method/composition as embodied in embodiment 61, wherein said neurodegenerative disease is preferably Dementia, Frontotemporal dementia, Alzheimer's disease, Parkinson's disease.

Embodiment 63. The method/composition as embodied in embodiments 55 to 60, wherein said pharmaceutical composition is administered to said subject by an oromucosal route including sublingual or buccal route in the form of pharmaceutical composition.

Embodiment 64. The method/composition as embodied in embodiment 63, wherein said pharmaceutical composition is a tablet, film, gel etc.

Embodiment 65. The method/composition as embodied in embodiments 55 to 60, wherein Dexmedetomidine, or a pharmaceutically acceptable salt thereof is administered to said subject (i.e. Human) is in a range of about 1 µg to about 105 µg, preferably about 3 µg to 100 µg, more preferably about 5 µg to 50 µg and most preferably less than 10 µg.

Embodiment 66. Use of dexmedetomidine, or a pharmaceutically acceptable salt thereof composition for treating a subject suffering from agitation associated with neurodegenerative disease.

Embodiment 67. Use of dexmedetomidine, or a pharmaceutically acceptable salt thereof composition for treating a subject suffering from agitation associated with neuropsychiatric conditions including schizophrenia, bipolar disorder, bipolar mania, delirium, intoxication and other neuropsychiatric conditions.

Embodiment 68. Use of dexmedetomidine, or a pharmaceutically acceptable salt thereof composition for treating a subject suffering from agitation associated with sundowning syndrome in dementia or Alzheimer's disease.

Embodiment 69. The use as embodied in embodiment 66, wherein neurodegenerative disease is selected from Frontotemporal dementia, dementia, Alzheimer's disease, Parkinson's disease, Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-Lemli Opitz syndrome, Fragile x syndrome, Mulvihill-smith syndrome, Transmissible spongiform encephalopathy, Morvan syndrome, Morvan's fibrillary chorea, Peripheral nerve hyperexcitability and Agryphia Excitata.

Embodiment 70. The use as embodied in embodiment 69, wherein said neurodegenerative disease is preferably Dementia, Frontotemporal dementia, Alzheimer's disease, Parkinson's disease.

Embodiment 71. A sublingual film composition of dexmedetomidine, or a pharmaceutically acceptable salt thereof for use in the treatment of agitation associated with neurodegenerative disease.

Embodiment 72. A sublingual film composition of dexmedetomidine, or a pharmaceutically acceptable salt thereof for use in the treatment of agitation associated with neuropsychiatric conditions such as bipolar disorder, schizophrenia. bipolar mania. Delirium, intoxication and other neuropsychiatric conditions.

Embodiment 73. A sublingual film composition of dexmedetomidine, or a pharmaceutically acceptable salt thereof for use in the treatment of agitation associated with sundowning syndrome in dementia or Alzheimer's disease.

Embodiment 74. A method of treating, preventing or reducing the symptoms of aggression in a subject in need thereof and said method comprises administering to said subject a pharmaceutical composition comprising a therapeutically effective amount of dexmedetomidine, or a pharmaceutically acceptable salt thereof and pharmaceutical acceptable excipient(s).

Embodiment 75. A method of treating, preventing or reducing the symptoms of agitation in a subject in need thereof, the method comprises administering to said subject dexmedetomidine, or a pharmaceutically acceptable salt thereof through sublingual film in a dose range of 1 µg to 105 µg, preferably about 3 µg to 100 µg and more preferably about 5 µg to 50 µg, more preferably about 5 µg to 20 µg, most preferably less than 10 µg.

Embodiment 76. The method as embodied in embodiment 75, wherein the agitation is acute agitation.

Embodiment 77. The method as embodied in embodiment 75, wherein the agitation is associated with an illness including neurodegenerative disease and/or neuropsychiatric conditions.

Embodiment 78. The method as embodied in embodiment 77, wherein the neurodegenerative disease is selected from the group consisting of neurodegenerative disease Dementia, Frontotemporal dementia, Alzheimer's disease, Parkinson's disease, Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-Lemli Opitz syndrome, Fragile X syndrome, Mulvihill-smith syndrome, Transmissible spongiform encephalopathy, Morvan syndrome, Morvan's fibrillary chorea, Peripheral nerve hyperexcitability and Agrypnia Excitata, sundowning syndrome in dementia or sundowning syndrome in Alzheimer's disease, preferably Dementia, Frontotemporal dementia, Alzheimer's disease or Parkinson's disease.

Embodiment 79. The method as embodied in embodiment 77, wherein the neuropsychiatric conditions is selected from the group consisting of schizophrenia, bipolar disorder, bipolar mania, delirium post-traumatic stress disorder, alcohol and substance abuse withdrawal or intoxication.

Embodiment 80. The method embodied in embodiment 75, wherein dexmedetomidine, or a pharmaceutically acceptable salt thereof is administered to the said subject in a dose ranging from about 1 µg to about 105 µg; preferably from about 3 µg to about 100 µg, more preferably about 5 µg to about 50 µg, most preferably about 5 µg to about 20 µg.

Embodiment 81. A sublingual film comprising about 5 µg to about 100 µg of dexmedetomidine, or a pharmaceutically acceptable salt thereof for use in the treatment of agitation in a subject.

Embodiment 82. The sublingual film as embodied in embodiment 81, wherein the agitation is acute agitation.

Embodiment 83. The sublingual film as embodied in embodiment 82, wherein the agitation is associated with an illness including neurodegenerative disease and/or neuropsychiatric conditions.

Embodiment 84. The sublingual film as embodied in embodiment 83, wherein the neurodegenerative disease is selected from the group consisting of neurodegenerative disease Dementia, Frontotemporal dementia, Alzheimer's disease, Parkinson's disease, Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-LemliOpitz syndrome, Fragile X syndrome, Mulvihill-smith syndrome, Transmissible spongiform encephalopathy, Morvan syndrome, Morvan's fibrillary chorea, Peripheral nerve hyperexcitability, Agrypnia Excitata, sundowning syndrome in dementia or sundowning syndrome in Alzheimer's disease, preferably Dementia, Frontotemporal dementia, Alzheimer's disease or Parkinson's disease.

Embodiment 85. The sublingual film as embodied in embodiment 83, wherein the neuropsychiatric conditions is selected from the group consisting of schizophrenia, bipolar disorder, bipolar mania, delirium post-traumatic stress disorder, alcohol and substance abuse withdrawal or intoxication.

Embodiment 86. The sublingual film as embodied in embodiment 81, wherein the film comprises dexmedetomidine, or a pharmaceutically acceptable salt thereof ranging from about 1 µg to about 105 µg; preferably from about 3 µg to about 100 µg, more preferably about 5 µg to about 50 µg and most preferably about 5 µg to about 20 µg and less than 10 µg.

Embodiment 87. Use of dexmedetomidine, or a pharmaceutically acceptable salt thereof for treating, preventing or reducing the symptoms of agitation in a subject in need thereof, wherein the agitation or aggression is not perioperative agitation.

Embodiment 88. The use as embodied in embodiment 87, wherein the agitation is associated with an illness including neurodegenerative disease and/or neuropsychiatric conditions.

Embodiment 89. The use as embodied in embodiment 88, wherein the neurodegenerative disease is selected from the group consisting of neurodegenerative disease Dementia, Frontotemporal dementia, Alzheimer's disease, Parkinson's disease, Multiple system atrophy, Creutzfeldt-jakob disease, Corticobasal degeneration, Gerstmannstraussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-LemliOpitz syndrome, Fragile X syndrome, Mulvihill-smith syndrome, Transmissible spongiform encephalopathy, Morvan syndrome, Morvan's fibrillary chorea, Peripheral nerve hyperexcitability, Agrypnia Excitata, sundowning syndrome in dementia or sundowning syndrome in Alzheimer's disease, preferably Dementia, Frontotemporal dementia, Alzheimer's disease and Parkinson's disease.

Embodiment 90. The use as embodied in embodiment 88, wherein the neuropsychiatric conditions are selected from the group consisting of schizophrenia, bipolar disorder, bipolar mania, delirium post-traumatic stress disorder, alcohol and substance abuse withdrawal and intoxication.

Embodiment 91. The use as embodied in embodiment 87, wherein the agitation is acute agitation.

Embodiment 92. The use as embodied in embodiment 87, wherein Dexmedetomidine, or a pharmaceutically acceptable salt thereof is administered to said subject by oromucosal route preferably by sublingual or buccal route.

Embodiment 93. The use as embodied in embodiment 92, wherein Dexmedetomidine, or a pharmaceutically acceptable salt thereof is administered in form of pharmaceutical composition selected from the group comprising of tablet, film and gel.

Embodiment 94. The use as embodied in embodiment 87, wherein Dexmedetomidine, or a pharmaceutically acceptable salt thereof is administered to the said subject in a dose ranging from about 1 µg to about 105 µg; preferably from about 3 µg to about 100 µg, more preferably about 5 µg to about 50 µg, most preferably about 5 µg to about 20 µg and most preferably less than 10 µg.

Embodiment 95. A method of treating, preventing or reducing the symptoms of agitation in a subject in need thereof, the method comprises administering to said subject a therapeutically effective amount of dexmedetomidine, or a pharmaceutically acceptable salt thereof by sublingual route, wherein the agitation is not perioperative agitation.

Embodiment 96. A sublingual pharmaceutical composition for treating, preventing or reducing the symptoms of agitation in a subject in need thereof, the composition comprises a therapeutically effective amount of dexmedetomidine, or a pharmaceutically acceptable salt thereof and one or more pharmaceutical excipient, wherein the agitation is not perioperative agitation.

Embodiment 97. A sublingual use of dexmedetomidine, or a pharmaceutically acceptable salt thereof for treating, preventing or reducing the symptoms of agitation in a subject in need thereof, wherein the agitation is not perioperative agitation.

Embodiment 98. A sublingual composition of dexmedetomidine, or a pharmaceutically acceptable salt thereof for use in the treatment of agitation associated with neurodegenerative disease.

Embodiment 99. A sublingual composition of dexmedetomidine, or a pharmaceutically acceptable salt thereof for use in the treatment of agitation associated with bipolar disorder, schizophrenia. bipolar mania. Delirium, intoxication and other neuropsychiatric conditions.

Embodiment 100. A sublingual composition of dexmedetomidine, or a pharmaceutically acceptable salt thereof for use in the treatment of agitation associated with sundowning syndrome in dementia or Alzheimer's disease.

Embodiment 101. A method of treating, preventing or reducing the symptoms of agitation which is other than perioperative agitation in a subject in need thereof, the method comprises administering to said subject a therapeutically effective amount of dexmedetomidine, or a pharmaceutically acceptable salt thereof by sublingual route.

Embodiment 102. A sublingual film for treating, preventing or reducing the symptoms of agitation which is other than perioperative agitation in a subject in need thereof, the method comprises administering to said subject a therapeutically effective amount of dexmedetomidine, or a pharmaceutically acceptable salt thereof.

Embodiment 103. A method of treating, preventing or reducing the symptoms of aggression in a subject in need thereof and said method comprises administering to said subject a pharmaceutical composition comprising a therapeutically effective amount of dexmedetomidine, or a pharmaceutically acceptable salt thereof and pharmaceutical acceptable excipient(s).

Embodiment 104. The method as embodied in embodiment 96, wherein the agitation is associated with an illness including neurodegenerative disease and/or neuropsychiatric conditions.

Embodiment 105. The method as embodied in embodiment 102, wherein the neurodegenerative disease is selected from the group consisting of neurodegenerative disease Dementia, Frontotemporal dementia, Alzheimer's disease, Parkinson's disease, Multiple system atrophy, Creutzfeldt-jakob disease, Corticobasal degeneration, Gerstmann-straussler-scheinker syndrome, Huntington disease, Fatal familial insomnia, Cushing's syndrome, Hypercortisolism, Neurofibromatosis type 1, Norrie disease, Progressive supranuclear palsy, Hereditary spastic paraplegia, Alpers syndrome, Smith-LemliOpitz syndrome, Fragile X syndrome, Mulvihill-smith syndrome, Transmissible spongiform encephalopathy, Morvan syndrome, Morvan's fibrillary chorea, Peripheral nerve hyperexcitability, Agryphia Excitata, sundowning syndrome in dementia or sundowning syndrome in Alzheimer's disease, preferably Dementia, Frontotemporal dementia, Alzheimer's disease or Parkinson's disease.

Embodiment 106. The method as embodied in embodiment 102, wherein the neuropsychiatric conditions is selected from the group consisting of schizophrenia, bipolar disorder, bipolar mania, delirium post-traumatic stress disorder, alcohol and substance abuse withdrawal or intoxication.

Embodiment 107. The method as embodied in embodiment 96, wherein dexmedetomidine, or a pharmaceutically acceptable salt thereof is administered to said subject by oromucosal route preferably by sublingual or buccal route.

Embodiment 108. The method as embodied in embodiment 105, wherein dexmedetomidine, or a pharmaceutically acceptable salt thereof is administered in form of pharmaceutical composition selected from the group comprising of tablet, film or gel.

Embodiment 109. A method of treating, preventing or reducing the symptoms of agitation in a subject in need thereof wherein said agitation is associated with other conditions such as OPD/IPD Procedures like MRI, CT or CAT Scan, Lumbar Puncture, Bone marrow aspiration/biopsy, Tooth extraction or other dental procedures and said method comprises administering to said subject a pharmaceutical composition comprising a therapeutically effective amount of dexmedetomidine, or a pharmaceutically acceptable salt thereof and pharmaceutical acceptable excipient(s).

Embodiment 110. The methods/composition as embodied in the preceding embodiments, wherein the pharmaceutical composition includes intranasal formulations, parenteral formulations, oral formulations, transdermal formulations, liposomal formulations and the like.

The Embodiments hereinabove are not intended to be limiting, and, in practicing the present invention, alternative or additional Embodiments may be provided.

VII. Examples

The following Examples are intended to be illustrative and not limiting.

Example 1

Formulation 1: Sub-Lingual Tablet

TABLE 1

Composition for a typical Sub-lingual tablet formulation used for sublingual delivery

| Ingredients | Quantity | Ranges |
|---|---|---|
| Dexmedetomidine HCl (equivalent to base) | 50 micrograms | |
| Povidone | 5.0 mg | 1.0-10.0% |
| Croscarmellose Sodium | 7.0 mg | 5-15% |
| Sucralose | 1.0 mg | 0.05-3.0% |
| Magnesium Stearate | 0.75 mg | 0.1-2.0% |
| Talc | 0.75 mg | 0.1-2.0% |
| Mannitol | q.s 75.0 mg | q.s. 100% |
| Water | q.s | |

Manufacturing Process

Dexmedetomidine hydrochloride and excipients such as binder and sweetener are dissolved/dispersed into a pharmaceutically acceptable solvent (preferably water) and this solution is used to granulate the sifted blend of all other ingredients except lubricant and glidant in suitable mixer/granulator. The granules are then dried in a fluid-bed drier or other suitable one such as tray drier. The dried granules are then sized appropriately in quadro-co-mill or multi-mill. The sized granules are then loaded into a suitable blender such as V-blender and lubricated with Magnesium stearate and Talc and then the final lubricated blend is then used for compressing into tablets of specific dimensions using appropriate tooling.

Formulation 2: Sub-Lingual Film

TABLE 2

Composition for a typical Sub-lingual film formulation used for sublingual delivery

| Ingredients | Quantity | Ranges |
|---|---|---|
| Dexmedetomidine HCl (equivalent to base) | 50 micrograms | |
| Polyethylene oxide | 5.0 mg | 3-25% |
| Polyethylene Glycol | 5.0 mg | 3-25% |
| Sucralose | 0.2 mg | 0.05-3.0% |
| Flavoring agent | q.s. | 0.01-1.0% |
| Coloring agent | q.s. | 0.01-1.0% |
| Povidone | q.s. 50 mg | q.s. 100% |

Manufacturing Process

Dexmedetomidine hydrochloride along with film forming polymers and other excipients are dissolved/dispersed into a pharmaceutically acceptable solvent (preferably water) and the resulting solution is then coated (spread/cast) on an inert backing layer. Dexmedetomidine hydrochloride containing polymeric layer is further dried, separated and cut into suitable sizes using appropriate die/tools and then packed as per the requirement.

Formulation 3: Sub-Lingual Spray

TABLE 3

Composition for a typical Sub-lingual spray formulation used for sublingual delivery

| Ingredients | Quantity | Ranges |
|---|---|---|
| Dexmedetomidine HCl (equivalent to base) | 50 micrograms | |
| Propylene Glycol | 10 μL | 1.0-40.0% |
| Alcohol | 5 μL | 1.0-40.0% |
| Citric acid | 0.2 mg | 0.1-10% |
| Peppermint Oil | 1 μL | 0.05-3.0% |
| Purified water | q.s. 100 μL | q.s. 100% |

Manufacturing Process

Dexmedetomidine hydrochloride along with all other excipients are mixed in a suitable order. The resulting solution/dispersion is then filled into spray canisters using appropriate tooling. They are further processed with Metered nozzles so that a specified amount of Dexmedetomidine is delivered after actuation each time.

Formulation 4: Sub-Lingual Liquid Drops

TABLE 4

Composition for typical Sub-lingual liquid drops used for sublingual delivery

| Ingredients | Quantity |
|---|---|
| Dexmedetomidine HCl (equivalent to base) | 10 mg |

TABLE 4-continued

Composition for typical Sub-lingual liquid drops used for sublingual delivery

| Ingredients | Quantity |
|---|---|
| Normal saline (0.9% Sodium Chloride) | q.s |

Manufacturing Process

Dexmedetomidine hydrochloride ((Catalogue No. SML0956) was dissolved in Normal saline in order to yield the concentration of 1 mg/ml of the sublingual drops.

Example 2

Evaluate the effect of sublingual and intravenous administration of Dexmedetomidine hydrochloride in rat 'resident-intruder' model of agitation or aggression at varying dosages.

The resident-intruder model is an established preclinical model of aggression and agitation, and allows spontaneous and natural expression of both offensive aggression/agitation and defensive behavior in laboratory rodents in a semi natural laboratory setting. When rodents are exposed to a novel male in their home cage environment, they perceive the novel male animal as an "intruder" and demonstrate a repertoire of defensive behaviors such as ano-genital sniffing, chasing, biting and attacking (Nelson et al., ILAR Journal (2000) 41(3): 153-162).

Materials and Methods:

Animals: 12-13 week old male Wistar rats weighing 380-400 g were used as resident males. 7-8 weeks old male rats weighing 280-300 g were used as the "intruder". Resident rats were housed with female rats for 8 days to establish territoriality. The intruder rats were housed in groups of 3 with other male rats of similar age/body weight. All animals were maintained in a controlled environment with 22±3° C. temperature, 50±20% humidity, a light/dark cycle of 12 hours each and 15-20 fresh air changes per hour and had access to food and water ad-libitum. All animal experiments were conducted in accordance with the guidelines of the Committee for the Purpose of Control and Supervision of Experiments on Animals (CPCSEA), Government of India the Association for Assessment and Accreditation of Laboratory Animal Care international (AAALAC).

Formulation tested: The required quantity of Formulation 4 of dexmedetomidine hydrochloride was weighed and serial dilutions were made to obtain respective doses as per the Table 5. Dilutions were prepared fresh every day prior to dosing using 0.9% normal saline from the formulation 4 for the entire study.

Experimental Procedure: Following acclimatization for a period of 3-5 days, each resident male rat was housed with a female rat for 8 days. On day 8, basal aggression in the resident males was tested by exposing them to an "intruder rat" for 10 minutes. Only animals that demonstrated aggression in this basal aggression test were used for the study. These animals were then randomized using body weight stratification method. The weight variation of the animals did not exceed 20% of the mean body weight in a group at the time of randomization. Animals were housed with the female rat for an additional day. On day 9, the resident animal was paired with intruder animal of an appropriate bodyweight such that the body weight of the resident was always higher than the intruder. This was to facilitate dominant, aggressive behavior in the resident animals. After randomization, animals were assigned a permanent number. Cages were identified by cage cards indicating the study number, study code, group number, sex, dose, cage number and animal number details.

Resident male rats were dosed with different doses of Dexmedetomidine hydrochloride (Dex) 15 minutes prior to the behavioral testing either sublingually or intravenously (Table 5). For sublingual dosing, the rats were held in one hand and using a blunt spatula the tongue was moved to one side of the mouth. Dexmedetomidine hydrochloride was then administered sublingually as liquid drops at specific concentration using a micropipette and allowed to be absorbed for a duration of 50-60 seconds. Diazepam was used as a reference compound and was dosed intraperitoneally. Vehicle controls were treated with 0.9% saline administered sublingually or intravenously. Normal controls (NC) did not received any treatment.

The behavior of the resident rat was recorded using an overhead video camera for 15 minutes and offline behavioral analysis was done using the Noldus Ethovision XT software. To distinguish the resident rat from the intruder rat in the video recording, the intruder rat was marked with non-toxic paint. For analysing the potential effects of Dexmedetomidine hydrochloride on agitation, we quantified various behavioral parameters such as anogenital sniffing, chasing, biting, attacking and latency to attack as well as neutral behavioral parameters such as exploration grooming, and immobile quiet time.

TABLE 5

Efficacy Study: Drug treatment groups

| Group No. | No. of animals | Cohort 1 (Sublingual dosing - Formulation 4 adjusted to following doses) | Cohort 2 (Intravenous dosing - Dexmedetomidine hydrochloride in water or Normal saline) |
| --- | --- | --- | --- |
| 1 | 8 | Normal Control | |
| 2 | 8 | Vehicle control | Vehicle control |
| 3 | 8 | Dexmedetomidine hydrochloride (0.5 µg/kg) | Dexmedetomidine hydrochloride (0.5 µg/kg) |
| 4 | 8 | Dexmedetomidine hydrochloride (1.0 µg/kg) | Dexmedetomidine hydrochloride (1.0 µg/kg) |
| 5 | 8 | Dexmedetomidine hydrochloride (1.5 µg/kg) | Dexmedetomidine hydrochloride (1.5 µg/kg) |
| 6 | 8 | Dexmedetomidine hydrochloride (3.0 µg/kg) | Dexmedetomidine hydrochloride (3.0 µg/kg) |
| 7 | 8 | Diazepam (3 mg/kg, i.p.) | |

Statistical Analysis: Statistical analysis was performed using validated statistical software (GraphPad Prism 6). Data is represented as Mean±SEM. One-way ANOVA (analysis of variance) followed by "Dunnett's Multiple Comparison Test" at 95% confidence interval was applied for comparison of the relevant groups. $p<0.05$ was considered significant.

Results: The present study was performed to evaluate the effect of sublingually/intravenously administered different doses of Dexmedetomidine hydrochloride on agitated behavior in a rat resident-intruder model of aggression and agitation behavior.

Effect of Sublingually/Intravenously Administered Dexmedetomidine Hydrochloride on Aggressive/Agitative Behavior in the Rat Resident Intruder Model:

The rats demonstrate a variety of defensive agitated behaviors such as anogenital sniffing, chasing, biting and attacking (indices of agitative and aggressive behavior) when exposed to a novel male in their home cage environment. The non-resident male is perceived as intruder and the resident male gets agitated and attacks the intruder male to protect their home territory. In the present experiments, vehicle treated rats demonstrated a wide repertoire of aggressive behaviors and the intruder rat was subjected to anogenital sniffing, attack, chasing and biting by the resident or dominant rat.

Dexmedetomidine hydrochloride (Dex) administered sublingually reduced the frequency and duration of these behaviors in a dose related manner (FIG. 1A, and FIG. 1B). Significant reduction was observed in chasing and attacking compared to vehicle control group. Similarly, intravenous administration of dexmedetomidine hydrochloride (Dex) reduced all the indices of aggressive and agitated behaviors (FIG. 1C and FIG. 1D). A significant reduction in anogenital sniffing, biting and attacking compared to vehicle controls was observed at doses above 0.5 µg/kg (FIG. 1C and FIG. 1D). Reference compound diazepam (3 mg/kg, i.p) also produced significant reduction in all the indices of aggressive and agitated behaviors evaluated in this study (FIG. 1A-1D).

Effect of Sublingually/Intravenously Administered Dexmedetomidine Hydrochloride on Latency to Attack In addition to the change in frequency and duration of attack by the resident male, we also evaluated the effect of Dexmedetomidine hydrochloride (Dex) on the latency to attack the intruder rat. We observed an increase in the latency to attack the intruder rat following sublingual administration of Dexmedetomidine hydrochloride (Dex) in a dose related fashion indicating a reduction in aggression and agitation (FIG. 2A). When Dexmedetomidine hydrochloride (Dex) was administered intravenously, a similar increase in the latency to attack the intruder rat occurred in a dose related fashion that was significant compared to vehicle controls at a dose of 3 µg/kg (FIG. 2B). Animals treated with diazepam demonstrated a complete lack of attacking behavior (FIGS. 2A and 2B).

Effect of Sublingually/Intravenously Administered Dexmedetomidine Hydrochloride on Neutral Behaviors Neutral behaviors like grooming, exploration and immobile/quiet time were assessed following treatment with Dexmedetomidine hydrochloride. No significant changes occurred in the grooming and exploration following sublingual administration of Dexmedetomidine hydrochloride except a reduction in exploration observed at doses of 1.5 µg/kg & 3 µg/kg (FIGS. 3A and 3B), compared to vehicle controls. Similarly, intravenously administered Dexmedetomidine hydrochloride did not significantly affect grooming and exploration in comparison to vehicle controls except at a dose of 3 µg/kg. In case of immobile/quiet time, there was no significant effect of sublingually administered Dexmedetomidine hydrochloride compared to vehicle controls however, intravenously administered Dexmedetomidine hydrochloride significantly increased the immobile/quiet time at a dose of 3 µg/kg (FIG. 3C, and FIG. 3F). Reference compound Diazepam (3 mg/kg, ip) significantly reduced the frequency and duration of all neutral behaviors evaluated in this study.

Interpretation

In the present study, we investigated the potential of Dexmedetomidine hydrochloride in reducing aggression and agitation in rat resident-intruder model. The resident-intruder model is an established preclinical model of aggression/agitation and allows spontaneous and natural expression of both offensive aggression/agitation and defensive behavior in laboratory rodents in a semi natural laboratory setting.

1. Sublingual administration of Dexmedetomidine hydrochloride resulted in a dose related reduction in several behavioral indices of aggression and agitation such as anogenital sniffing, chasing, attacking and biting.
2. A significant increase in the latency to attack the intruder rat was observed in a dose related manner with prior treatment with Dexmedetomidine hydrochloride as compared to the vehicle control group.
3. No changes were observed in neutral behavior of animals, indicating the lack of overt anxiety-like behavior in the resident rats treated with sublingually administered Dexmedetomidine hydrochloride.
4. Of the doses that were used in the study (0.5-3 µg/kg), doses of 1-1.5 µg/kg (doses administered sublingually or intravenously) effectively reduced the behavioral indices of aggression and agitation without majorly impacting the neutral behaviors.

Conclusion: Dexmedetomidine hydrochloride effectively reduces various indices of agitation and aggression in rat resident intruder model. Dose of 1-1.5 µg/kg effectively reduced the behavioral indices of aggression and agitation without majorly impacting the neutral behaviors. In the present study the efficacy of sublingually administered Dexmedetomidine hydrochloride correlates with intravenously administered Dexmedetomidine hydrochloride at these doses (Table 6).

| | p values obtained after statistical comparison of sublingual vs intravenous route of administration using Student's t-test Duration (sec) | | | | |
|---|---|---|---|---|---|
| Group | Chasing | Biting | Attack/ Fighting | Anogenital-sniffing | Latency to attack |
| NC | 1.000 | 1.000 | 1.000 | 1.000 | 1.000 |
| Vehicle | 0.207 | 0.069 | 0.290 | 0.753 | 0.136 |
| 1 µg/kg | 0.506 | 0.102 | 0.204 | 0.090 | 0.207 |
| 1.5 µg/kg | 0.125 | 0.059 | 0.107 | 0.727 | 0.508 |

Based on 1-1.5 µg/kg rat efficacy doses, the human equivalent sublingual doses are calculated to be 0.161 µg/kg & 0.242 µg/kg. The total human equivalent dose for a 60-kg human would be 10 and 15 µg (https://www.fda.gov/downloads/drugs/guidances/ucm078932.pdf).

Example 3: Estimation of Dexmedetomidine (0.5-3 µg/Kg) in Rat Plasma Samples by LC-MS/MS Objective: To estimate Dexmedetomidine levels in rat plasma samples obtained after dosing animals via intravenous and sublingual routes at doses of 0.5, 1, 1.5 and 3 µg/kg.

Blood collection: To determine the plasma concentration of dexmedetomidine, Dexmedetomidine hydrochloride was administered sublingually or intravenously in rats (n=3) at different doses (Formulation 4 adjusted to 0.5, 1, 1.5, 3 µg/kg). Blood was collected under mild isoflurane anesthesia from the retro-orbital plexus at 0, 5, 15, 30, 60 and 120 minutes post dosing. Plasma was separated and stored at −80° C. until Dexmedetomidine concentration was analyzed.

Materials and Methods

Preparation of Standard Solutions

A standard stock solution of dexmedetomidine hydrochloride was prepared by dissolving 1.358 mg of dexmedetomidine hydrochloride in 1358 µl of milli-Q water to achieve a concentration of 829.071 mg/ml. Working solutions of different concentrations were prepared by using diluent (methanol: water (50:50) % v/v).

Tolbutamide was used as an internal standard and its stock solution was prepared by dissolving 25 mg of tolbutamide in 1000 µl of DMSO to achieve a concentration of 25 mg/ml. Working solutions of different concentrations were prepared by using a diluent (acetonitrile: water (50:50) % v/v).

Solution preparation for SPE and chromatography: Mobile phase A (10 mm ammonium formate, pH 3.50): 0.6306 gms of ammonium formate was weighed and transferred to a 1000 ml reagent bottle. To this, 1000 ml of milli q water was added and pH of the resulting solution was adjusted to 3.5 using formic acid.

Mobile phase B: 100% acetonitrile

Diluent (methanol: water (50:50) % v/v): 50 ml of methanol was mixed with 50 ml of milli-q water. Resulting solution was used as diluent.

Wash solution. 100 µl of ammonia was mixed with 100 ml of milli q. Resulting solution was used as wash solution.

Elution solvent: 100 µl of formic acid was mixed with 100 ml of acetonitrile. Resulting solution was used as elution solvent.

Analytical Methods: Samples were analysed by using Agilent 1290 Infinity II HPLC system coupled to AB Sciex Triple Quad instrument (API-5000). Chromatographic separation was done using Agilent Zorbax Eclipse plus C18 column (50*2.1 mm, 1.8 µm) in gradient mode. The mobile phase consisted of 10 mM Ammonium Formate with pH 3.5 (Mobile phase A) and 100% Acetonitrile (Mobile phase B). The column temperature was 40° C. and flow rate was 0.35 mL/min. The MS instrument was operated in the positive mode (ESI+). For analysis, 2 µL of sample was injected into the LC-MS/MS instrument. Auto sampler temperature was 7° C.

Quality control (QC) samples were prepared as following as per table 7:

TABLE 7

| Dexmedetomidine conc (Solution A) (ng/mL) | Volume of solution A (µL) | Blank plasma (µL) | Total Volume (µL) | Final Calibration Conc (µg/mL) | QC ID |
|---|---|---|---|---|---|
| 1.114 | 2 | 48 | 50 | 44.571 | LQC |
| 371.424 | 2 | 48 | 50 | 14856.962 | MQC |
| 928.560 | 2 | 48 | 50 | 37142.406 | HQC |

Sample Preparation

WCX SPE 96 well plate was used for sample preparation. 50p of plasma sample was used for extraction. Along with study samples, one set of linearity and two sets of quality controls (QC) were also processed.

Sample pretreatment: To 50 µl of plasma, 10 µl of tolbutamide working solution was added (Tolbutamide 250 ng/ml). After mixing, 50 µL of buffer solution (10 mM Ammonium Formate pH 3.5) was added. Contents were vortex mixed and loaded to preconditioned SPE plate.

LC-MS/MS Analysis

After placing the cartridges in the negative pressure SPE unit, they were conditioned by passing 200 μl of 100% methanol followed by 200 μl of water. The pretreated plasma samples were then loaded to the pre-conditioned cartridges.

After loading pretreated plasma samples, cartridges were washed with 100 μl of 0.1% ammonia solution. Finally, bound analyte was eluted with 50 μl of 0.1% formic acid in acetonitrile. This step was repeated twice for complete elution. Final eluent volume was 100 μL. To 100 μL of eluent, 50 μL of 10 mM ammonium formate (pH 3.5) was added samples were vortex mixed and transferred to a 96-well HPLC sample plate (Agilent) and submitted for LC-MS/MS analysis. For LC-MS/MS analysis, 2 μL of sample was injected. Calibration standards and QCs were processed the same way as done for study samples.

Mean plasma concentrations of Dexmedetomidine in various rat plasma samples at various time points was determined by LC-MS/MS method using Analyst 1.6.2 software (Table 8 and FIGS. 4A and 4B) with a calibration curve in the range of 0.011-53.061 ng/ml prepared in blank rat plasma matrix. The calibration curve was fitted by linear regression. The concentrations in the QC and test samples (μg/mL) were obtained from the Analyst software based on the calibration curve. Acceptance criteria for the calibration curve and QCs are as follows: 1) At least 75% of the non-zero calibration standards must be included in the calibration curve with all back-calculated concentrations within ±20% deviation from nominal concentrations (except for the lower level of quantification, LLOQ, where ±20% deviation is acceptable). 2) The correlation coefficient (r) of the calibration curve must be greater than or equal to 0.99. 3) At least two-thirds (4 out of 6) QC samples must be within ±20% relative error (accuracy)

Results:

INTERPRETATION AND CONCLUSION

Following sublingual administration of Dexmedetomidine hydrochloride, a dose-related effect on plasma concentrations was observed at doses ranging from 0.5-3 μg/kg (FIG. 4A, table 8).

Following intravenous administration of Dexmedetomidine hydrochloride, a dose-dependent effect on plasma concentrations was observed at doses ranging from 0.5-3 μg/kg (FIG. 4B, table 8).

Doses of 1 and 1.5 μg/kg effectively reduced various indices of agitation and aggression without majorly impacting neutral behaviors. Plasma concentrations following administration of dose of 1 μg/kg (via sublingual and intravenous route) between 15 to 30 min (time corresponding to the time of behavioral response observed in the efficacy study; drug administered 15 min prior to agitation behavior test & animal observed for 15 min) range from 43±13.5 to 90±12.1 μg/ml (Table 8). Similarly, plasma concentrations following administration of dose of 1.5 μg/kg (via sublingual and intravenous route) between 15 to 30 min range from 27±7.1–114±1.7 μg/ml (Table 8).

What is claimed is:

1. A method of treating agitation in an agitated subject, said agitated subject having schizophrenia, consisting of administering to the oral mucosa of said agitated subject one or two single dosage administrations of 60 micrograms of dexmedetomidine or a pharmaceutically acceptable salt thereof without also causing significant sedation after the administration, wherein the dexmedetomidine or the pharmaceutically acceptable salt thereof produces an anti-agitation effect in less than about 60 minutes after administration; wherein the agitation is not perioperative agitation; and wherein said dexmedetomidine or a pharmaceutically acceptable salt thereof is administered in a solid, water-soluble dosage form and wherein the dosage form is a film.

2. The method of claim 1, wherein said dexmedetomidine or a pharmaceutically acceptable salt thereof is administered sublingually.

TABLE 8

Mean rat plasma concentrations following Sublingual or Intravenous dexmedetomidine hydrochloride administration at varying doses

| Sublingual Dosing | Mean Concentration in pg/mL at various time points after dosing | | | | | | Intravenous dosing | Concentration in pg/mL at various time points after dosing | | | | | |
|---|---|---|---|---|---|---|---|---|---|---|---|---|---|
| groups (I-IV) | 0 min | 5 min | 15 min | 30 min | 60 min | 120 min | groups (V-VIII) | 0 min | 5 min | 15 min | 30 min | 60 min | 120 min |
| I-Dex.HCl 0.5 μg/kg, SL | BLQ | 48 ± 30.4 | 51 ± 29.1 | 87 ± 89.7 | 17 ± 0.7 | BLQ | V-Dex.HCl 0.5 μg/kg, i.v. | BLQ | 70 ± 7.2 | 46 ± 14.2 | 35 ± 4.9 | 19 ± 3.5 | BLQ |
| II-Dex.HCl 1 μg/kg, SL | BLQ | 51 ± 44.7 | 47 ± 22.4 | 43 ± 13.5 | 13 ± 2.8 | 19 ± 7.07 | VI-Dex.HCl 1 μg/kg, i.v. | BLQ | 174 ± 12.5 | 90 ± 12.1 | 45 ± 1.7 | 63 ± 58.0 | BLQ |
| III-Dex.HCl 1.5 μg/kg, SL | BLQ | 84 ± 37.7 | 27 ± 7.1 | 31 ± 5.5 | 37 ± 16.3 | 36 ± 6.36 | VII-Dex.HCl 1.5 μg/kg, i.v. | BLQ | 158 ± 56.1 | 114 ± 1.7 | 65 ± 11.0 | 31 ± 10.3 | 21 ± 8.89 |
| IV-Dex.HCl 3 μg/kg, SL | BLQ | 71 ± 52.0 | 42 ± 13.0 | 160 ± 117.9 | 96 ± 21.5 | 93 ± 53.95 | VIII-Dex.HCl 3 μg/kg, i.v. | BLQ | 471 ± 24.9 | 266 ± 31.6 | 139 ± 18.0 | 84 ± 17.4 | 34 ± 9.61 |

BLQ: Below the Lowest limit of Quantification of the assay (LOQ: 0.05 ng/ml)

SL: sublingual; i.v.: intravenous

Data expressed as Mean ± SD

3. The method of claim 1, wherein said dexmedetomidine or a pharmaceutically acceptable salt thereof is administered buccally.

4. The method of claim 1, wherein said dexmedetomidine or a pharmaceutically acceptable salt thereof is dexmedetomidine hydrochloride.

5. The method of claim 1, wherein the agitation is acute agitation.

6. The method of claim 1, wherein the agitation is chronic agitation.

* * * * *